US009962147B2

(12) United States Patent
O'Connell et al.

(10) Patent No.: US 9,962,147 B2
(45) Date of Patent: May 8, 2018

(54) MINIMALLY DISRUPTIVE RETRACTOR AND ASSOCIATED METHODS FOR SPINAL SURGERY

(71) Applicant: NuVasive, Inc., San Diego, CA (US)

(72) Inventors: Casey James O'Connell, San Diego, CA (US); James Coleman Lee, San Diego, CA (US); Ali A. Shorooghi, Mission Viejo, CA (US)

(73) Assignee: NuVasive, Inc., San Diego, CA (US)

( * ) Notice: Subject to any disclaimer, the term of this patent is extended or adjusted under 35 U.S.C. 154(b) by 0 days. days.

(21) Appl. No.: 15/791,070

(22) Filed: Oct. 23, 2017

(65) Prior Publication Data

US 2018/0055503 A1    Mar. 1, 2018

Related U.S. Application Data

(63) Continuation of application No. 14/756,198, filed on Aug. 14, 2015, now Pat. No. 9,795,370.

(60) Provisional application No. 62/201,739, filed on Aug. 6, 2015, provisional application No. 62/036,776, filed on Aug. 13, 2014.

(51) Int. Cl.
*A61B 17/02* (2006.01)
*A61B 17/00* (2006.01)

(52) U.S. Cl.
CPC ............ *A61B 17/02* (2013.01); *A61B 17/025* (2013.01); *A61B 17/0206* (2013.01); *A61B 17/0218* (2013.01); *A61B 2017/00473* (2013.01); *A61B 2017/0256* (2013.01)

(58) Field of Classification Search
CPC .............. A61B 17/025; A61B 17/0206; A61B 17/0218
See application file for complete search history.

(56) References Cited

U.S. PATENT DOCUMENTS

| 281,880 | A | * | 7/1883 | Hubbell | ............ A61B 17/0206 |
| | | | | | 600/219 |
| 713,166 | A | | 11/1902 | Cyr | |
| 1,223,812 | A | | 4/1917 | Listiak | |
| 1,456,116 | A | | 5/1923 | Bessesen | |
| 1,520,832 | A | | 12/1924 | McConnell | |
| 1,706,500 | A | * | 3/1929 | Smith | .................... A61B 17/02 |
| | | | | | 600/232 |

(Continued)

FOREIGN PATENT DOCUMENTS

| CN | 2215898 U | 12/1995 |
| CN | 2506211 U | 8/2002 |

(Continued)

OTHER PUBLICATIONS

Deutsch and Musacchio, "Minimally invasive transforaminal lumbar interbody fusion with unilateral pedicle screw fixation," *Neurosurg Focus*, 2006 20(3): E10, 5 pages.

(Continued)

*Primary Examiner* — Christian Sevilla
(74) *Attorney, Agent, or Firm* — Rory Schermerhorn; NuVasive, Inc.

(57) ABSTRACT

This application describes a surgical retractor and related methods for providing access to a surgical target site for the purpose performing minimally invasive spinal fusion across one or more segments of the spinal column.

10 Claims, 28 Drawing Sheets

(56) References Cited

U.S. PATENT DOCUMENTS

| | | | |
|---|---|---|---|
| 2,670,731 A * | 3/1954 | Zoll | A61B 17/0206 101/389.1 |
| 2,807,259 A | 9/1957 | Guerriero | |
| 3,030,948 A | 4/1962 | Loeffler | |
| 3,364,919 A | 1/1968 | Hunnicutt | |
| 3,383,769 A | 5/1968 | Davis | |
| 3,384,077 A | 5/1968 | Gauthier | |
| 3,509,873 A | 5/1970 | Karlin | |
| 3,522,799 A | 8/1970 | Gauthier | |
| 3,724,449 A | 4/1973 | Gauthier | |
| 3,749,088 A | 7/1973 | Kohlmann | |
| 3,795,981 A | 3/1974 | Franklin et al. | |
| 3,965,890 A | 6/1976 | Gauthier | |
| 4,116,232 A | 9/1978 | Rabban | |
| 4,156,424 A | 5/1979 | Burgin | |
| 4,165,746 A | 8/1979 | Burgin | |
| 4,300,541 A | 11/1981 | Burgin | |
| 4,421,107 A | 12/1983 | Estes et al. | |
| 4,421,108 A | 12/1983 | Cabrera et al. | |
| 4,467,791 A | 8/1984 | Cabrera et al. | |
| 4,566,466 A | 1/1986 | Ripple et al. | |
| 4,627,421 A | 12/1986 | Symbas et al. | |
| 4,686,972 A | 8/1987 | Kurland | |
| 4,702,230 A | 10/1987 | Pelta | |
| 4,747,394 A | 5/1988 | Watanabe | |
| 4,747,395 A | 5/1988 | Brief | |
| 4,817,587 A | 4/1989 | Janese | |
| 4,829,985 A | 5/1989 | Couetil | |
| 4,852,552 A | 8/1989 | Chaux | |
| 4,877,020 A | 10/1989 | Vich | |
| 4,881,525 A | 11/1989 | Williams | |
| 4,930,932 A | 6/1990 | LeVahn | |
| 4,934,352 A | 6/1990 | Sullivan, Jr. | |
| 4,957,495 A | 9/1990 | Kluger | |
| 5,052,373 A | 10/1991 | Michelson | |
| 5,088,472 A | 2/1992 | Fakhrai | |
| 5,152,279 A | 10/1992 | Wilk | |
| 5,167,223 A * | 12/1992 | Koros | A61B 17/0206 600/211 |
| 5,176,128 A | 1/1993 | Andrese | |
| 5,195,505 A | 3/1993 | Josefsen | |
| 5,199,419 A | 4/1993 | Remiszewski et al. | |
| 5,231,974 A | 8/1993 | Giglio et al. | |
| 5,267,554 A | 12/1993 | Wilk | |
| 5,280,782 A | 1/1994 | Wilk | |
| 5,307,805 A | 5/1994 | Byrne | |
| 5,339,801 A | 8/1994 | Poloyko et al. | |
| 5,341,798 A | 8/1994 | Grounauer | |
| 5,363,841 A | 11/1994 | Coker | |
| 5,375,481 A | 12/1994 | Cabrera et al. | |
| 5,381,788 A | 1/1995 | Matula et al. | |
| 5,400,774 A | 3/1995 | Villalta et al. | |
| 5,417,230 A | 5/1995 | Wood | |
| 5,429,121 A | 7/1995 | Gadelius | |
| 5,431,658 A | 7/1995 | Moskovich | |
| 5,474,056 A | 12/1995 | Laborie et al. | |
| 5,512,038 A | 4/1996 | O'Neal et al. | |
| 5,520,610 A | 5/1996 | Giglio et al. | |
| 5,554,101 A | 9/1996 | Matula et al. | |
| 5,609,593 A | 3/1997 | Errico et al. | |
| D380,548 S | 7/1997 | Koros et al. | |
| 5,728,046 A * | 3/1998 | Mayer | A61B 17/0293 600/210 |
| 5,733,290 A * | 3/1998 | McCue | A61B 17/1735 606/86 R |
| 5,746,743 A | 5/1998 | Greenberg | |
| 5,755,660 A | 5/1998 | Tyagi | |
| 5,755,732 A | 5/1998 | Green et al. | |
| 5,772,583 A | 6/1998 | Wright et al. | |
| D396,285 S | 7/1998 | Koros et al. | |
| 5,782,830 A | 7/1998 | Farris | |
| 5,795,291 A | 8/1998 | Koros et al. | |
| 5,797,909 A | 8/1998 | Michelson | |
| 5,843,121 A | 12/1998 | Yoon | |
| 5,846,192 A | 12/1998 | Teixido | |
| 5,846,193 A | 12/1998 | Wright | |
| 5,882,298 A | 3/1999 | Sharratt | |
| 5,882,299 A | 3/1999 | Rastegar et al. | |
| 5,890,271 A | 4/1999 | Bromley et al. | |
| 5,893,831 A | 4/1999 | Koros et al. | |
| 5,902,233 A * | 5/1999 | Farley | A61B 17/0206 600/213 |
| 5,908,382 A * | 6/1999 | Koros | A61B 17/0206 600/215 |
| 5,928,139 A * | 7/1999 | Koros | A61B 17/0206 600/205 |
| 5,931,777 A * | 8/1999 | Sava | A61B 17/02 600/210 |
| 5,944,658 A * | 8/1999 | Koros | A61B 17/0206 600/231 |
| 5,947,896 A | 9/1999 | Sherts et al. | |
| 5,967,972 A * | 10/1999 | Santilli | A61B 17/0206 600/201 |
| 5,967,973 A | 10/1999 | Sherts et al. | |
| 5,984,865 A | 11/1999 | Farley et al. | |
| 5,984,867 A | 11/1999 | Deckman et al. | |
| 5,993,385 A * | 11/1999 | Johnston | A61B 17/0206 600/213 |
| 6,042,540 A | 3/2000 | Johnston et al. | |
| 6,042,542 A | 3/2000 | Koros et al. | |
| 6,096,038 A | 8/2000 | Michelson | |
| 6,132,370 A | 10/2000 | Furnish et al. | |
| 6,139,493 A * | 10/2000 | Koros | A61B 17/0206 600/213 |
| 6,159,215 A | 12/2000 | Urbahns et al. | |
| 6,196,969 B1 | 3/2001 | Bester et al. | |
| 6,206,826 B1 | 3/2001 | Mathews et al. | |
| 6,206,828 B1 | 3/2001 | Wright | |
| 6,213,940 B1 | 4/2001 | Sherts et al. | |
| 6,224,545 B1 | 5/2001 | Cocchia et al. | |
| 6,241,729 B1 | 6/2001 | Estes et al. | |
| 6,280,442 B1 | 8/2001 | Barker et al. | |
| 6,296,609 B1 | 10/2001 | Brau | |
| 6,319,257 B1 | 11/2001 | Carignan et al. | |
| 6,332,500 B1 | 12/2001 | Ellefsen et al. | |
| 6,340,345 B1 | 1/2002 | Lees et al. | |
| 6,416,465 B2 | 7/2002 | Brau | |
| 6,416,468 B2 | 7/2002 | Deckman et al. | |
| 6,447,443 B1 | 9/2002 | Keogh et al. | |
| 6,454,773 B1 | 9/2002 | Sherman et al. | |
| 6,475,142 B1 | 11/2002 | Parsons et al. | |
| 6,478,800 B1 | 11/2002 | Fraser et al. | |
| 6,506,151 B2 | 1/2003 | Estes et al. | |
| 6,524,238 B2 | 2/2003 | Velikaris et al. | |
| 6,537,212 B2 | 3/2003 | Sherts et al. | |
| 6,551,242 B1 | 4/2003 | Furnish et al. | |
| 6,599,240 B2 | 7/2003 | Puchovsky et al. | |
| 6,599,292 B1 | 7/2003 | Ray | |
| 6,623,485 B2 | 9/2003 | Doubler et al. | |
| 6,632,238 B2 | 10/2003 | Ginn et al. | |
| 6,660,004 B2 | 12/2003 | Barker et al. | |
| 6,675,805 B1 | 1/2004 | Graether | |
| 6,689,054 B2 | 2/2004 | Furnish et al. | |
| 6,692,434 B2 | 2/2004 | Ritland | |
| 6,733,444 B2 | 5/2004 | Phillips | |
| 6,733,445 B2 | 5/2004 | Sherts et al. | |
| 6,749,613 B1 | 6/2004 | Conchy et al. | |
| 6,802,844 B2 | 10/2004 | Ferree | |
| 6,835,196 B2 | 12/2004 | Biedermann et al. | |
| 6,860,850 B2 | 3/2005 | Phillips et al. | |
| 6,869,398 B2 | 3/2005 | Obenchain et al. | |
| 6,887,197 B2 | 5/2005 | Phillips | |
| 6,887,198 B2 | 5/2005 | Phillips et al. | |
| 6,918,911 B2 | 7/2005 | Biedermann et al. | |
| 6,929,606 B2 | 8/2005 | Ritland | |
| 6,945,933 B2 | 9/2005 | Branch et al. | |
| 6,951,538 B2 | 10/2005 | Ritland | |
| 6,964,666 B2 | 11/2005 | Jackson | |
| 6,979,291 B1 | 12/2005 | Phillips et al. | |
| 7,001,333 B2 | 2/2006 | Hamel et al. | |
| 7,004,947 B2 | 2/2006 | Shluzas et al. | |
| 7,011,658 B2 | 3/2006 | Young | |
| 7,014,608 B2 | 3/2006 | Larson et al. | |

(56) References Cited

U.S. PATENT DOCUMENTS

| | | |
|---|---|---|
| 7,029,472 B1 | 4/2006 | Fortin |
| 7,108,698 B2 | 9/2006 | Robbins et al. |
| 7,147,599 B2 | 12/2006 | Phillips et al. |
| 7,150,714 B2 | 12/2006 | Myles |
| 7,166,073 B2 | 1/2007 | Ritland |
| 7,182,729 B2 | 2/2007 | Abdelgany et al. |
| 7,207,949 B2 | 4/2007 | Miles et al. |
| 7,214,186 B2 | 5/2007 | Ritland |
| 7,235,048 B2 | 6/2007 | Rein et al. |
| 7,250,052 B2 | 7/2007 | Landry et al. |
| 7,318,817 B2 | 1/2008 | Hamada |
| 7,341,594 B2 | 3/2008 | Shluzas et al. |
| 7,369,328 B2 | 5/2008 | Yamamoto et al. |
| 7,374,534 B2 | 5/2008 | Dalton |
| 7,455,639 B2 | 11/2008 | Ritland |
| 7,473,223 B2 | 1/2009 | Fetzer |
| 7,481,766 B2 | 1/2009 | Lee et al. |
| 7,494,463 B2 | 2/2009 | Nehls |
| 7,537,565 B2 | 5/2009 | Bass |
| 7,569,014 B2 | 8/2009 | Bass et al. |
| 7,582,058 B1 | 9/2009 | Miles et al. |
| 7,588,537 B2 | 9/2009 | Bass |
| 7,588,593 B2 | 9/2009 | Aferzon |
| 7,618,424 B2 | 11/2009 | Wilcox et al. |
| 7,654,954 B1 | 2/2010 | Phillips et al. |
| 7,655,008 B2 | 2/2010 | Lenke et al. |
| 7,686,809 B2 | 3/2010 | Triplett et al. |
| 7,686,814 B2 | 3/2010 | Lim et al. |
| 7,691,057 B2 | 4/2010 | Miles et al. |
| 7,713,274 B2 | 5/2010 | Shluzas et al. |
| 7,722,618 B2 | 5/2010 | Estes et al. |
| 7,753,844 B2 | 7/2010 | Sharratt et al. |
| 7,758,501 B2 | 7/2010 | Frasier et al. |
| 7,794,464 B2 | 9/2010 | Bridwell et al. |
| 7,815,650 B2 | 10/2010 | Shluzas et al. |
| 7,819,801 B2 | 10/2010 | Miles et al. |
| 7,824,332 B2 | 11/2010 | Fakhrai |
| 7,850,608 B2 | 12/2010 | Hamada |
| 7,905,840 B2 | 3/2011 | Pimenta et al. |
| 7,909,761 B2 | 3/2011 | Banchieri et al. |
| 7,909,829 B2 | 3/2011 | Patel et al. |
| 7,909,848 B2 | 3/2011 | Patel et al. |
| 7,918,792 B2 | 4/2011 | Drzyzga et al. |
| 7,922,658 B2 | 4/2011 | Cohen et al. |
| 7,927,337 B2 | 4/2011 | Keller |
| 7,931,589 B2 | 4/2011 | Cohen et al. |
| 7,935,053 B2 | 5/2011 | Karpowicz et al. |
| 7,946,982 B2 | 5/2011 | Hamada |
| 7,951,168 B2 | 5/2011 | Chao et al. |
| 7,951,175 B2 | 5/2011 | Chao et al. |
| 7,959,564 B2 | 6/2011 | Ritland |
| 7,981,031 B2 | 7/2011 | Frasier et al. |
| 7,981,115 B2 | 7/2011 | Justis et al. |
| 7,988,700 B2 | 8/2011 | Shluzas et al. |
| 8,007,516 B2 | 8/2011 | Chao et al. |
| 8,043,343 B2 | 10/2011 | Miller et al. |
| 8,062,217 B2 | 11/2011 | Boucher et al. |
| 8,066,710 B2 | 11/2011 | Estes et al. |
| 8,083,750 B2 | 12/2011 | Lim et al. |
| 8,097,026 B2 | 1/2012 | Gorek |
| 8,100,828 B2 | 1/2012 | Frey et al. |
| 8,114,016 B2 | 2/2012 | Lo et al. |
| 8,162,827 B2 | 4/2012 | Abdelgany et al. |
| 8,167,887 B2 | 5/2012 | McLean |
| 8,211,012 B2 | 7/2012 | Wing et al. |
| 8,221,474 B2 | 7/2012 | Bridwell et al. |
| 8,226,554 B2 | 7/2012 | McBride et al. |
| 8,298,139 B2 | 10/2012 | Hamada |
| 8,303,499 B2 | 11/2012 | Hamada |
| 8,357,087 B2 | 1/2013 | Fetzer |
| 8,357,184 B2 | 1/2013 | Woolley et al. |
| 8,372,081 B1 | 2/2013 | Schafer et al. |
| 8,376,937 B2 | 2/2013 | Xia et al. |
| 8,388,525 B2 | 3/2013 | Poo et al. |
| 8,409,089 B2 | 4/2013 | Michaeli et al. |
| 8,414,625 B2 | 4/2013 | Gorek |
| 8,435,269 B2 | 5/2013 | Woolley et al. |
| 8,449,549 B2 | 5/2013 | Barry et al. |
| 8,454,504 B2 | 6/2013 | Michaeli et al. |
| 8,517,935 B2 | 8/2013 | Marchek et al. |
| 8,523,876 B2 | 9/2013 | Lim et al. |
| 8,535,320 B2 | 9/2013 | Woolley et al. |
| 8,636,655 B1 | 1/2014 | Childs |
| 8,636,657 B2 | 1/2014 | Hamada |
| 8,663,102 B2 | 3/2014 | Michaeli et al. |
| 8,709,044 B2 | 4/2014 | Chao et al. |
| 8,727,975 B1* | 5/2014 | Pfabe .............. A61B 17/0206 600/231 |
| 9,113,853 B1* | 8/2015 | Casey .............. A61B 17/0206 |
| 9,622,732 B2* | 4/2017 | Martinelli ........... A61B 17/025 |
| 9,795,370 B2* | 10/2017 | O'Connell ......... A61B 17/0206 |
| 2002/0161368 A1 | 10/2002 | Foley et al. |
| 2003/0149341 A1 | 8/2003 | Clifton |
| 2004/0068269 A1 | 4/2004 | Bonati et al. |
| 2004/0147936 A1 | 7/2004 | Rosenberg et al. |
| 2004/0215199 A1 | 10/2004 | Zinkel |
| 2004/0230191 A1 | 11/2004 | Frey et al. |
| 2005/0021031 A1 | 1/2005 | Foley et al. |
| 2005/0080320 A1 | 4/2005 | Lee et al. |
| 2005/0090824 A1 | 4/2005 | Shluzas et al. |
| 2005/0131422 A1 | 6/2005 | Anderson et al. |
| 2005/0148826 A1 | 7/2005 | Paolitto et al. |
| 2005/0165408 A1 | 7/2005 | Puno et al. |
| 2005/0171542 A1 | 8/2005 | Biedermann et al. |
| 2005/0192486 A1 | 9/2005 | Hamel et al. |
| 2005/0192570 A1 | 9/2005 | Jackson |
| 2005/0234304 A1 | 10/2005 | Dewey et al. |
| 2005/0240081 A1 | 10/2005 | Eliachar |
| 2005/0245928 A1 | 11/2005 | Colleran et al. |
| 2005/0277812 A1 | 12/2005 | Myles |
| 2005/0277928 A1 | 12/2005 | Boschert |
| 2006/0025771 A1 | 2/2006 | Jackson |
| 2006/0036244 A1 | 2/2006 | Spitler et al. |
| 2006/0100622 A1 | 5/2006 | Jackson |
| 2006/0111712 A1 | 5/2006 | Jackson |
| 2006/0111715 A1 | 5/2006 | Jackson |
| 2006/0135852 A1 | 6/2006 | Koros et al. |
| 2006/0142761 A1 | 6/2006 | Landry et al. |
| 2006/0149232 A1 | 7/2006 | Sasing |
| 2006/0149240 A1 | 7/2006 | Jackson |
| 2006/0183978 A1 | 8/2006 | Howard |
| 2006/0189848 A1 | 8/2006 | Penenberg |
| 2006/0200133 A1 | 9/2006 | Jackson |
| 2006/0200185 A1 | 9/2006 | Marchek et al. |
| 2006/0200186 A1 | 9/2006 | Marchek et al. |
| 2006/0206009 A1 | 9/2006 | Von Wald et al. |
| 2006/0241603 A1 | 10/2006 | Jackson |
| 2006/0241618 A1 | 10/2006 | Gasser et al. |
| 2006/0247637 A1 | 11/2006 | Colleran et al. |
| 2006/0247658 A1 | 11/2006 | Pond et al. |
| 2006/0271047 A1 | 11/2006 | Jackson |
| 2006/0271050 A1 | 11/2006 | Piza Vallespir |
| 2006/0276789 A1 | 12/2006 | Jackson |
| 2006/0276792 A1 | 12/2006 | Ensign et al. |
| 2006/0287674 A1 | 12/2006 | Ginn et al. |
| 2007/0016200 A1 | 1/2007 | Jackson |
| 2007/0038033 A1 | 2/2007 | Jones et al. |
| 2007/0049931 A1 | 3/2007 | Justis et al. |
| 2007/0049933 A1 | 3/2007 | Ahn et al. |
| 2007/0055240 A1 | 3/2007 | Matthis et al. |
| 2007/0055241 A1 | 3/2007 | Matthis et al. |
| 2007/0055244 A1 | 3/2007 | Jackson |
| 2007/0073111 A1* | 3/2007 | Bass .............. A61B 17/0206 600/215 |
| 2007/0073112 A1 | 3/2007 | Holmes |
| 2007/0083086 A1 | 4/2007 | LeVahn et al. |
| 2007/0088357 A1 | 4/2007 | Johnson et al. |
| 2007/0090238 A1 | 4/2007 | Justis |
| 2007/0093818 A1 | 4/2007 | Biedermann et al. |
| 2007/0093828 A1 | 4/2007 | Abdou |
| 2007/0100212 A1 | 5/2007 | Pimenta et al. |
| 2007/0106123 A1 | 5/2007 | Gorek et al. |
| 2007/0123862 A1 | 5/2007 | Warnick |
| 2007/0123870 A1 | 5/2007 | Jeon et al. |

(56) References Cited

U.S. PATENT DOCUMENTS

| | | |
|---|---|---|
| 2007/0129608 A1 | 6/2007 | Sandhu |
| 2007/0135817 A1 | 6/2007 | Ensign |
| 2007/0156024 A1 | 7/2007 | Frasier et al. |
| 2007/0161867 A1 | 7/2007 | Fowler et al. |
| 2007/0167949 A1 | 7/2007 | Altarac et al. |
| 2007/0173819 A1 | 7/2007 | Sandlin |
| 2007/0179343 A1 | 8/2007 | Shelokov |
| 2007/0191955 A1 | 8/2007 | Zucherman et al. |
| 2007/0198062 A1 | 8/2007 | Miles et al. |
| 2007/0208227 A1 | 9/2007 | Smith et al. |
| 2007/0208228 A1 | 9/2007 | Pavento et al. |
| 2007/0225568 A1 | 9/2007 | Colleran |
| 2007/0233079 A1 | 10/2007 | Fallin et al. |
| 2007/0233097 A1 | 10/2007 | Anderson et al. |
| 2007/0238932 A1 | 10/2007 | Jones et al. |
| 2007/0270842 A1 | 11/2007 | Bankoski et al. |
| 2007/0299315 A1 | 12/2007 | Geller |
| 2008/0021285 A1 | 1/2008 | Drzyzga et al. |
| 2008/0077136 A1 | 3/2008 | Triplett et al. |
| 2008/0077138 A1 | 3/2008 | Cohen et al. |
| 2008/0114208 A1 | 5/2008 | Hutton et al. |
| 2008/0146881 A1 | 6/2008 | Alimi et al. |
| 2008/0177322 A1 | 7/2008 | Davis |
| 2008/0183044 A1 | 7/2008 | Colleran et al. |
| 2008/0188718 A1 | 8/2008 | Spitler et al. |
| 2008/0249372 A1 | 10/2008 | Reglos et al. |
| 2008/0255567 A1 | 10/2008 | Accordino |
| 2008/0262318 A1 | 10/2008 | Gorek et al. |
| 2009/0012370 A1 | 1/2009 | Gutierrez et al. |
| 2009/0018399 A1 | 1/2009 | Martinelli et al. |
| 2009/0036746 A1* | 2/2009 | Blackwell ........ A61B 17/0206 600/219 |
| 2009/0076333 A1 | 3/2009 | Bjork |
| 2009/0076516 A1 | 3/2009 | Lowry et al. |
| 2009/0105547 A1 | 4/2009 | Vayser et al. |
| 2009/0124861 A1 | 5/2009 | Fetzer |
| 2009/0222046 A1 | 9/2009 | Gorek |
| 2009/0227845 A1 | 9/2009 | Lo et al. |
| 2009/0270916 A1 | 10/2009 | Ramsay et al. |
| 2009/0306480 A1 | 12/2009 | Protopsaltis |
| 2010/0030224 A1 | 2/2010 | Winslow et al. |
| 2010/0081885 A1 | 4/2010 | Wing et al. |
| 2010/0114182 A1 | 5/2010 | Wilcox et al. |
| 2010/0137915 A1 | 6/2010 | Anderson et al. |
| 2010/0217089 A1 | 8/2010 | Farley et al. |
| 2010/0249856 A1 | 9/2010 | Iott et al. |
| 2010/0268036 A1 | 10/2010 | Rothweiler et al. |
| 2010/0298647 A1 | 11/2010 | Black et al. |
| 2010/0298648 A1 | 11/2010 | Gray |
| 2010/0312068 A1 | 12/2010 | Dalton |
| 2010/0331901 A1 | 12/2010 | Iott et al. |
| 2011/0004067 A1 | 1/2011 | Marchek et al. |
| 2011/0022088 A1 | 1/2011 | Forton et al. |
| 2011/0034780 A1 | 2/2011 | Loftus et al. |
| 2011/0130793 A1 | 6/2011 | Woolley et al. |
| 2011/0137130 A1 | 6/2011 | Thalgott et al. |
| 2011/0201897 A1 | 8/2011 | Bertagnoli et al. |
| 2011/0208008 A1 | 8/2011 | Michaeli et al. |
| 2011/0224497 A1 | 9/2011 | Weiman et al. |
| 2011/0245836 A1 | 10/2011 | Hamada |
| 2011/0257487 A1 | 10/2011 | Thalgott et al. |
| 2011/0288594 A1 | 11/2011 | Woolley et al. |
| 2011/0295075 A1 | 12/2011 | Picha et al. |
| 2011/0295328 A1 | 12/2011 | Woolley et al. |
| 2011/0301422 A1 | 12/2011 | Woolley et al. |
| 2011/0301423 A1 | 12/2011 | Koros et al. |
| 2012/0065693 A1 | 3/2012 | Lim et al. |
| 2012/0130180 A1 | 5/2012 | Pell et al. |
| 2012/0232350 A1 | 9/2012 | Seex |
| 2012/0245431 A1 | 9/2012 | Baudouin et al. |
| 2012/0271118 A1 | 10/2012 | White |
| 2012/0271119 A1 | 10/2012 | White |
| 2012/0296171 A1* | 11/2012 | Lovell ................ A61B 17/0206 600/213 |
| 2012/0303034 A1 | 11/2012 | Woolley et al. |
| 2013/0066163 A1 | 3/2013 | White |
| 2013/0123581 A1 | 5/2013 | Fritzinger et al. |
| 2013/0135584 A1 | 5/2013 | Alasaarela et al. |
| 2013/0190575 A1 | 7/2013 | Mast et al. |
| 2013/0245692 A1* | 9/2013 | Hayes ................ A61B 17/708 606/279 |
| 2013/0261401 A1 | 10/2013 | Hawkins et al. |
| 2013/0267786 A1 | 10/2013 | Vayser et al. |
| 2013/0317312 A1 | 11/2013 | Eastlack et al. |
| 2014/0018633 A1 | 1/2014 | Woolley et al. |
| 2014/0024900 A1* | 1/2014 | Capote ............. A61B 17/0206 600/214 |
| 2014/0031874 A1 | 1/2014 | Kucharzyk et al. |
| 2014/0066718 A1 | 3/2014 | Fiechter et al. |
| 2014/0066719 A1 | 3/2014 | Nichter |
| 2014/0114136 A1 | 4/2014 | Ellman |
| 2014/0128682 A1 | 5/2014 | Loebl et al. |
| 2014/0135584 A1* | 5/2014 | Lee .................... A61B 17/0206 600/202 |
| 2016/0074029 A1* | 3/2016 | O'Connell ......... A61B 17/0206 600/213 |
| 2017/0049428 A1* | 2/2017 | Cryder .............. A61B 17/025 |
| 2017/0196597 A1* | 7/2017 | Corbin .............. A61B 17/7049 |
| 2017/0231613 A1* | 8/2017 | Casey ................ A61F 2/30771 600/213 |

FOREIGN PATENT DOCUMENTS

| | | |
|---|---|---|
| CN | 2801073 U | 8/2006 |
| CN | 2936210 U | 8/2007 |
| CN | 201320195 U | 10/2009 |
| CN | 201341901 | 11/2009 |
| CN | 201389044 U | 1/2010 |
| CN | 201389045 U | 1/2010 |
| CN | 201537102 | 8/2010 |
| CN | 201612646 U | 10/2010 |
| CN | 202044299 U | 11/2011 |
| CN | 203458435 U | 3/2014 |
| CN | 203506775 U | 4/2014 |
| DE | 9100113 | 5/1991 |
| DE | 202005018171 | 1/2006 |
| DE | 202009005768 | 7/2009 |
| FR | 2788958 | 8/2000 |
| GB | 2080113 | 2/1982 |
| JP | 10277043 | 10/1998 |
| WO | WO90/04947 | 5/1990 |
| WO | WO98/38921 | 9/1998 |
| WO | WO99/15081 | 4/1999 |
| WO | WO99/17661 | 4/1999 |
| WO | WO2001/006940 | 2/2001 |
| WO | WO2010/020257 | 2/2010 |
| WO | WO2010/057980 | 5/2010 |
| WO | WO2016/025020 | 2/2016 |

OTHER PUBLICATIONS

Dhall et al., "Clinical and Radiographic comparison of Mini-open Transforaminal Lumbar Interbody Fusion With Open Transforaminal Lumbar Interbody Fusion in 42 Patients with Long Term Follow-up," *J. Neurosurg Spine*, 2008, 9: 560-565.

Foley et al, "Minimally Invasive Lumbar Fusion," *Spine*, 2003, 28:S26-S35.

Holly et al., "Minimally Invasive Transformainal Lumbar Interbody Fusion: indications, technique, and Complications," *Neurosurg Focus*, 2006, 20:E6, 5 pages.

Mummaneni and Rodts, "The mini-open transforminal Lumbar Interbody Fusion," *Neurosurgery*, 2005, S7: 256-261.

Ozgur et al., "Minimally Disruptive Decompression and Transforaminal Lumbar Interbody Fusion," *The Spine Journal*, 2006, 6: 27-33.

Ozgur et al., "Minimally-invasive Technique for Transforaminal Lumbar Interbody Fusion (TLIF)," *Eur Spine J*, 2005, 14: 887-894.

Schwender et al., "Minimally invasive transforaminal lumbar interbody fusion (TLIF): technical feasibility and initial results," *J Spinal Disord Tech*. 2005, 18(1):S1-S6.

(56) References Cited

OTHER PUBLICATIONS

International Search Report and Written Opinion from PCT/US2010/002951, dated Mar. 23, 2011, 19 pages.
International Search Report and Written Opinion from PCT/US2015/000084, dated Jul. 3, 2016, 5 pages.

* cited by examiner

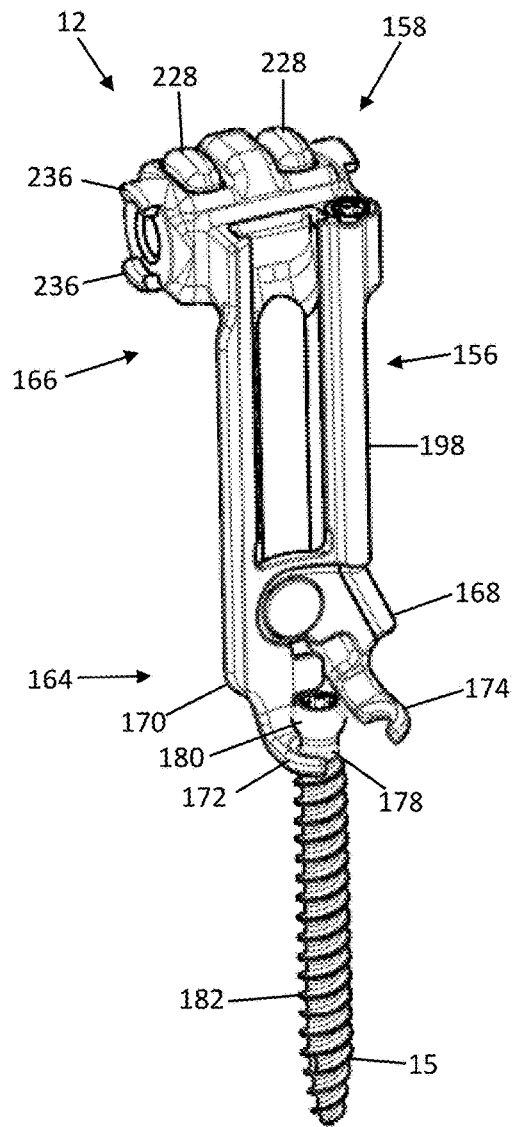
Fig. 12
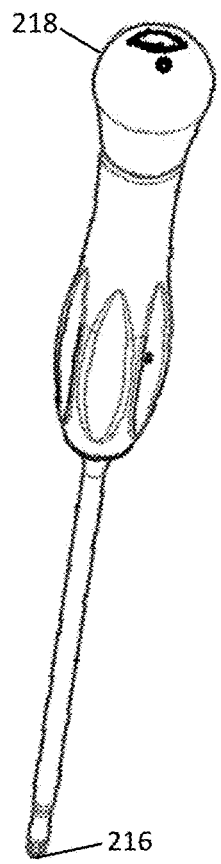
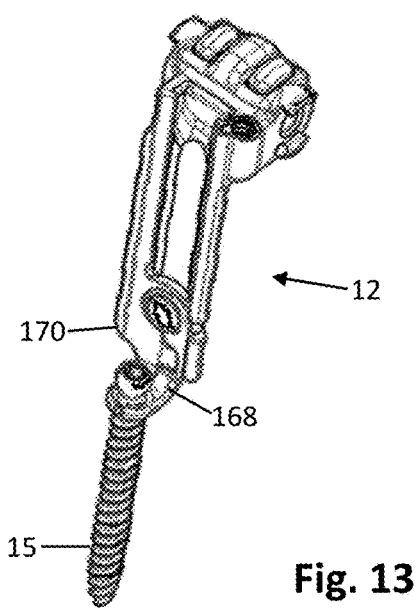
Fig. 13

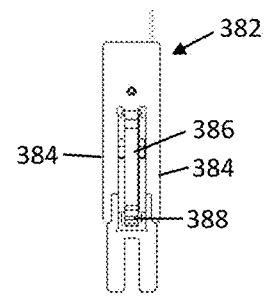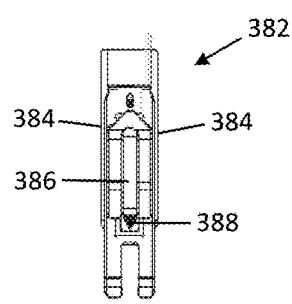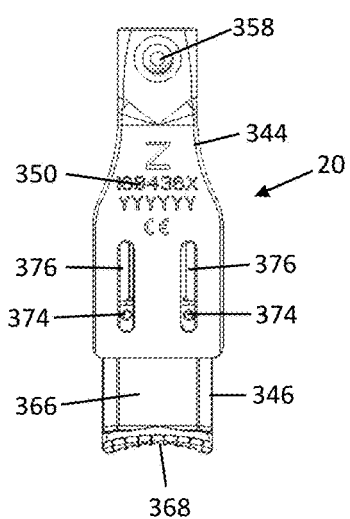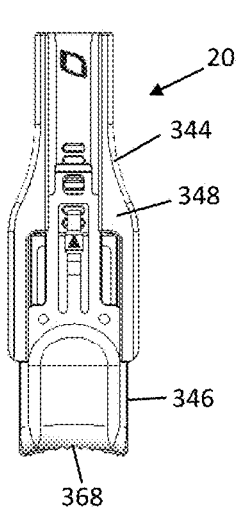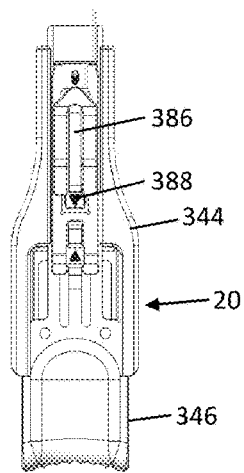
Fig. 23     Fig. 24     Fig. 25
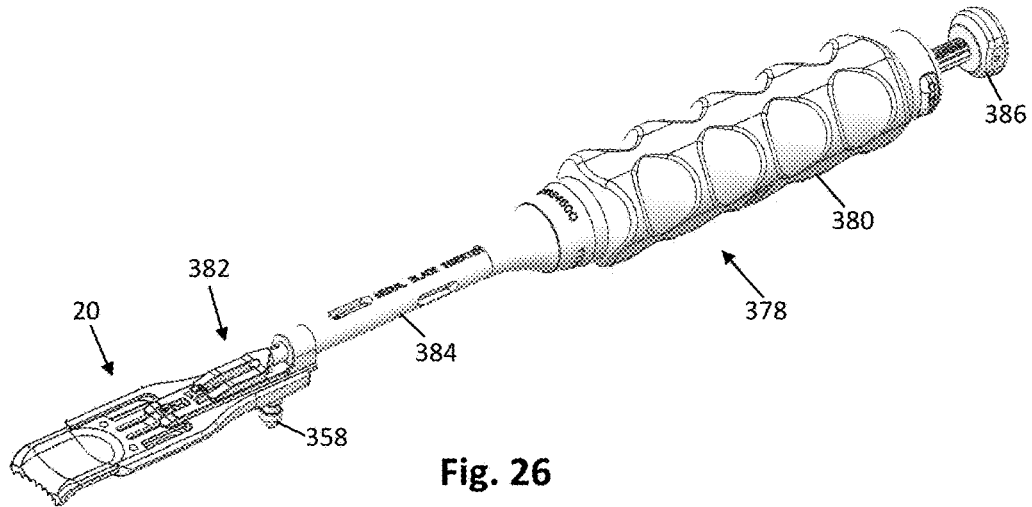
Fig. 26

MINIMALLY DISRUPTIVE RETRACTOR AND ASSOCIATED METHODS FOR SPINAL SURGERY

CROSS-REFERENCES TO RELATED APPLICATIONS

This application is a continuation of U.S. patent application Ser. No. 14/756,198, filed Aug. 14, 2015 (now U.S. Pat. No. 9,795,370), which claims the benefit of priority under 35 U.S.C. 119(e) from U.S. Provisional Patent Application Ser. No. 62/036,776, filed on Aug. 13, 2014, and U.S. Provisional Patent Application Ser. No. 62/201,739, filed on Aug. 6, 2015, the entire contents of which are each hereby expressly incorporated by reference into this disclosure as if set forth fully herein.

FIELD

This application describes surgical instruments and methods for providing access to a surgical target site for the purpose performing minimally invasive spinal fusion across one or more segments of the spinal column.

BACKGROUND

Spinal fixation constructs are utilized to provide stability to the spine. Most often the fixation construct is used as an adjunct to fusion surgery during which adjacent vertebrae are prepared to facilitate bone growth between them, thereby eliminating motion between the vertebrae. Because motion between the vertebrae tends to inhibit bone growth, the fixation constructs are employed to prevent motion so that bone can grow and achieve a solid fusion. When the position of one or more vertebrae must be adjusted to restore a more natural alignment of the spinal column, the fixation construct also serves to maintain the new alignment until fusion is achieved. Fixation constructs of various forms are well known in the art. Most commonly, the fixation construct is a plate anchored to the anterior column with multiple bone anchors or a posterior fixation construct including multiple anchors and a connecting rod anchored to the posterior elements of the spine. For a posterior fixation construct the anchors (typically pedicle screws) are anchored into the pedicles of each vertebra of the target motion segment. The anchors are then connected by a fixation rod that is locked to each anchor, thus eliminating motion between the adjacent vertebrae of the motion segment. The posterior fixation construct may be applied unilaterally or bilaterally. Additionally the posterior fixation construct may be applied across multiple levels or motion segments.

The fixation anchors utilized in posterior fixation constructs generally include an anchor portion and a rod housing. The rod housing includes a pair of upstanding arms separated by a rod channel in which the fixation rod is captured and locked. When constructing the posterior fixation construct the surgeon must align and seat the rod in the rod channel. This can be a challenge, particularly when one or more of the vertebrae to be connected is out of alignment leaving the associated anchor offset vertically and/or horizontally from the remaining anchor(s) of the construct. Constructing the posterior fixation construct under minimally invasive access conditions (e g minimizing overall incision length and muscle stripping as compared to traditional open procedures) also increases the difficulty of aligning the rod with the rod channel of the anchor.

The instruments, tools, and techniques described herein are directed towards reducing these challenges and others associated with posterior spinal fixation.

SUMMARY

The present application describes a tissue retractor assembly and related instruments and methods for performing minimally invasive spinal surgery, for example transforaminal lumbar interbody fusion (TLIF) surgery. The tissue retractor is used in conjunction with bone anchors to establish and maintain an operative corridor to the surgical target site. More particularly, the retractor anchors to the anatomy (e.g. pedicles) adjacent the surgical target site (e.g. intervertebral disc) to both anchor the exposure and define the boundaries with anatomical landmarks to orient the surgeon and facilitate navigation. Once this access corridor has been established, the disc space and vertebral endplates may be prepared, one or more interbody implants may be inserted into the disc space, and spinal rods may then be used to align and compress or reduce the construct.

The retractor assembly includes an access retractor body, first and second anchor blades, a secondary retractor, and a secondary blade. The first and second anchor blades capture a portion of bone anchors to anchor the retractor to the anatomy. When fully assembled and in operation, the access retractor body, anchor blades, and secondary blade establish and define a working corridor through which access to the surgical target site is achieved. This working corridor is expandable in a caudal-cranial direction as well as medially.

The access retractor body includes first and second racks, and left and right arms. The first and second anchor blades are removably attached to the left and right arms, respectively. In use during a TLIF procedure described herein, the retractor assembly may be positioned relative to the patient such that the access retractor body is located laterally of the wound (away from the patient's body). This advantageously positions the main part of the retractor outside of the fluoroscopy window. Although the first anchor blade is described herein as being removably attached to the left arm and the second anchor blade is described as being removably attached to the right arm it should be understood that the first and second anchor blades are virtually identical in form and function, and therefore are interchangeable.

The access retractor body includes a base having a pair of channels extending laterally therethrough. The channels are sized and dimensioned to receive the first and second racks therein, and are separated from one another by a distance sufficient to enable placement of a pinion to control translation of the racks. A thumb tab is rotatable to control the directional translation of the racks. By way of example only, rotating the thumb tab in a clockwise direction "opens" the retractor by simultaneously causing the first rack to translate toward the left (relative to the retractor) and the second rack to translate toward the right. This translation in turn causes the retractor blades to move in the same direction as the racks, controlling the size of the surgical wound. Thus, if the access body is positioned laterally of the surgical wound away from the patient's body, the first retractor blade will translate in a caudal direction, and the second retractor blade will translate in a cranial direction. A pawl, moveable from a first (e.g. "unlocked") position to a second (e.g. "locked") position is provided to enable the user to lock the retractor in an open position during use. The pawl includes a wedge that is configured to engage the teeth of the second rack and directly prevent translation of the second rack when the pawl is in the second "locked" position. This also indirectly prevents translation of the first rack, effectively locking the retractor in an "open" configuration. When the pawl is in the first "unlocked" position, the wedge is disengaged from the teeth, allowing free translation of the racks. A pinion is positioned between the racks and is mechanically coupled with the thumb tab such that turning the thumb tab causes the pinion to rotate, which in turn causes the racks to translate. A coiled spring is provided to bias the pawl in a locked position, thereby passively allowing the retractor to open freely. A clip is provided on the underside of the base and engages a post on the thumb tab to secure the construct together. The access retractor body further includes an articulating arm attachment to enable attachment to an articulating arm to secure the retractor assembly to the patient's bedrail (or other static, rigid mounting location) during use.

By way of example only, the racks are generally rectangular elongated members having a plurality of teeth distributed on one side of each of the racks. The teeth are configured to interact with the pinion to allow controlled translation of the arms.

The left arm includes a proximal segment and a distal segment. The proximal segment includes a first aperture and a second aperture. The first aperture is configured to fixedly receive the first rack such that the first rack and proximal segment are generally perpendicular to one another. Thus, translation of the first rack in either direction causes a corresponding movement of the left arm in the same direction. The second aperture is configured to slidingly receive the second rack therethrough such that the second rack is able to pass through the proximal segment unencumbered in either direction during translation.

The distal segment is connected to the proximal segment and is configured to releasably engage the first anchor blade. The distal segment includes a generally cylindrical housing having a distal face. The distal face includes a central post protruding distally from the center of the distal face and a pair of opposing recesses positioned on the perimeter of the distal face on either side of the central post. The central post is configured to mate with the attachment aperture of the anchor blade to securely attach the anchor blade to the left arm. The central post is generally cylindrical and includes a tapered leading end and a circumferential recess positioned between the leading end and the distal face. The housing is able to rotate, thus causing the anchor blade to rotate and effect tissue distraction. This rotation is independent of the second anchor blade, and controlled by a splay unit. The splay unit includes a flange extending laterally away from the housing, a threaded jack screw, and a cap. The jack screw is pivotably secured to the flange via a post. The cap includes a threaded central aperture and an engagement recess for receiving a distal end of an activation instrument (not shown) such as a T-handle (for example). As the cap is rotated by the activation instrument, it translates (in either direction depending on the direction of rotation of the instrument) along the jack screw. This causes the jack screw to pivot about the pin, which in turn causes the cap to transfer a torque to the housing, and more specifically the opposing recesses. As described below, the recesses engage with the flanges of the anchor blade, thus causing the anchor blade to pivot either outward or inward depending on the rotation of the activation instrument. The splay unit allows for continuously variable blade splay and will actuate for example to allow for −20° to 25° (up to 45° total) of angular splay.

The right arm includes a proximal segment and a distal segment. The proximal segment includes an aperture configured to fixedly receive the second rack such that the second rack and proximal segment are generally perpendicular to one another. Thus, translation of the second rack in either direction causes a corresponding movement of the right arm in the same direction.

The distal segment is connected to the proximal segment and is configured to releasably engage the second anchor blade. The distal segment includes a generally cylindrical housing having a distal face. The distal face includes a central post protruding distally from the center of the distal face and a pair of opposing recesses positioned on the perimeter of the distal face on either side of the central post. The central post is configured to mate with the attachment aperture of the anchor blade to securely attach the anchor blade to the right arm. The central post is generally cylindrical and includes a tapered leading end and a circumferential recess positioned between the leading end and the distal face. The housing is able to rotate, thus causing the anchor blade to rotate and effect tissue distraction. This rotation is independent of the first anchor blade, and controlled by a splay unit. The splay unit includes a flange extending laterally away from the housing, a threaded jack screw, and a cap. The jack screw is pivotably secured to the flange via a post. The cap includes a threaded central aperture and an engagement recess for receiving a distal end of an activation instrument such as a T-handle (for example). As the cap is rotated by the activation instrument, it translates (in either direction depending on the direction of rotation of the instrument) along the jack screw. This causes the jack screw to pivot about the pin, which in turn causes the cap to transfer a torque to the housing, and more specifically the opposing recesses. As described below, the recesses are engaged to the flanges of the anchor blade, thus causing the anchor blade to pivot either outward or inward depending on the rotation of the activation instrument. The splay unit allows for continuously variable blade splay and will actuate for example to allow for −20° to 25° (up to 45° total) of angular splay.

Optionally, the access retractor body may be provided with moveable arms. Providing the retractor with moveable arms may allow for the access retractor body to be raised off the patient's skin level to avoid anatomical challenges that might otherwise cause the access retractor body to dig into the patient's skin, as well as to potentially maneuver the access retractor body out of the fluoroscopy zone. Each moveable arm includes a middle segment positioned between proximal and distal arm segments such as those described above. For example, the left moveable arm includes a proximal segment, a middle segment, and a distal segment. The right moveable arm includes a proximal segment, a middle segment, and a distal segment. In the interest of expediency, the moveable arm feature will be described in detail with respect to one arm only. However it is to be understood that the moveable arms are virtually identical to one another and thus any feature disclosed may be attributed to either moveable arm.

The proximal segment of the moveable arm includes all of the features previously described in relation to the proximal segment of the left arm described above, and further includes a pivot member extending distally from the proximal segment, the pivot member configured to be received within a proximal recess formed in the proximal end of the middle segment. The distal segment of the moveable arm includes all the features previously described in relation to the distal segment of the left arm described above, and further includes a pivot member extending proximally from the distal segment, the pivot member configured to be received within a distal recess formed in the distal end of the middle segment.

The middle segment is pivotally connected to both the proximal segment and the distal segment. The middle segment has a proximal end including a proximal recess configured to receive the pivot member of the proximal segment. A pin extends through the proximal end and pivot member and provides an axis about which the middle segment pivots relative to the proximal segment. The middle segment further has a distal end including a distal recess configured to receive the pivot member of the distal segment. A pin extends through the distal end and pivot member and provides an axis about which the distal segment pivots relative to the middle segment. The middle segment further includes a friction recess positioned in the middle of the middle segment. The friction recess houses a friction element comprising a pair of friction pins separated by a spring. The spring exerts a force equally on the friction pins that in turn exerts a frictional force on the pivot members. Thus, the friction element allows movement of the middle segment relative to the proximal and distal segments in the presence of sufficient force to overcome the friction. In the absence of such a force, the friction element operates to maintain the position of the middle segment relative to the proximal segment and distal segments. The double hinge creates a flexible arm construct such that the arms can pivot about and adjust to eliminate caudal-cranial blade skew issues (encountered when facing difficult patient anatomy).

The first and second anchor blades are virtually identical to each other in form and function and therefore all features disclosed herein with regard to one anchor blade may be attributable to the other anchor blade as well. Generally, the anchor blade has a blade portion extending from a coupler. The blade portion has an interior face and an exterior face. The exterior face is generally smooth and rests against the soft tissue during use. The anchor blade is configured to pivot to effect distraction as discussed previously. The blade portion has a distal end and a proximal end.

The distal end includes an integral pivot arm such that the distal end is divided into a static arm and a pivot arm. The distal end of the static arm includes a static foot extending therefrom and the distal end of the pivot arm includes a pivot foot extending therefrom. When together in a closed position, the pivot foot and static foot act in concert to form a capture element (e.g. divided ring) having a center aperture dimensioned to receive a neck of the bone anchor (which also includes a head and a threaded shank). A contact surface on the static foot and a contact surface on the pivot foot interface with the generally spherical outer surface of the head of the bone anchor to form a polyaxial joint between the bone anchor and anchor blade. The contact surfaces may each have any shape capable of enabling such a polyaxial relationship, including but not limited to angled, rounded, and/or spherically concave. The pivot arm is pivotably attached to the distal portion of the anchor blade by a pin that extends through a pivot aperture on the proximal end of the pivot arm and a corresponding pivot aperture on the distal portion of the anchor blade. The pivot arm rotates in a plane parallel to the width of the anchor blade such that the pivot foot can be separated from the static foot to permit passage of the screw shank, allowing the anchor blade to be disengaged from the bone anchor after tulip coupling. A lateral recess is formed in the pivot foot and is configured to receive a stabilization flange therein. The stabilization flange extends away from the static foot into the lateral recess to ensure the pivot foot remains in the desired plane of motion.

The static arm includes an inward lateral extension which interdigitates with a cutout in the pivot arm which provides additional strength to resist a force applied to the ring.

The anchor blade further includes an enclosed channel positioned on one side of the anchor blade and extending the length of the blade. A locking shaft extends through the enclosed channel and engages the pivot arm to maintain the pivot foot (and capture element) in a closed position. This engagement is controlled by an actuator, for example a setscrew, that is engaged by a user to actuate the locking shaft. The setscrew includes a threaded body, a distal shelf, and a tool recess. The threaded body is generally cylindrical and configured to engage a threaded recess on the proximal end of the anchor blade. The distal shelf interacts with a proximal tab on the locking shaft in such a way that when the setscrew is rotated, accordingly the distal shelf exerts a downward force on the proximal tab, causing the locking shaft to advance distally through the enclosed channel and engage the pivot arm. A capture ring is provided to prevent the setscrew from backing out of the threaded recess. The tool recess is configured to receive a distal end of a driver that is used to actuate the setscrew. Although described herein as a setscrew, the actuator may be any element that a user may use to cause movement of the locking shaft, including but not limited to a cam mechanism and the like. The anchor blade further includes a track that slidably receives various instruments (e.g. shank/blade inserter, tulip inserter) and light cables.

The coupler is integrally formed with the proximal portion of the anchor blade and provides a spring-loaded quick connect and release mechanism for engagement with the central post of the left arm (and/or the central post of the right arm) described above. It should be understood that the anchor blades are interchangeable in that either anchor blade may be used with either the left arm or right arm. Therefore, only the interaction between one anchor blade and the left arm is described in detail herein, however all features herein described also apply to the interaction between the other anchor blade and the right arm. The coupler has a proximal half and a distal half. For the purpose of this disclosure, the proximal half is defined as the portion of the coupler that engages with left retractor arm, and the distal half is defined as the portion of the coupler that engages with the secondary retractor (or the right retractor arm, if attached thereto). The proximal half and distal half of the coupler are identical and as such the various features common to both halves will be assigned the same reference numerals for clarity.

The coupler includes a housing and a pair of buttons. The housing includes a proximal face on the proximal end (and an identical distal face on the distal end), an attachment aperture extending through the proximal face, a pair of button apertures, and an interior lumen. The proximal face includes a pair of flanges extending proximally from the proximal face. When the anchor blade is mated to the left arm, the proximal face flushly interfaces with the distal face of the left arm, and the flanges engage with the recesses formed in the distal face of the left arm to enable pivoting of the anchor blade in response to user activation of the splay unit. The attachment aperture receives the central post of the left arm therethrough such that the central post can extend into the interior lumen of the housing. The button apertures are configured to allow passage of the buttons into the interior lumen. The buttons each have a top surface, a through-hole, a lower ridge, and a bottom post. The top surface is generally rounded to maintain a low profile and cause minimal disruption to surrounding anatomy during use, and is provided as a user engagement surface. The through-hole receives the central post therethrough. The lower ridge is configured to nest within the circumferential recess of the central post to prevent egress of the central post during use. The bottom post centers a spring which biases the lower ridge into the circumferential recess. During coupling of the anchor blade and the left arm, he tapered leading end of the central post enables the central post to overcome the bias and advance until the lower ridge is aligned with the circumferential recess, at which point the spring causes the lower ridge to snap into circumferential recess. To release the blade, the user presses downward on the top surface, which forces the lower ridge out of the circumferential recess, enabling removal of the central post. The buttons are secured to the coupler via pins that nest in recesses on the buttons. The coupler may also include alignment markings that act in concert with alignment markings on the arms to provide visual feedback to a user that sufficient distraction is achieved.

The anchor blades transmit torque efficiently to the bone anchor (e.g. for compression/distraction) without any loss of polyaxial (tulip) motion. The anchor blades are reusable. The pivot foot of the anchor blade allows for top down loading of large screws where the shank thread diameter is larger than the diameter of the shank head. The pivot foot will allow a polyaxial tulip to be loaded in top down approach without entrapping the anchoring point of the anchor blades.

The secondary (e.g. medial) retractor can attach to an assembled retractor and has a self-locking mechanism. The secondary retractor is attachable to the coupler of the anchor blade and comprises a retraction assembly and a blade assembly. The secondary retractor allows for further connection to a secondary (e.g. medial) blade and drives further access to the spine medially with many degrees of freedom. For example, the secondary retractor may provide for medial retraction, medial splay, caudal-cranial pivoting and caudal-cranial translation. The retraction assembly provides medial retraction and comprises a housing, a threaded shaft, and a perpendicular gear comprising an actuating gear and a translation gear, rendering fine resolution. The housing has an interior lumen through which the threaded shaft extends and within which the perpendicular gear is contained. The actuating gear includes a tooth portion and an engagement recess. The engagement recess extends through an aperture formed in the housing and provides an engagement element for an actuator tool. The housing has a circumferential recess configured to accept a snap ring. The actuating gear is secured to the housing via the snap ring and a grooved retention washer. The translation gear is oriented perpendicularly relative to the actuating gear. The translation gear includes a tooth portion, a post, and a threaded interior lumen. The tooth portion engages the tooth portion of the actuating gear and causes rotation of the translation gear when the actuating gear is rotated. The post fits within a retaining ring, which has a circumferential recess configured to receive a snap ring therein. The snap ring also fits within groove formed within the interior lumen to secure the translation gear to the housing. A ball bearing race is provided to prevent galling between the gears during use.

The threaded shaft mates with the threaded lumen of the translation gear. As the translation gear rotates, the threaded shaft is caused to translate in either a medial or lateral direction, depending on the direction of the rotation. The threaded shaft further includes a proximal end that is virtually identical in structure and function to the distal face of the first arm described above. To wit, the proximal end includes a proximal face, a central post protruding distally from the center of the proximal face and a pair of opposing recesses positioned on the perimeter of the proximal face on either side of the central post. The central post is configured to mate with the attachment aperture of the anchor blade (or anchor blade) to securely attach the anchor blade to the left arm. The central post is generally cylindrical and includes a tapered leading end and a circumferential recess positioned between the leading end and the proximal face. These features interact with the quick release mechanism of the anchor blade described above in a manner that is identical to the manner in which the corresponding structure of the left retractor arm interacts with the quick release mechanism of the anchor blade, and thus a repeat discussion is unnecessary. It should be noted, however that in the example disclosed above in which the anchor blade is attached to the left retractor arm via the proximal end of the coupler, the secondary retractor may be contemporaneously attached to the distal end of the coupler.

The blade assembly extends generally perpendicularly from the retraction assembly and includes a quick release housing and a splay unit. The quick release housing includes an attachment aperture for receiving the attachment post of the secondary blade and a button that is biased with a spring. The quick release housing is identical to form and function to the same feature described above in relation to the coupler, and thus a detailed description of the like features need not be repeated. Similarly, the splay unit is identical in form and function to the splay unit of the left arm, and thus a detailed description of the like features need not be repeated. It should be noted however that the splay unit allows for continuously variable blade splay and will actuate for example to allow for up to 40° of angular splay.

An alternative secondary retractor may be provided that differs from the secondary retractor described above in that the alternative secondary retractor attaches to both the left retractor arm (via one anchor blade) and the right retractor arm (via the other anchor blade). The alternative secondary retractor is attachable to the coupler of the first anchor blade and a corresponding coupler of the second anchor blade. The alternative secondary retractor comprises a retraction assembly, a blade assembly, and a second attachment unit. The alternative secondary retractor allows for further connection to a secondary (e.g. medial) blade and drives further access to the spine medially with many degrees of freedom. For example, the alternative secondary retractor may provide for medial retraction, medial splay, caudal-cranial pivoting and caudal-cranial translation. The retraction assembly is identical to the retraction assembly described above. A crossbar extends generally perpendicularly from the retraction assembly and terminates at the second attachment unit. The blade assembly is positioned on the crossbar between the retraction assembly and the second attachment unit. The blade assembly includes a quick release housing and a splay unit. The quick release housing includes an attachment aperture for receiving the attachment post of the secondary blade and a button that is biased with a spring. The quick release housing is identical in form and function to the same feature described above in relation to the coupler, and thus a detailed description of the like features need not be repeated. Similarly, the splay unit is identical in form and function to the splay unit of the left arm, including a captured jackscrew and a cap. It should be noted however that the splay unit causes pivoting of the quick release housing (and thus the secondary blade) but does not cause rotation of the crossbar or the second attachment unit. The splay unit allows for continuously variable blade splay and will actuate for example to allow for up to 40° of angular splay.

The second attachment unit includes a base, an extension, and an attachment post. The attachment post is generally cylindrical and includes a tapered leading end and a circumferential recess positioned between the leading end and the extension. These features interact with the quick release mechanism of the anchor blade described above in a manner that is identical to the manner in which the corresponding structure of the left retractor arm interacts with the quick release mechanism of the anchor blade, and thus a repeat discussion is unnecessary.

The secondary retractor blade includes proximal track portion and a distal blade portion. The proximal track portion has an inner face and an outer face. The inner face includes a recess for nesting with at least a portion of the distal blade portion. The track portion further includes a track for receiving a light cable (for example) and a plurality of ratchet apertures positioned along the track portion proximally of the recess. The outer face includes an attachment post extending generally perpendicularly away from the outer face. The attachment post is identical in form and function to the central post of the left retractor arm, and interacts with the quick release mechanism of the secondary retractor in the same manner that the central post of the left retractor arm interacts with the quick release mechanism of the coupler. The distal blade portion includes a blade and a guide flange. The blade includes an inner face, an outer face, and a serrated foot at the distal tip. The inner face may include a slightly concave surface. The serrated foot curves toward the outer surface and helps minimize tissue creep effect. The guide flange engages with the track to couple the distal blade portion to the proximal track portion. The guide flange further includes a cantilever ratcheting mechanism having a proximal end that interacts with the apertures to maintain a desired length of the blade construct. Guide pins extend through pin apertures in the distal blade portion and into guide tracks to ensure the distal blade portion maintains proper alignment during use.

To use, the secondary blade may be coupled to a blade inserter. The blade inserter includes a proximal handle and a distal tip separated by an elongated shaft. The proximal handle includes a release button extending proximally therefrom. The distal tip includes side edges that mate with the track on the proximal track portion to couple the secondary blade to the blade inserter. The distal tip further includes a cantilever ratcheting mechanism having a distal end that interacts with the apertures to maintain a secure hold on the secondary blade.

To use the secondary blade, first the blade is coupled to the inserter as described above. It should be noted that the distal blade portion should be initially placed in a fully extended position (i.e. positioned such that the distal end of the cantilever ratchet mechanism engages the distal-most ratchet aperture on the proximal track portion. The secondary blade is then manually advanced into the surgical target site by the user. The distal tip of the blade may be placed first with haptic feedback in the desired location and then subsequently compressed and connected to the secondary retractor. Optionally, the user may use the secondary blade like a Cobb instrument to elevate the tissue at the distal tip. This simultaneously allows the blade to lengthen appropriately while staying compressively locked. Blade compression is achieved as follows: once the blade engages with an anatomical structure (e.g. soft tissue, bone), the distal end will stop moving. If the user continues to apply a downward force on the insertion instrument, the cantilever ratcheting mechanism will cause the distal end to vacate one ratchet aperture for the next proximal ratchet aperture and so on, until the desired blade compression is achieved. The user than maneuvers the secondary blade so that it connects to the secondary retractor via the features described above. If desired, the user may affect blade splay while the inserter is still attached, or after it has been disengaged. Further blade compression may occur during blade splay. Once the secondary blade has been inserted, the release button may be used which causes the cantilever ratcheting mechanism to re-engage the ratchet apertures while providing downward force to the distal blade, enabling the inserter to be removed from the surgical wound while contemporaneously allowing the secondary blade to maintain an extended state. By way of example, the distal blade portion of the secondary blade may be made of a titanium material selection that provides for intraoperative fluoroscopy radiolucency.

By way of example, one method of using the tissue retractor assembly of the present disclosure is in a TLIF procedure. A beneficial feature of the retractor assembly described herein is that the bone anchor may be coupled to the anchor blades prior to introduction into the surgical target site. This is done by first unlocking the pivot foot, inserting the neck of the bone anchor into the center aperture, and then relocking the pivot foot as described above. The bone anchor is now coupled to the anchor blade, and now may also be coupled to a driver instrument prior to advancement through the operative corridor. Once the patient has been properly positioned, the target area has been identified and exposure has been established, the bone anchors may be placed in the first target sites. After tapping the target pedicles, the coupled bone anchor, anchor blade, and inserter may be advanced over the K-wire to the target site. The anchor is driven into the bone until either the distal end of the driver or the anchor blade bottoms out on bone. The K-wire may be removed after the threaded shank enters the posterior part of the vertebral body. These steps may be repeated to place a second anchor blade coupled with a bone anchor in a pedicle of an adjacent vertebral body.

At this point the access retractor body can be attached to the anchor blades on either side (e.g. medial or lateral), however it can be advantageous to attach the access retractor body to the lateral side of the anchor blades (i.e. away from the patient's spine) so to increase visibility of the target area under fluoroscopy. As described above, the access retractor body is connected to the anchor blades by inserting the central posts into the quick-connect couplers of the anchor blades. An audible click will sound when the access retractor body is properly engaged to the blades. At this point the retractor assembly may be attached to a articulating arm (for example) using the articulating arm attachment. Positioning the retractor assembly so that the anchor blades are parallel to the disc space ensures the proper medial exposure trajectory is achieved.

If distraction is desired, the anchor blade may be splayed by using a T-handle (for example) to actuate the cap of the splay unit on the left retractor arm as described above. Similarly, the anchor blade may be independently splayed using a T-handle (for example) to actuate the cap of the splay unit of the right retractor arm. Rotation of the T-handles in a clockwise direction causes the blades to splay outward. Since the blades are coupled to the pedicle bones via the bone anchors, this will also cause distraction of the disc space. The coupler may include alignment markings that act in concert with alignment markings on the arms to provide visual feedback to a user that sufficient distraction is achieved. Once proper alignment has been achieved, the user may rotate the thumb tab (or for example a T-handle, if desired) in a clockwise direction to open the retractor and provide soft tissue retraction and initial visualization of the working corridor.

Once adequate soft tissue retraction as been achieved, a single-engagement secondary retractor or a dual-engagement secondary retractor may be added to enable medial retraction. The single-engagement secondary retractor is attached by inserting the central post into the distal half of the coupler of the anchor blade. An audible click will sound when the secondary retractor has been properly engaged to the anchor blade. The dual-engagement secondary retractor is attached by inserting the central post into the distal half of the coupler of the anchor blade, and by inserting the attachment post of the second attachment unit into the distal half of the coupler of the anchor blade. Audible clicks will sound when the secondary retractor has been properly engaged to each of the anchor blades. A secondary blade is then selected and attached to an inserter, and then attached to the secondary retractor. Once the adequate medial blade retraction and splay has been achieved the release button is pressed on the inserter to release the secondary blade from the inserter.

From this point the additional steps of the TLIF procedure is carried out at this level including facetectomy, decompression, further distraction (optionally), disc and endplate preparation, and interbody implant insertion. In preparation for rod insertion, a tulip head (not shown) is attached to the bone anchor head while the anchor blades are engaged with the bone anchor at each vertebral level. The rods may also be placed and locked down while the anchor blades are attached. Once the rod construct is sufficiently in place, the pivot foot is unlocked by rotating the setscrew counterclockwise, which causes the locking shaft to retreat proximally through the enclosed channel and thus disengage the pivot arm. The pivot arm is allowed to move freely, enabling the anchor blade to be dissociated from the bone anchor and removed from the working channel. The second anchor blade may be removed from the working channel in the same manner as the anchor blade, and the operative wound is closed, completing the procedure.

For multi-level TLIF procedures, the retractor assembly may be used in a "marching technique" to reduce the number of times the pedicles have to be targeted. For example, for a two-level TLIF (involving three adjacent vertebrae), coupled anchor-blade-inserters are placed in each target pedicle (i.e. three blades in total at two adjacent levels). The procedure is performed as described above with relation to one of the levels while the third anchor blade is unattached to anything (except the implanted bone anchor). After the TLIF is completed at the first level, the retractor assembly is removed except for the anchor blades. The first anchor blade is left attached to the bone anchor. The middle blade is rotated 180° and then reconnected to the access retractor body (the other retractor arm), along with the third anchor blade. The TLIF is performed at the second level. Once the tulips are down the rod can be placed connecting all 3 levels and the procedure can then be finished.

An alternative anchor blade configured for use with the tissue retractor assembly described herein is provided. The alternative anchor blade is similar to the previously described anchor blade except for the quick-connect mechanism. Generally, the present anchor blade has a blade portion extending from a coupler. The blade portion is identical in form and function to the blade portion of the anchor blade described above, and therefore all features disclosed with respect to blade portion of the previously described anchor blade are attributable to blade portion of the presently described anchor blade as well, rendering a repeat disclosure unnecessary.

The coupler is integrally formed with the proximal portion of the anchor blade and provides an alternative spring-loaded quick connect and release mechanism for engagement with the central post of the left arm (and/or the central post of the right arm) described above. It should be understood that the present anchor blades and are interchangeable in that the anchor blade may be used with either the left arm or right arm. Therefore, only the interaction between the anchor blade and the left arm is described in detail herein, however all features herein described also apply to the interaction between the anchor blade and the right arm. The coupler has a proximal half and a distal half. For the purpose of this disclosure, the proximal half is defined as the portion of the coupler that engages with left retractor arm, and the distal half is defined as the portion of the coupler that engages with the secondary retractor (or the right retractor arm, if attached thereto). The proximal half and distal half of the coupler are identical.

The coupler includes a housing and a pair of release buttons. The housing includes a proximal face on the proximal end (and an identical distal face on the distal end), an attachment aperture extending through the proximal face, a trigger aperture extending through the proximal face below the attachment aperture, a pair of button recesses, and an interior lumen. The proximal face includes a pair of flanges extending proximally from the proximal face. When the anchor blade is mated to the left arm, the proximal face flushly interfaces with the distal face of the left arm, and the flanges engage with the recesses formed in the distal face of the left arm to enable pivoting of the anchor blade in response to user activation of the splay unit. The attachment aperture receives the central post of the left arm therethrough such that the central post can extend into the interior lumen of the housing. The button recesses are configured to provide a low profile nesting location for the release buttons when the anchor blade is in a "ready" state (e.g. prior to coupling with a left arm). The button recesses each have a spring recess positioned therein for housing one end of the button springs. The release buttons each have a top surface, a bottom surface, and a locking flange extending from the bottom surface. The top surface is generally rounded to maintain a low profile and cause minimal disruption to surrounding anatomy during use, and is provided as a user engagement surface. The bottom surface includes a spring recess for housing the other end of the button spring. The locking flange extends from the bottom surface and includes a through-hole and a trigger slot extending below the through-hole. The through-hole receives the central post therethrough. The rim of the through-hole is sized and configured to nest within the circumferential recess of the central post to prevent egress of the central post after the central post has been fully inserted into the lumen (thereby locking the anchor blade to the left arm). The trigger slot is divided into a first part and a second part. The first part has a width dimension that is complementary to the diameter of the middle portion of the trigger button. The second part has a width dimension that is complementary to the diameter of the end portion of the trigger button. The coupler further includes a spring-loaded trigger button that is at least partially housed, along with a trigger spring, within a trigger lumen positioned underneath the interior lumen. The trigger button has a base, a middle portion having a diameter that is smaller than the diameter of the base, an end portion having a diameter that is smaller than the diameter of the middle portion, and an end cap having a diameter that is greater than the diameter of the end portion.

In a detached or "ready" state (e.g. prior to coupling with the left arm), the trigger spring exerts an outward force on the base of the trigger button, which biases the middle portion of the trigger button through the trigger aperture and at least partially into the first part (i.e. wider part) of the trigger slot. This pulls the release button downward so that the release button is nested within the button recess and the button springs are compressed. In this state, the attachment aperture of the housing is aligned with the through-hole of the release button, thereby allowing the insertion of the central post into the interior lumen to enable coupling of the anchor blade and the left arm. During coupling of the anchor blade and left arm, as the central post is advanced through the through-hole and attachment aperture and into the interior lumen. As this advancement is occurring, the distal face of the left arm encounters the trigger button and exerts an inward force on the end cap. This inward force is greater than the outward force exerted by the trigger spring, and the trigger button is urged into the trigger lumen. As the trigger button is pushed further into the trigger lumen, the middle portion is pushed entirely out of the first part of the trigger slot, leaving only the end portion in the trigger slot. The button spring is thus allowed to release energy by exerting an upward force on the bottom surface of the release button. This force snaps the release button up, causing the end portion of the trigger button to snap into the second part of the trigger slot while simultaneously causing the rim of the through-hole to snap into the circumferential recess of the central post to prevent egress of the central post after the central post has been fully inserted into the lumen (thereby locking the anchor blade to the left arm). The forcible movement of the release button makes the metal-on-metal contact between the rim and the circumferential recess audible, providing feedback to the user in the form of an audible "click" to indicate that the anchor blade is secured to the retractor arm. In this "locked" state, the attachment aperture and through-hole are no longer in alignment. To release the anchor blade, the user pushes the release button. This brings the attachment aperture and through-hole back into alignment while simultaneously evicting the rim from the circumferential recess, enabling the central post to be removed from the coupler.

According to another embodiment, a third example of a secondary retractor that can attach to the tissue retractor assembly is disclosed herein. The third example secondary retractor is attachable to the coupler of the anchor blade (e.g. any of the anchor blade embodiments disclosed herein) and comprises a retraction assembly and a blade assembly. The present secondary retractor allows for further connection to a secondary (e.g. medial) blade and drives further access to the spine medially with many degrees of freedom. For example, the present secondary retractor may provide for medial retraction, medial splay, caudal-cranial pivoting and caudal-cranial translation. The retraction assembly provides medial retraction and comprises a housing, a rack, a gear, and a pawl. The housing has an interior lumen through which the rack extends, a gear recess that receives the gear, and a pawl recess that provides a low profile nest for the pawl. The rack includes a proximal attachment end, a set of top teeth, and a set of side teeth. The attachment end is virtually identical in structure and function to the distal face of the first arm described above, and thus a repeat discussion is unnecessary. The top teeth are spaced relatively close together and are configured to engage with the pawl. The side teeth are spaced farther apart than the top teeth and are configured to engage the gear. The larger side teeth allow for greater mechanical advantage during retraction when engaged with the gear, while the smaller teeth allow for more discreet locking positions. The gear includes a tooth portion and an engagement recess. The engagement recess receives a post of an actuator element, which also includes an engagement recess for engaging an actuator tool. Rotating the actuator element causes the gear to rotate, which in turn causes the rack to translate within the lumen. The pawl includes a distal engagement tip and a spring-loaded proximal release lever. The distal engagement tip engages with the top teeth on the rack to finely control the locking positions. A spring biases the pawl to contact the rack in a ratchet-like manner. Pushing on the release lever causes the distal engagement tip to lift off the rack, enabling free movement of the rack. The blade assembly is identical to the blade assembly described above with reference to first example secondary retractor, and thus any feature disclosed in relation to that blade assembly is applicable to the present blade assembly, rendering a repeat discussion unnecessary.

According to another embodiment, a fourth alternative example of a secondary retractor that can attach to the tissue retractor assembly is described herein. The fourth example secondary retractor is attachable to the caudal anchor blade and comprises a retraction assembly and a blade assembly. The secondary retractor allows for further connection to a secondary (e.g. medial) blade and drives further access to the spine medially with many degrees of freedom. For example, the secondary retractor may provide for medial retraction, medial splay, caudal-cranial pivoting and caudal-cranial translation. The retraction assembly provides medial retraction and comprises a housing, a rack, and a gear. The housing has an interior channel through which the rack extends and within which the gear engages the rack. The gear includes a tooth portion that engages the rack and an engagement recess that provides an engagement element for an actuator tool. The housing further has an attachment flange extending generally downward from the housing, and a pawl configured to engage the teeth of the rack, enabling fine resolution. The attachment flange is sized and configured to slideably engage the track of the anchor blade. The rack is double sided and has a first set of teeth positioned on an opposite side of the rack from a second set of teeth. The first set of teeth are spaced relatively close together and are configured to engage with the pawl. The second set of teeth are spaced farther apart than the first set of teeth and are configured to engage the gear. The larger second set of teeth allow for greater mechanical advantage during retraction when engaged with the gear, while the smaller first set of teeth allow for more discreet locking positions.

The blade assembly includes a base, pivoting crossbar, a blade coupler and a splay unit. The base is positioned at the distal end of the rack and includes a channel for receiving the pivoting crossbar. The pivoting crossbar can translate up to an inch in distance and can rotate on axis up to 40° in a continuously variable fashion. The pivoting crossbar may freely translate within the channel and has an internal O-ring which applies friction during translation guidance. The splay unit controls rotation and is identical in form and function to the splay unit of the left arm, and thus a detailed description of the like features need not be repeated. The pivoting crossbar is attached to a crankshaft that has an offset knuckle and pivoting stud allowing for attachment of a secondary blade. The crankshaft allows the secondary blade to be splayed offset of the axis of rotation of the pivoting crossbar. The eccentric movement persuades a secondary blade to move up and out of the surgeon's line of sight while splaying. The secondary blade attaches to the secondary retractor with an internal self-locking quick connect mechanism, for example such as those described above.

The fourth example secondary retractor may be used with a standard rack retractor. The present secondary retractor may also be used with the retractor assembly described above without departing from the scope of the disclosure. By way of example only, the standard rack retractor may include a first arm and second arm connected via a crossbar rack. The first and second arms are virtually identical to the left and right arms described above. The crossbar rack is received within a housing, which itself has a gear and pawl. Anchor blades differ from the several embodiments described above in that they attach to the bone anchors via hoop shims.

According to one example there is described a posterior spinal retractor for a maintaining an access corridor to a site along the posterior spinal column on which a surgical procedure is performed. The surgical procedure includes the use of first and second bone anchors anchorable into a first pedicle of a first vertebra and a second pedicle of a second vertebra, respectively. The spinal retractor includes a retractor body, a first blade, and a second blade. The retractor body has a first arm extending along a first arm axis and a second arm extending along a second arm axis. The first arm axis and second arm axis are parallel to one another and perpendicular to a first translation axis. The retractor body is operable to move the first retractor arm and second retractor arm relative to each other in a direction plane parallel to the first translation axis. The first arm includes a splay mechanism operable to rotate a portion of the first arm about the first arm axis and the second arm includes a splay mechanism operable to rotate a portion of the second arm about the second arm axis. The first retractor blade is coupleable to the first arm and has a distal end and a proximal end. The distal end of the first retractor blade includes an integral blade foot operable to directly couple to a first bone anchor shank. The blade foot permits angular adjustability of the first retractor blade relative to the first bone anchor shank. The second retractor blade is coupleable to the second arm and has a distal end and a proximal end. The distal end of the second retractor blade includes an integral blade foot operable to directly couple to a second bone anchor shank. The blade foot permitting angular adjustability of the second retractor blade relative to the second bone anchor shank.

According to another aspect of the posterior spinal retractor the first retractor blade includes a proximal connector that engages the first arm such that the rotatable portion of the first arm rotates relative to the first retractor blade about a limited first free rotation range. Beyond the limited first free rotation range the first retractor blade rotates with rotatable portion of the first arm to splay the distal end of the first retractor blade. The second retractor blade also includes a proximal connector that engages the second arm such that the rotatable portion of the second arm rotates relative to the second retractor blade about a limited second free rotation range. Beyond the limited second free rotation range the second retractor blade rotates with the rotatable portion of the second arm to splay the distal end of the second retractor blade.

According to another aspect of the posterior spinal retractor the proximal connector of the first retractor blade includes a clutch extension that is received within a clutch cavity on the rotatable portion of the first arm. The clutch extension has a lesser width than the width of the clutch cavity and the difference between the clutch extension width and the clutch cavity width defines the limited first free rotation range. The clutch becoming engaged when a side wall of the clutch extension contacts a sidewall of the clutch cavity.

According to another aspect of the posterior spinal retractor the proximal connector of the second retractor blade includes a clutch extension that is received within a clutch cavity on the rotatable portion of the second arm. The clutch extension has a lesser width than the width of the clutch cavity and the difference between the clutch extension width and the clutch cavity width defines the limited second free rotation range. The clutch becoming engaged when a side wall of the clutch extension contacts a sidewall of the clutch cavity.

According to another aspect of the posterior spinal retractor, when the first and second retractor blades are coupled to anchored first and second bone anchor shanks and the first retractor blade clutch and second retractor blade clutch are disengaged, the angle of the operative corridor between the first and second blades can be adjusted by moving the retractor body which in turn moves the proximal end of the first retractor blade and the proximal end of the second retractor blade in the same direction.

According to another aspect of the posterior spinal retractor, when the first and second retractor blades are coupled to anchored first and second bone anchor shanks and the first retractor blade clutch and second retractor blade clutch are disengaged, the volume of the operative corridor between the first and second blades can be adjusted by translating the first arm and second arm relative to each other to move the proximal ends of the first and second blades relative to each and relative to the anchored distal ends.

According to another aspect of the posterior spinal retractor, when the first and second retractor blades are coupled to anchored first and second bone anchor shanks and the first retractor blade clutch and second retractor blade clutch are engaged, the first and second arms can be translated relative to each other to adjust the distance between the first and second bone anchors.

According to another aspect of the posterior spinal retractor, when the first and second retractor blades are coupled to anchored first and second bone anchor shanks and the first retractor blade clutch and second retractor blade clutch are engaged, at least one of the first and second rotatable arm portions can be rotated to adjust the distance between the first and second bone anchors to compress or distract the disc space.

According to another aspect of the posterior spinal retractor the proximal connector of the first retractor blade includes a coupling mechanism configured to automatically lock the first retractor blade to the first retractor arm upon engagement.

According to another aspect of the posterior spinal retractor the coupling mechanism includes a release button configured to unlock the first retractor blade from the associated retractor body or secondary retractor body to facilitate decoupling.

According to another aspect of the posterior spinal retractor the proximal connector of the first retractor blade includes a second coupling mechanism structurally identical to the first coupling mechanism.

According to another aspect of the posterior spinal retractor, the spinal retractor includes a secondary retractor that couples to the second coupling mechanism.

According to another aspect of the posterior spinal retractor the second retractor blade is structurally identical to the first retractor blade.

According to another aspect of the posterior spinal retractor the secondary retractor body couples to both the second coupling mechanism of the first retractor blade and the secondary coupling mechanism of the second retractor blade.

According to another aspect of the posterior spinal retractor, there is a third retractor blade that is coupleable to the secondary retractor body.

According to another aspect of the posterior spinal retractor the distal end of the first retractor blade includes a static arm and a pivot arm pivotally coupled to the static arm. The blade foot includes a static foot extending from the static arm and a pivot foot extending from the pivot foot.

According to another aspect of the posterior spinal retractor the foot includes a center aperture sized to receive a neck of a bone anchor therein.

According to another aspect of the posterior spinal retractor the foot includes an open position with the pivot foot pivoted away from the static foot to permit passage of the bone anchor neck into the center aperture. The foot also includes a closed position with the pivot foot adjacent the static foot to prevent the removal of the bone anchor neck from the center aperture.

According to another aspect of the posterior spinal retractor the first retractor blade further includes a lock to lock the pivot foot in the closed position.

According to another aspect of the posterior spinal retractor the lock comprises a shaft that translates through a passage extending along one side of the retractor blade to engage the pivot arm.

According to another aspect of the posterior spinal retractor the pivot arm is biased to the open position and the shaft engages a ramped surface of the pivot arm to pivot the pivot arm towards the static arm as the shaft translates downward.

According to another aspect of the posterior spinal retractor the translation of the shaft is controlled by a set screw situated at the top of the retractor blade.

According to another aspect of the posterior spinal retractor a gap exists between the ends of the static foot and pivot foot when in the closed position.

According to another aspect of the posterior spinal retractor an inner surface of the foot is curved and angled.

According to another example, a surgical retractor blade is described. The surgical retractor blade includes a connector and a blade portion. The connector is configured to couple the retractor blade with a retractor. The blade portion includes a distal end having a static arm with a static foot extending transversely from the static arm. The distal end also has and a pivot arm with a pivot foot extending transversely from the pivot arm. The pivot arm is pivotally coupled to the static arm and is movable between a closed position and an open position. In the closed position the pivot foot and static foot cooperate to form capture ring. The capture ring is configured to capture an implantable bone anchor therein. In the open position passage of the implantable bone anchor into and out of the capture ring is permitted.

According to another aspect of the retractor blade the retractor blade includes a lock to lock the pivot arm in the closed position.

According to another aspect of the retractor blade the lock comprises a shaft that translates through a passage extending along one side of the retractor blade to engage the pivot arm.

According to another aspect of the retractor blade the pivot arm is biased to the open position and the shaft engages a ramped surface of the pivot arm to pivot the pivot arm towards the static arm as the shaft translates downward.

According to another aspect of the retractor blade the translation of the shaft is controlled by a set screw situated at the top of the retractor blade.

According to another aspect of the retractor blade a gap exists between the ends of the static foot and pivot foot when in the closed position.

According to another aspect of the retractor blade an inner surface of the capture ring is curved and angled.

According to another aspect of the retractor blade the connector includes a coupling mechanism configured to automatically lock the retractor blade to the retractor when engaged.

According to another aspect of the retractor blade the coupling mechanism includes a release button configured to unlock the retractor blade from the retractor to facilitate decoupling.

According to another aspect of the retractor blade the connector includes a second coupling mechanism structurally identical to the coupling mechanism.

According another example, the present application describes a tissue retractor. The tissue retractor includes first and second elongated rack members dimensioned to translate linearly in opposite directions. Each rack member has a toothed side. The tissue retractor further includes an access retractor body. The access retractor body includes a rack housing configured to receive the first and second rack members, a pinion positioned between the first and second rack members and simultaneously engaged with the toothed sides of each of the first and second rack members, a pawl operable to prohibit translation of the first and second rack members, and a torque input element in communication with the pinion, the torque input element operable to cause translation of the first and second rack members. A first adjustable retractor arm is fixedly attached to the first rack member in a perpendicular orientation, and includes a proximal segment fixedly attached to the first rack member and a distal segment coupled to the proximal segment, the distal segment including a blade engagement post and a splay assembly. A second adjustable retractor arm is fixedly attached to the second rack member in a perpendicular orientation, and includes a proximal segment fixedly attached to the second rack member and a distal segment coupled to the proximal segment, the distal segment including a blade engagement post and a splay assembly. The tissue retractor further includes a retractor blade including a coupler and a blade portion, the coupler being configured to releaseably receive the blade post of the first retractor arm, the blade portion extending distally from the coupler and having a distal end comprising a fixed portion and a pivot portion, the pivot portion being coupled to the fixed portion with a pin such that the pivot portion pivots away from the fixed portion in a plane parallel to the width of the blade portion, the pivot portion being moveable between a closed, non-pivoted position and an open, pivoted position.

According to another example aspect of the tissue retractor the distal end of the fixed portion of the retractor blade comprises a static foot, the static foot having a first semicircular flange extending away from the plane of the width of the blade, the first semicircular flange having a first contact surface.

According to another example aspect of the tissue retractor the distal end of the pivot portion comprises a pivot foot having a second semicircular flange extending away from the plane of the width of the blade, the second semicircular flange having a second contact surface.

According to another example aspect of the tissue retractor the first and second semicircular flanges act in concert to form a capture element having a center aperture sized to receive a neck portion of a bone anchor therein when the pivot portion is in the closed position.

According to another example aspect of the tissue retractor the first and second contact surfaces are sized and dimensioned to receive a portion of a spherical head of a bone anchor therein such that the bone anchor has a polyaxial relationship with the capture element.

According to another example aspect of the tissue retractor the retractor blade includes a locking mechanism for locking the pivot portion in the closed position.

According to another example aspect of the tissue retractor the locking portion comprises an elongated shaft having a proximal end and a distal end, the proximal end positioned at the proximal end of the retractor blade and the distal end positioned at the distal end of the retractor blade, the elongated shaft being moveable between a locked position in which the distal end contacts the pivot portion and an unlocked position in which the distal end does not contact the pivot portion.

According to another example aspect of the tissue retractor the locking mechanism includes an actuator positioned at the proximal end of the retractor blade in communication with the elongated shaft such that rotation of the actuator causes movement of the elongated shaft between the locked and unlocked positions.

According to another example aspect of the tissue retractor, the tissue retractor further includes a second retractor blade having a coupler and a blade portion, the coupler being configured to releaseably receive the blade post of the second retractor arm, the blade portion extending distally from the coupler and having a distal end comprising a fixed portion and a pivot portion, the pivot portion being coupled to the fixed portion with a pin such that the pivot portion pivots away from the fixed portion in a plane parallel to the width of the blade portion.

According to another example aspect of the tissue retractor the first and second retractor blades are identical.

According to another example aspect of the tissue retractor, the tissue retractor further comprises a secondary retractor assembly removeably attached to the coupler, the secondary retractor assembly including a third retractor blade.

According to still another example, a first method, for using a tissue retractor assembly in a transforaminal lumbar interbody fusion (TLIF) surgery is described. The example method includes the steps of: (a) locating a surgical target site in a lumbar spine of a patient; (b) forming an incision to create a surgical wound; (c) attaching a first retractor blade to a first bone anchor and a first insertion tool, the first bone anchor having a spherical head, a threaded shank, and a neck portion positioned between the spherical head and threaded shank; (d) attaching a second retractor blade to a second bone anchor and a second insertion tool; (e) advancing the first retractor blade into the surgical wound while simultaneously implanting the first bone anchor into a first pedicle; (f) advancing the second retractor blade into the surgical wound while simultaneously implanting the second bone anchor into a second pedicle; (g) attaching a tissue retractor to the first and second retractor blades, the tissue retractor comprising an access retractor body, the access retractor body including a rack housing configured to receive first and second elongated rack members dimensioned to translate linearly in opposite directions, each rack member having a toothed side, a pinion positioned between the first and second rack members and simultaneously engaged with the toothed sides of each of the first and second rack members, a pawl operable to prohibit translation of the first and second rack members, and a torque input element in communication with the pinion, the torque input element operable to cause translation of the first and second rack members, a first adjustable retractor arm fixedly attached to the first rack member in a perpendicular orientation, the first retractor arm including a proximal segment fixedly attached to the first rack member and a distal segment pivotally coupled to the proximal segment, the distal segment including a blade engagement post and a splay assembly, and a second adjustable retractor arm fixedly attached to the second rack member in a perpendicular orientation, the second retractor arm including a proximal segment fixedly attached to the second rack member and a distal segment coupled to the proximal segment, the distal segment including a blade engagement post and a splay assembly; and (h) operating the tissue retractor to retract the surgical wound.

According to another example aspect of the first method the first retractor blade comprises a coupler and a blade portion, the coupler being configured to releaseably receive the blade post of the first retractor arm, the blade portion extending distally from the coupler and having a distal end comprising a fixed portion and a pivot portion, the pivot portion being coupled to the fixed portion with a pin such that the pivot portion pivots away from the fixed portion in a plane parallel to the width of the blade portion, the pivot portion being moveable between a closed, non-pivoted position and an open, pivoted position.

According to another example aspect of the first method the second retractor blade comprises a coupler and a blade portion, the coupler being configured to releaseably receive the blade post of the second retractor arm, the blade portion extending distally from the coupler and having a distal end comprising a fixed portion and a pivot portion, the pivot portion being coupled to the fixed portion with a pin such that the pivot portion pivots away from the fixed portion in a plane parallel to the width of the blade portion, the pivot portion being moveable between a closed, non-pivoted position and an open, pivoted position.

According to another example aspect of the first method, a further step of attaching a rod tulip to the spherical head of the bone anchor while the bone anchor is attached to the retractor blade is included.

According to another example aspect of the first method, a further step of securing a spinal rod within the rod tulip is included.

According to another example aspect of the first method a further step of detaching the retractor blade from the bone anchor after completing the step of securing a spinal rod within the rod tulip.

According to another example, a second method, for attaching a fixation system to the spine of a patient is described. The fixation system includes at least two bone anchors and a spinal rod linking the at least two bone anchors. The method includes the steps of: connecting a first bone anchor to a first retractor blade, advancing the first bone anchor and first retractor blade together to a first spinal vertebra, and anchoring the first bone anchor through a pedicle of the first spinal vertebra; connecting a second bone anchor to a second retractor blade, advancing the second bone anchor and second retractor blade together to a second spinal vertebra, and anchoring the second bone anchor through a pedicle of the second vertebra, wherein the second vertebra is separated from the first vertebra by an intervertebral disc space and the first vertebra, second vertebra, and intervertebral disc space comprise a first spinal level; connecting the first retractor blade and the second retractor blade with a retractor body, the retractor body being positioned laterally away from the spine relative to the first and second retractor blades, operating the retractor body to expand an operative corridor formed between the first retractor blade and second retractor blade from the skin level of the patient to the spine; and linking the first bone anchor and the second bone anchor with the spinal rod.

According to another example aspect of the second method the additional step of adjusting the angle of the operative corridor until the operative corridor is parallel to the intervertebral disc is included.

According to another example aspect of the second method, adjusting the angle of the operative corridor is accomplished by moving a proximal end of the first retractor blade and a proximal end of the second retractor blade in the same direction while a distal end of the first retractor blade remains positioned adjacent the first pedicle and a distal end of the second retractor blade remains positioned adjacent the second pedicle.

According to another example aspect of the second method the angle of the operative corridor is adjusted in one of a cephalad or caudal direction.

According to another example aspect of the second method the angle of the operative corridor is adjusted in one of an anterior and posterior direction.

According to another example aspect of the second method the angle of the operative corridor is adjusted in both one of a cephalad and caudal direction and in one of an anterior and posterior direction.

According to another example aspect of the second method the first retractor blade is connected to the first bone anchor in a polyaxial engagement and the second retractor blade is connected to the second bone anchor in a polyaxial engagement.

According to another example aspect of the second method the additional step of operating the retractor body to distract the intervertebral disc space is included.

According to another example aspect of the second method the additional step of coupling a secondary retractor body directly to one of the first retractor blade and second retractor blade is included. The secondary retractor body is positioned medially relative to the first and second retractor blades. A third retractor blade is connected to the secondary retractor body.

According to another example aspect of the second method the secondary retractor body includes a retraction mechanism and splay mechanism.

According to another example aspect of the second method the additional step of operating at least one of the secondary retractor body retraction mechanism and splay mechanism to expand the size of the operative corridor medially is included.

According to another example aspect of the second method the secondary retractor body couples directly to the first retractor blade and the second retractor blade.

According to another example aspect of the second method the first anchor portion is connected to the first retractor blade via a capture ring integral to and extending from the a distal end of the first retractor blade. The capture ring has a center aperture sized to receive a neck of a bone anchor therein.

According to another example aspect of the second method the capture ring comprises a static foot and a pivot foot, the pivot foot pivoting away from the static foot to an open position to permit passage of the bone anchor neck into the capture ring and pivoting towards the static foot to a closed position capture the bone anchor neck within the capture ring center aperture.

According to another example aspect of the second method the first retractor blade further comprises a lock to lock the pivot foot in the closed position.

According to another example aspect of the second method the distal end of the first retractor blade includes a static arm and a pivot arm pivotally coupled to the static arm, the static foot extending from the static arm and the pivot foot extending from the pivot foot.

According to another example aspect of the second method, connecting the third retractor blade to the secondary retractor body includes advancing the third retractor blade to the spine while coupled to an insertion tool, using the distal end of the third blade to first elevate tissue off of the spine and then connecting the third blade to the secondary retractor body and releasing the insertion tool.

According to another example aspect of the second method the distal end of the third blade includes a distal end extension configured to lock to the third blade in a number of discrete extension positions, wherein the steps of using the distal end of the third blade to first elevate tissue off of the spine and then connecting the third blade to the secondary retractor body further include the step of manipulating the insertion tool to disengage a lock of the distal extension to adjust the height of the blade to connect to the third blade to the secondary retractor body while maintain contact with the spine at the distal end.

According to another example aspect of the second method the additional step of operating on the first spinal level through the operating corridor prior to linking the first bone anchor and the second bone anchor with the spinal rod is included.

According to another example aspect of the second method operating on the first spinal level includes one or more of a facetectomy, decompression, annulotomy, and discectomy.

According to another example aspect of the second method at least a discectomy is performed and comprising the additional step of inserting an implant into the intervertebral space after the discectomy.

According to another example, a third method, for attaching a fixation system to the spine of a patient is described. The fixation system includes at least two bone anchors and a spinal rod linking the at least two bone anchors. The method includes the steps of: connecting a first retractor blade directly to a shank of a first bone anchor via a capture mechanism integrally associated with a distal end of the first retractor blade, advancing the first bone ancho shank and first retractor blade together to a first spinal vertebra, and anchoring the first bone anchor shank through a pedicle of the first spinal vertebra; connecting a second retractor blade directly to a shank of a second bone anchor via a capture mechanism integrally associated with a distal end of the second retractor blade, advancing the second bone anchor shank and second retractor blade together to a second spinal vertebra, and anchoring the second bone anchor shank through a pedicle of the second vertebra, wherein the second vertebra is separated from the first vertebra by an intervertebral disc space and the first vertebra, second vertebra, and intervertebral disc space comprise a first spinal level; connecting a retractor body to the first retractor blade and the second retractor blade and operating the retractor body to expand an operative corridor formed between the first retractor blade and second retractor blade from the skin level of the patient to the spine; and linking the first bone anchor and the second bone anchor with a the spinal rod.

According to another example aspect of the third method the additional step of adjusting the angle of the operative corridor until the operative corridor is parallel to the intervertebral disc is included.

According to another example aspect of the third method adjusting the angle of the operative corridor is accomplished by moving a proximal end of the first retractor blade and a proximal end of the second retractor blade in the same direction while a distal end of the first retractor blade remains positioned adjacent the first pedicle and a distal end of the second retractor blade remains positioned adjacent the second pedicle.

According to another example aspect of the third method the angle of the operative corridor is adjusted in one of a cephalad or caudal direction.

According to another example aspect of the third method the angle of the operative corridor is adjusted in one of an anterior and posterior direction.

According to another example aspect of the third method the angle of the operative corridor is adjusted in both one of a cephalad and caudal direction and in one of an anterior and posterior direction.

According to another example aspect of the third method the first retractor blade is connected to the first bone anchor shank in a polyaxial engagement and the second retractor blade is connected to the second bone anchor shank in a polyaxial engagement.

According to another example aspect of the third method the additional step of operating the retractor body to distract the intervertebral disc space is included.

According to another example aspect of the third method the additional step of coupling a secondary retractor body directly to one of the first retractor blade and second retractor blade, the secondary retractor body being positioned medially relative to the first and second retractor blades, and connecting a third retractor blade to the secondary retractor body is included.

According to another example aspect of the third method the secondary retractor body includes a retraction mechanism and splay mechanism.

According to another example aspect of the third method the additional step of operating at least one of the secondary retractor body retraction mechanism and splay mechanism to expand the size of the operative corridor medially is included.

According to another example aspect of the third method the secondary retractor body couples directly to the first retractor blade and the second retractor blade.

According to another example aspect of the third method the first anchor portion is connected to the first retractor blade via a capture ring integral to and extending from the a distal end of the first retractor blade, the capture ring capture ring having a center aperture sized to receive a neck of a bone anchor therein.

According to another example aspect of the third method the capture ring comprises a static foot and a pivot foot, the pivot foot pivoting away from the static foot to an open position to permit passage of the bone anchor neck into the capture ring and pivoting towards the static foot to a closed position capture the bone anchor neck within the capture ring center aperture.

According to another example aspect of the third method the first retractor blade further comprises a lock to lock the pivot foot in the closed position.

According to another example aspect of the third method the distal end of the first retractor blade includes a static arm and a pivot arm pivotally coupled to the static arm, the static foot extending from the static arm and the pivot foot extending from the pivot foot.

According to another example aspect of the third method connecting the third retractor blade to the secondary retractor body includes advancing the third retractor blade to the spine while coupled to an insertion tool, using the distal end of the third blade to first elevate tissue off of the spine and then connecting the third blade to the secondary retractor body and releasing the insertion tool.

According to another example aspect of the third method the distal end of the third blade includes a distal end extension configured to lock to the third blade in a number of discrete extension positions. The steps of using the distal end of the third blade to first elevate tissue off of the spine and then connecting the third blade to the secondary retractor body further include the step of manipulating the insertion tool to disengage a lock of the distal extension to adjust the height of the blade to connect to the third blade to the secondary retractor body while maintain contact with the spine at the distal end.

According to yet another example, a fourth method, for fixing a fixation system to the spine of a patient is described. The fixation system including at least two bone anchors and a spinal rod linking the at least two bone anchors, comprising the steps of: connecting a first bone anchor to a first retractor blade, advancing the first bone anchor and first retractor blade together to a first spinal vertebra, and anchoring the first bone anchor through a pedicle of the first spinal vertebra; connecting a second bone anchor to a second retractor blade, advancing the second bone anchor and second retractor blade together to a second spinal vertebra, and anchoring the second bone anchor through a pedicle of the second vertebra, wherein the second vertebra is separated from the first vertebra by an intervertebral disc space and the first vertebra, second vertebra, and intervertebral disc space comprise a first spinal level; connecting a retractor body to the first retractor blade and the second retractor blade and operating the retractor body to expand an operative corridor formed between the first retractor blade and second retractor blade cranially and caudally from the skin level of the patient to the spine; connecting a secondary retractor body directly to at least one of the first retractor blade and second retractor blade; connecting a third retractor blade to the secondary retractor body and operating the secondary retractor body to move the third retractor blade medially and further expand the size of the operative corridor; and linking the first bone anchor and the second bone anchor with the spinal rod.

According to another example aspect of the fourth method the secondary retractor body couples directly to the first retractor blade and the second retractor blade.

According to another example aspect of the fourth method the secondary retractor body includes a retraction mechanism and splay mechanism.

According to another example aspect of the fourth method the step of operating the secondary retractor body to move the third retractor blade medially includes at least one of operating the retraction mechanism to move the entire third blade medially and operating the splay mechanism to move the distal end of the third blade medially.

According to another example aspect of the fourth method the first retractor blade is connected to the first bone anchor shank in a polyaxial engagement and the second retractor blade is connected to the second bone anchor shank in a polyaxial engagement.

According to another example aspect of the fourth method the first anchor portion is connected to the first retractor blade via a capture ring integral to and extending from the a distal end of the first retractor blade, the capture ring capture ring having a center aperture sized to receive a neck of a bone anchor therein.

According to another example aspect of the fourth method the capture ring includes a static foot and a pivot foot, the pivot foot pivoting away from the static foot to an open position to permit passage of the bone anchor neck into the capture ring and pivoting towards the static foot to a closed position capture the bone anchor neck within the capture ring center aperture.

According to another example aspect of the fourth method the first retractor blade further includes a lock to lock the pivot foot in the closed position.

According to another example aspect of the fourth method the distal end of the first retractor blade includes a static arm and a pivot arm pivotally coupled to the static arm, the static foot extending from the static arm and the pivot foot extending from the pivot foot.

According to another example aspect of the fourth method connecting the third retractor blade to the secondary retractor body includes advancing the third retractor blade to the spine while coupled to an insertion tool, using the distal end of the third blade to first elevate tissue off of the spine and then connecting the third blade to the secondary retractor body and releasing the insertion tool.

According to another example, a fifth method, for performing a spinal fusion procedure on a spinal segment of a human spine, the spinal segment including at least a first vertebra and a second vertebra separated from the first vertebra by an intervertebral disc space is described. The method includes the steps of: (a) anchoring a first anchor portion to a first pedicle, the first anchor portion being directly connected to a first retractor blade of a retractor assembly via a mechanism integrally associated with a distal end of the first retractor blade; (b) anchoring a second anchor portion to a second pedicle, the second anchor portion being directly connected to a second retractor blade of the retractor assembly via a mechanism integrally associated with a distal end of the second retractor blade; (c) connecting the first retractor blade to a first arm of a retractor body of the retractor assembly and connecting the second retractor blade to a second arm of the retractor body; (d) operating the retractor body to increase the distance between the first arm and the second arm to expand an operating corridor between the first retractor blade and the second retractor blade; (e) connecting a secondary retractor body directly to at least one of the first retractor blade and second retractor blade, (f) advancing a third retractor blade through the operative corridor and connecting the third retractor blade to the secondary retractor body, and operating the secondary retractor body to move the third retractor blade and further expand the size of the operating corridor; (f) preparing the intervertebral disc space to receive an implant; (g) implanting a fusion implant in the intervertebral disc space; (h) disconnecting the first retractor blade from the first anchor portion and attaching a first receiver portion to the first anchor portion; (i) disconnecting the second retractor blade from the second retractor portion and attaching a second receiver portion to the second anchor portion; (j) inserting and locking a rod into the first receiver portion and second receiver portion; and (k) removing the first and second retractor blades from the operative corridor and closing the operative corridor.

According to another example aspect of the fifth method the first anchor portion is connected to the first retractor blade via a capture ring integral to and extending from the a distal end of the first retractor blade.

According to another example aspect of the fifth method the capture ring has a center aperture sized to receive a neck of a bone anchor therein.

According to another example aspect of the fifth method the capture ring comprises a static foot and a pivot foot, the pivot foot pivoting away from the static foot to an open position to permit passage of the bone anchor neck into the capture ring and pivoting towards the static foot to a closed position capture the bone anchor neck within the capture ring center aperture.

According to another example aspect of the fifth method the first retractor blade further comprises a lock to lock the pivot foot in the closed position.

According to another example aspect of the fifth method the distal end of the first retractor blade includes a static arm and a pivot arm pivotally coupled to the static arm, the static foot extending from the static arm and the pivot foot extending from the pivot foot.

According to another example aspect of the fifth method the first retractor blade includes a proximal connector with dual coupling mechanisms to permit coupling of the first retractor blade to each of the retractor body and secondary retractor body.

According to another example aspect of the fifth method the coupling mechanisms are structurally identical to permit each of the retractor body and the secondary retractor body to couple to either coupling mechanism.

According to another example aspect of the fifth method the dual coupling mechanisms are configured to automatically lock the first retractor blade to the associated retractor body or secondary retractor body upon engagement.

According to another example aspect of the fifth method the dual coupling mechanisms each include a release button configured to unlock the first retractor blade from the associated retractor body or secondary retractor body to facilitate decoupling.

According to another example aspect of the fifth method the second retractor blade is structurally identical to the first retractor blade.

According to another example aspect of the fifth method the third retractor blade has a distal end extension that is configured to securely maintain a plurality of discrete extension positions.

According to another example aspect of the fifth method the distal end extension includes a cantilevered ratchet mechanism that engages ratchet grooves on an inner face of the third retractor blade.

According to another example aspect of the fifth method the distal end extension includes a serrated end curved to maximize contact along a lamina.

BRIEF DESCRIPTION OF THE DRAWINGS

Many advantages of the presently described article and related methods will be apparent to those skilled in the art with a reading of this specification in conjunction with the attached drawings, wherein like reference numerals are applied to like elements and wherein:

FIG. 12 is a perspective view of the anchor blade of FIG. 11 with the pivot arm in an "unlocked" position;

FIG. 13 is a perspective view of the anchor blade of FIG. 11 juxtaposed with a setscrew driver instrument configured for use with the anchor blade;

FIG. 23 is a plan view of the back side of the secondary retractor blade of FIG. 22 juxtaposed with the distal end of an insertion instrument configured for use with the secondary blade;

FIG. 24 is a plan view of the front side of the secondary retractor blade of FIG. 22 juxtaposed with the distal end of an insertion instrument configured for use with the secondary blade;

FIG. 25 is a plan view of the front side of the secondary retractor blade of FIG. 22 coupled to the distal end of the insertion instrument;

FIG. 26 is a perspective view of the secondary retractor blade of FIG. 22 coupled to an insertion instrument;

DETAILED DESCRIPTION OF A PREFERRED EMBODIMENT

Figure 1:
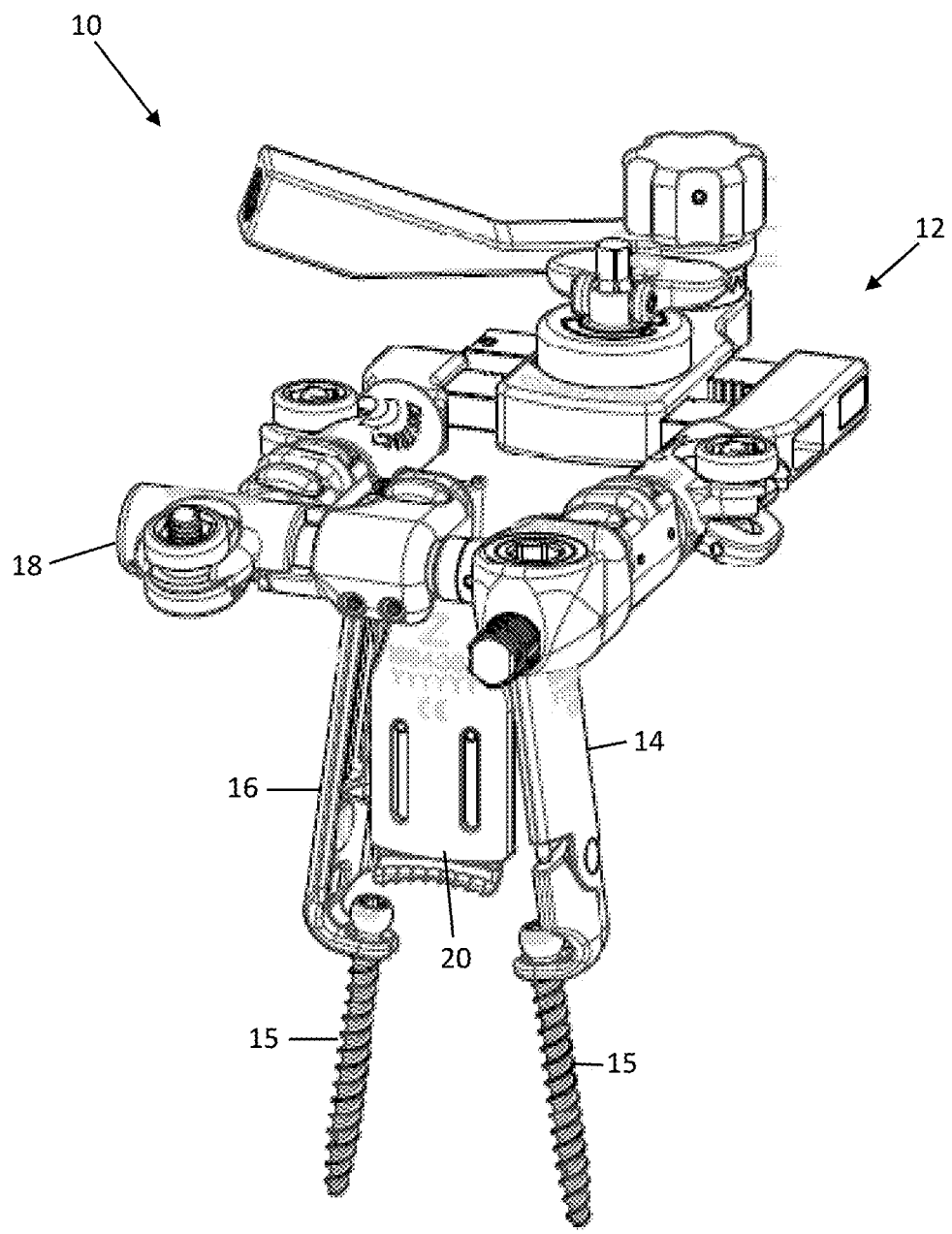
FIG. 1 is a perspective view of an example of a retractor assembly according to a first embodiment.
Figure 2:
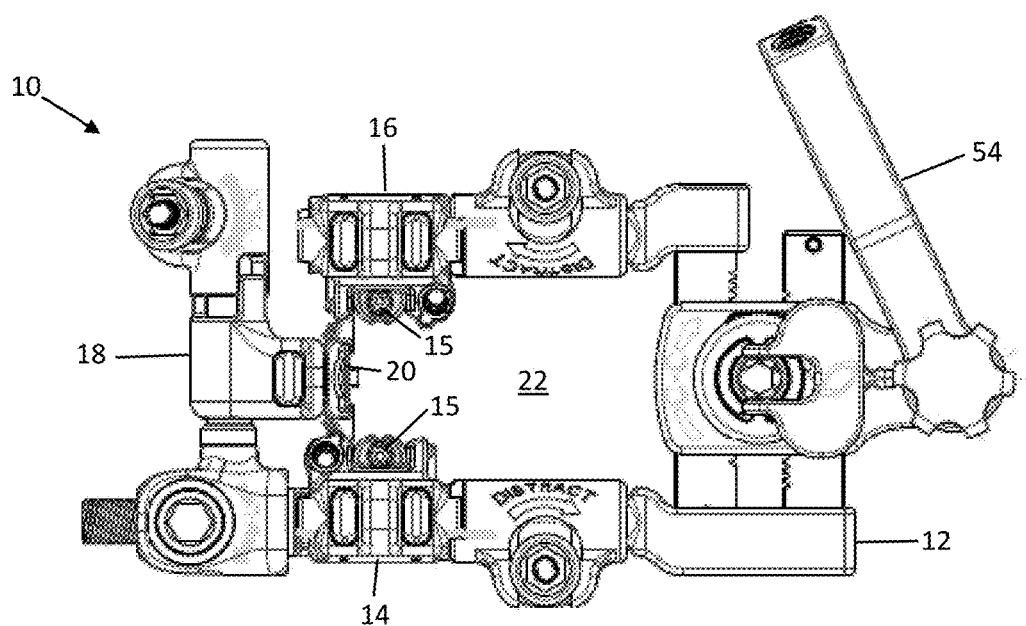
FIG. 2 is a top plan view of the retractor assembly of FIG. 1.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The minimally disruptive retractor and related methods disclosed herein boast a variety of inventive features and components that warrant patent protection, both individually and in combination.

The present application describes a tissue retractor assembly and related instruments and methods for performing minimally invasive spinal surgery, for example transforaminal lumbar interbody fusion (TLIF) surgery. The tissue retractor is used in conjunction with bone anchors to establish and maintain an operative corridor to the surgical target site. More particularly, the retractor anchors to the anatomy (e.g. pedicles) adjacent the surgical target site (e.g. intervertebral disc) to both anchor the exposure and define the boundaries with anatomical landmarks to orient the surgeon and facilitate navigation. Once this access corridor has been established, the disc space and vertebral endplates may be prepared, one or more interbody implants may be inserted into the disc space, and spinal rods may then be used to align and compress or reduce the construct.

Referring to FIGS. 1-4, the retractor assembly 10 includes an access retractor body 12, first and second anchor blades 14, 16, a secondary retractor 18, and a secondary blade 20. The first and second anchor blades 14, 16 capture a portion of bone anchors 15 to anchor the retractor 10 to the anatomy. When fully assembled and in operation, the access retractor body 12, anchor blades 14, 16, and secondary blade 20 establish and define a working corridor 22 through which access to the surgical target site is achieved. This working corridor 22 is expandable in a caudal-cranial direction as well as medially.

Figure 5:
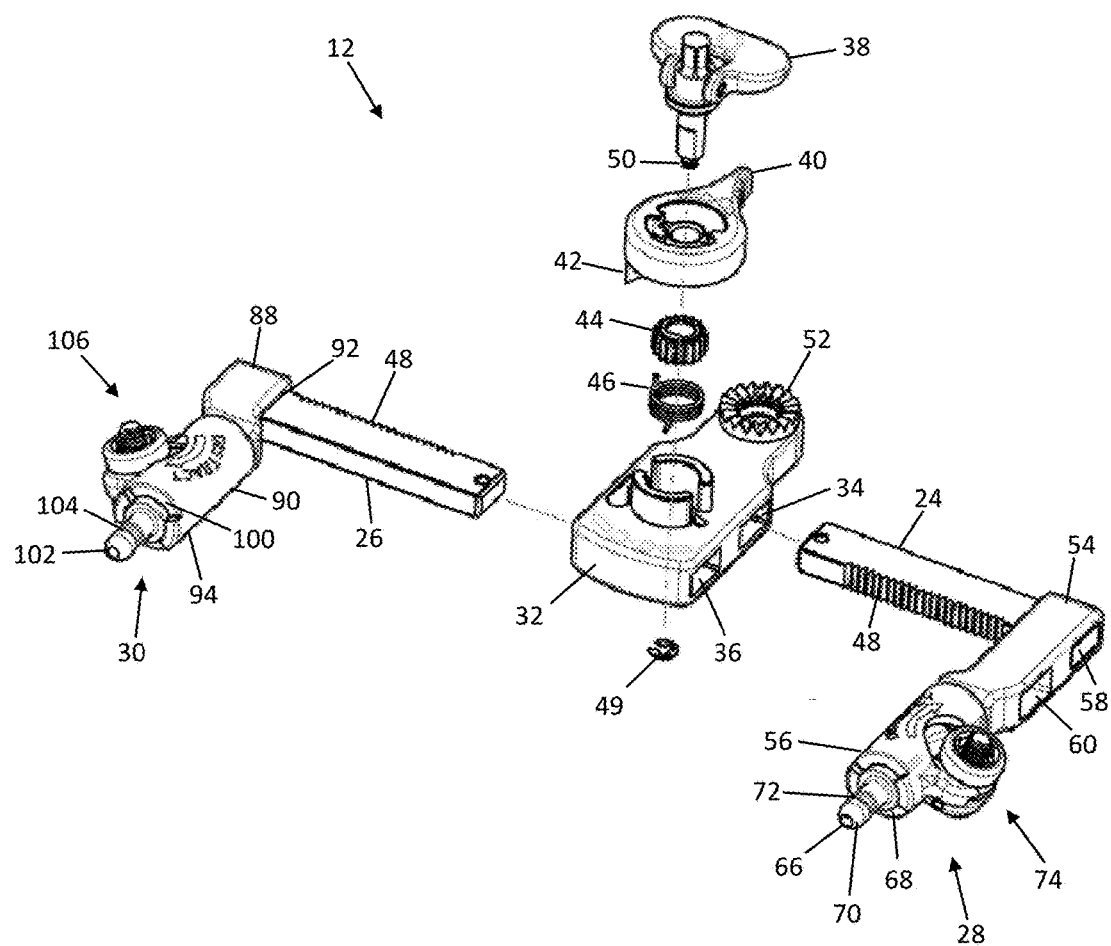
FIG. 5 is an exploded perspective view of an access retractor body forming part of the retractor assembly of FIG. 1.

With additional reference to FIG. 5, the access retractor body 12 includes first and second racks 24, 26, and left and right arms 28, 30. The first and second anchor blades 14, 16 are removably attached to the left and right arms 28, 30, respectively. In use during a TLIF procedure described herein, the retractor assembly 10 may be positioned relative to the patient such that the access retractor body 12 is located laterally of the wound (away from the patient's body). This advantageously positions the main part of the retractor outside of the fluoroscopy window. Although the first anchor blade 14 is described herein as being removably attached to the left arm 28 and the second anchor blade 16 is described as being removably attached to the right arm 30 it should be understood that the first and second anchor blades 14, 16 are virtually identical in form and function, and therefore are interchangeable.

The access retractor body 12 includes a base 32 having first and second channels 34, 36 extending laterally therethrough. The first and second channels 34, 36 are sized and dimensioned to receive the first and second racks 24, 26 respectively therein, and are separated from one another by a distance sufficient to enable placement of a pinion 44 to control translation of the racks 24, 26 as described below. A thumb tab 38 is rotatable to control the directional translation of the racks 24, 26. By way of example only, rotating the thumb tab 38 in a clockwise direction "opens" the retractor by simultaneously causing the first rack 24 to translate toward the left (relative to the retractor) and the second rack 26 to translate toward the right. This translation in turn causes the retractor blades 14, 16 to move in the same direction as the racks, controlling the size of the surgical wound. Thus, if the access body 12 is positioned laterally of the surgical wound away from the patient's body, the first retractor blade 14 will translate in a caudal direction, and the second retractor blade 16 will translate in a cranial direction. A pawl 40, moveable from a first (e.g. "unlocked") position to a second (e.g. "locked") position is provided to enable the user to lock the retractor 10 in an open position during use.

The pawl 40 includes a wedge 42 that is configured to engage the teeth 48 of the second rack 26 and directly prevent translation of the second rack 26 when the pawl 40 is in the second "locked" position. This also indirectly prevents translation of the first rack 24, effectively locking the retractor 10 in an "open" configuration. When the pawl 40 is in the first "unlocked" position, the wedge 42 is disengaged from the teeth 48, allowing free translation of the racks 24, 26. A pinion 44 is positioned between the racks 24, 26 and is mechanically coupled with the thumb tab 38 such that turning the thumb tab 38 causes the pinion 44 to rotate, which in turn causes the racks 24, 26 to translate. A coiled spring 46 is provided to bias the pawl 40 in a locked position, thereby passively allowing the retractor to open freely. A clip 49 is provided on the underside of the base 32 and engages a post 50 on the thumb tab to secure the construct together. The access retractor body 12 further includes an articulating arm attachment 52 to enable attachment to an articulating arm 54 to secure the retractor assembly 10 to the patient's bedrail (or other static, rigid mounting location) during use.

By way of example only, the racks 24, 26 are generally rectangular elongated members having a plurality of teeth 48 distributed on one side of each of the racks 24, 26. The teeth 48 are configured to interact with the pinion 44 described above to allow controlled translation of the arms 28, 30.

The left arm 28 includes a proximal segment 54 and a distal segment 56. The proximal segment 54 includes a first aperture 58 and a second aperture 60. The first aperture 58 is configured to fixedly receive the first rack 24 such that the first rack 24 and proximal segment 54 are generally perpendicular to one another. Thus, translation of the first rack 24 in either direction causes a corresponding movement of the left arm 28 in the same direction. The second aperture 60 is configured to slidingly receive the second rack 26 therethrough such that the second rack 26 is able to pass through the proximal segment 54 unencumbered in either direction during translation.

Figure 6:
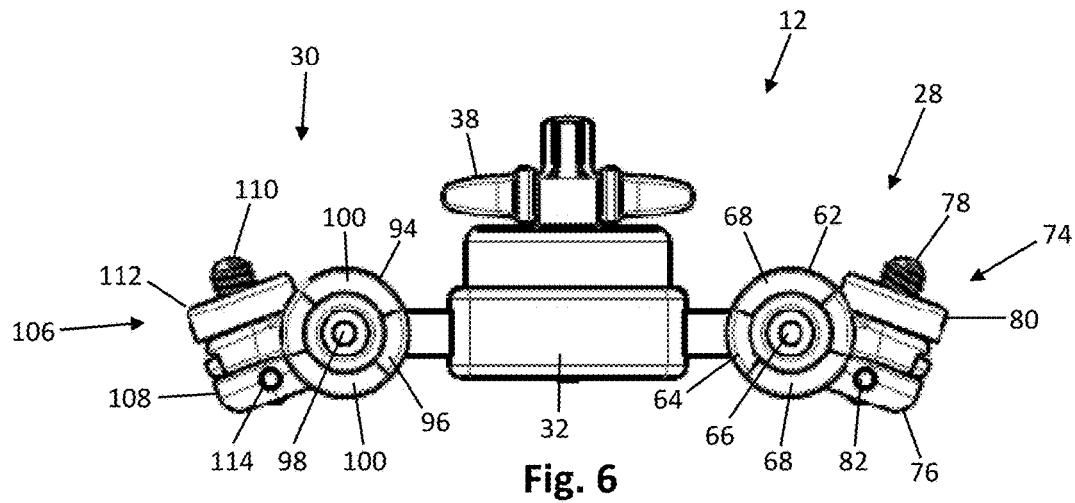
FIG. 6 is a front plan view of the access retractor body of FIG. 5, with the splay units in a first position.
Figure 7:
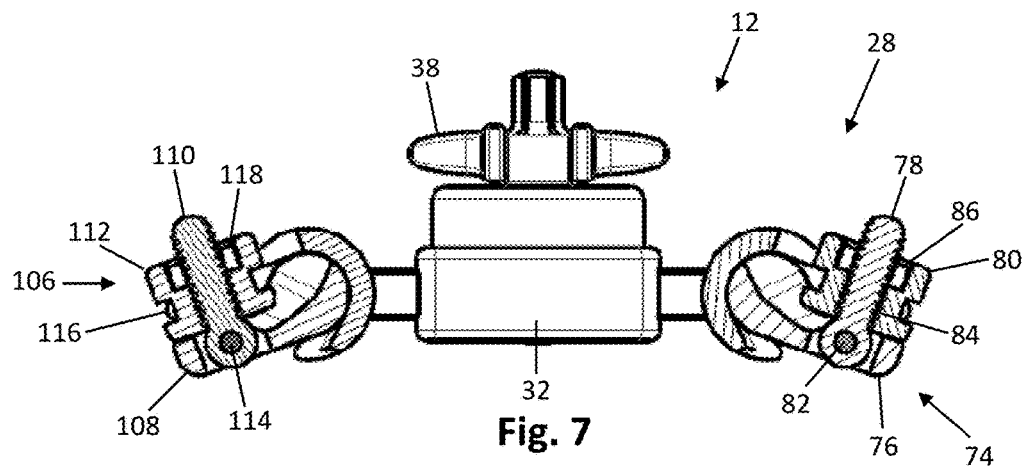
FIG. 7 is a sectional view of the access retractor body of FIG. 5.
Figure 8:
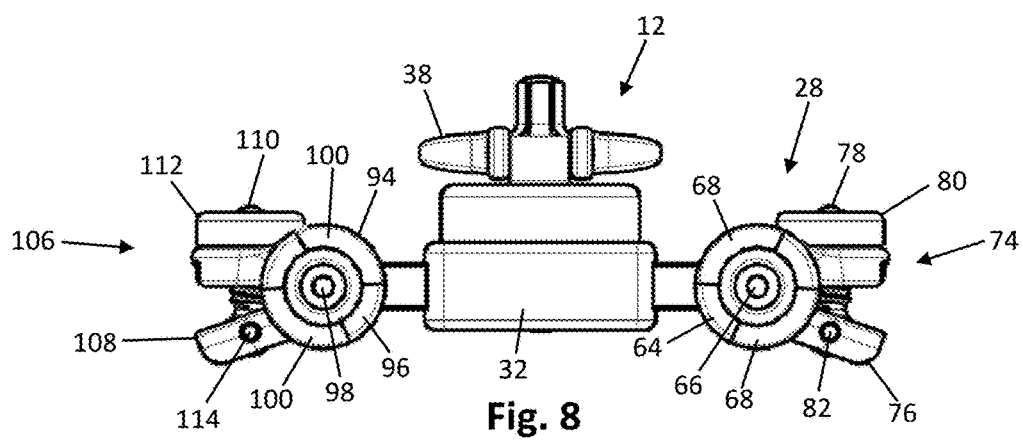
FIG. 8 is a front plan view of the access retractor body of FIG. 5, with the splay units in a second position.

The distal segment 56 is connected to the proximal segment 54 and is configured to releasably engage the first anchor blade 14. The distal segment 56 includes a generally cylindrical housing 62 having a distal face 64. The distal face 64 includes a central post 66 protruding distally from the center of the distal face 64 and a pair of opposing recesses 68 positioned on the perimeter of the distal face 64 on either side of the central post 66. The central post 66 is configured to mate with the attachment aperture 232 of the anchor blade 14 to securely attach the anchor blade 14 to the left arm 28. The central post 66 is generally cylindrical and includes a tapered leading end 70 and a circumferential recess 72 positioned between the leading end 70 and the distal face 64. The housing 62 is able to rotate, thus causing the anchor blade 14 to rotate and effect tissue distraction. This rotation is independent of the second anchor blade 16, and controlled by a splay unit 74 (FIGS. 6-8). The splay unit 74 includes a flange 76 extending laterally away from the housing 62, a threaded jack screw 78, and a cap 80. The jack screw 78 is pivotably secured to the flange 76 via a post 82. The cap 80 includes a threaded central aperture 84 and an engagement recess 86 for receiving a distal end of an activation instrument (not shown) such as a T-handle (for example). As the cap 80 is rotated by the activation instrument, it translates (in either direction depending on the direction of rotation of the instrument) along the jack screw 78. This causes the jack screw 78 to pivot about the pin 82, which in turn causes the cap 80 to transfer a torque to the housing 62, and more specifically the opposing recesses 68.

As described below, the recesses 68 cooperate with the flanges 236 of the anchor blade 14 and act as a clutch. That is, the recesses 68 (e.g. clutch cavities) receive the flanged 236 (e.g. clutch extensions) when the blade and arm are coupled. The recesses 68 are wider than the flanges 236 such that the flange can rotate within the recess a limited amount until a sidewall of the flanges engages a sidewall of the recess (e.g. the clutch is engaged). Once the clutch is engaged the anchor blade will no longer pivot relative to the arm and will instead rotate (splay) with the arm, thus causing the anchor blade 14 to splay either outward or inward depending on the rotation of the activation instrument. The splay unit 74 allows for continuously variable blade splay and will actuate for example to allow for −20° to 25° (up to 45° total) of angular splay. The freedom of the anchor blade to pivot relative to the arm initially allows the angle of the blades relative to each other and relative to the spine to be adjusted while the blades are anchored to the bone anchors without, the adjustment acting on the spine itself (e.g. compression or distraction). The clutch also facilitates coupling of the blade to the arm by providing extra alignment tolerance. Markings aligning with the recess 68 sidewall and the flange 236 sidewall may provide visual indication of the state of the clutch (i.e. engaged or unengaged).

The right arm 30 includes a proximal segment 88 and a distal segment 90. The proximal segment 88 includes an aperture 92 configured to fixedly receive the second rack 26 such that the second rack 26 and proximal segment 88 are generally perpendicular to one another. Thus, translation of the second rack 26 in either direction causes a corresponding movement of the right arm 30 in the same direction.

The distal segment 90 is connected to the proximal segment 88 and is configured to releasably engage the second anchor blade 16. The distal segment 90 includes a generally cylindrical housing 94 having a distal face 96. The distal face 96 includes a central post 98 protruding distally from the center of the distal face 96 and a pair of opposing recesses 100 positioned on the perimeter of the distal face 96 on either side of the central post 98. The central post 98 is configured to mate with the attachment aperture 232 of the anchor blade 16 to securely attach the anchor blade 16 to the right arm 30. The central post 98 is generally cylindrical and includes a tapered leading end 102 and a circumferential recess 104 positioned between the leading end 102 and the distal face 96. The housing 94 is able to rotate, thus causing the anchor blade 16 to rotate and effect tissue distraction. This rotation is independent of the first anchor blade 14, and controlled by a splay unit 106 (FIGS. 6-8). The splay unit 106 includes a flange 108 extending laterally away from the housing 94, a threaded jack screw 110, and a cap 112. The jack screw 110 is pivotably secured to the flange 108 via a post 114. The cap 112 includes a threaded central aperture 116 and an engagement recess 118 for receiving a distal end of an activation instrument (not shown) such as a T-handle (for example). As the cap 112 is rotated by the activation instrument, it translates (in either direction depending on the direction of rotation of the instrument) along the jack screw 110. This causes the jack screw 110 to pivot about the pin 114, which in turn causes the cap 112 to transfer a torque to the housing 94, and more specifically the opposing recesses 100. The recesses 100 cooperate with the flanges 236 of the anchor blade 14 and act as a clutch. That is, the recesses 100 (e.g. clutch cavities) receive the flanges 236 (e.g. clutch extensions) when the blade and arm are coupled. The recesses 100 are wider than the flanges 236 such that the flange can rotate within the recess a limited amount until a sidewall of the flanges engages a sidewall of the recess (e.g. the clutch is engaged). Once the clutch is engaged the anchor blade will no longer pivot relative to the arm and will instead rotate (splay) with the arm, thus causing the anchor blade 14 to splay either outward or inward depending on the rotation of the activation instrument. The splay unit 74 allows for continuously variable blade splay and will actuate for example to allow for −20° to 25° (up to 45° total) of angular splay. As described previously, the freedom of the anchor blade to pivot relative to the arm initially allows the angle of the blades relative to each other and relative to the spine to be adjusted while the blades are anchored to the bone anchors without, the adjustment acting on the spine itself (e.g. compression or distraction). The clutch also facilitates coupling of the blade to the arm by providing extra alignment tolerance. Markings aligning with the recess 100 sidewall and the flange 236 sidewall may provide visual indication of the state of the clutch (i.e. engaged or unengaged).

Figure 9:
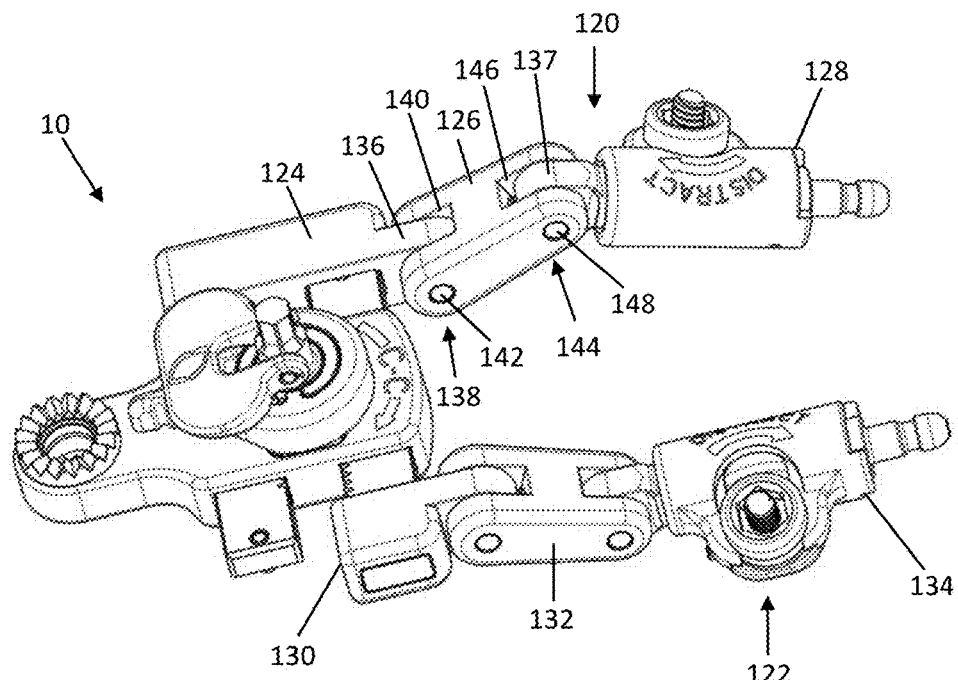
FIG. 9 is a perspective view of an alternative example of an access retractor body forming part of the retractor assembly of FIG. 1 according to one embodiment.
Figure 10:
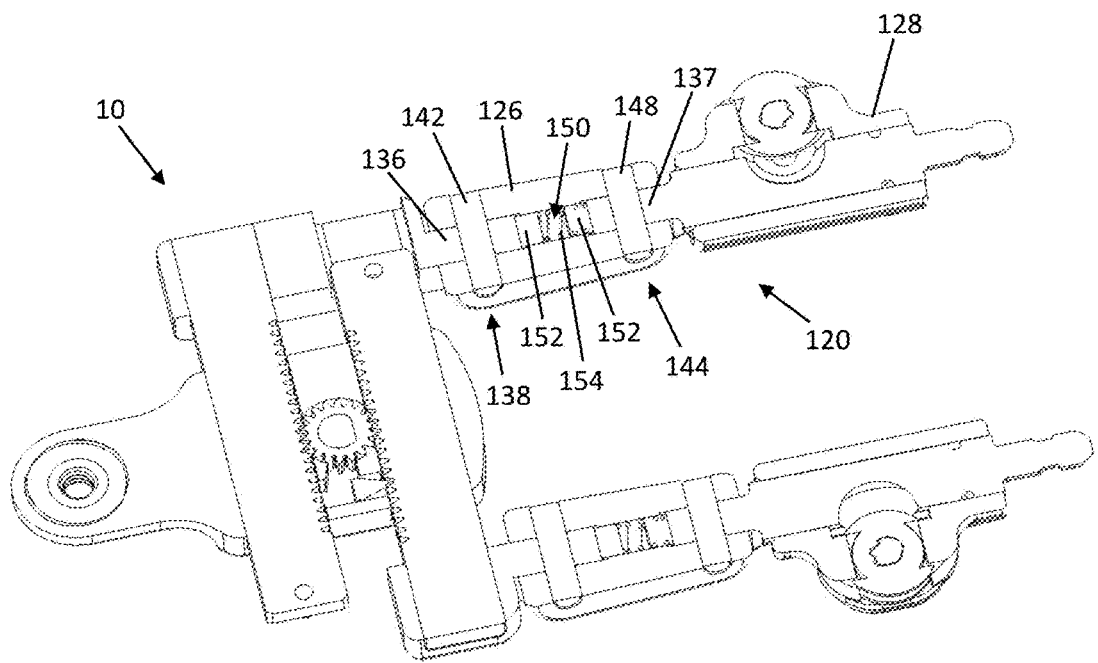
FIG. 10 is a sectional view of the access retractor body of FIG. 9.

Optionally, as depicted in FIGS. 9 and 10, the access retractor body may be provided with moveable arms 120, 122. Providing the retractor 10 with moveable arms 120, 122 may allow for the access retractor body 12 to be raised off the patient's skin level to avoid anatomical challenges that might otherwise cause the access retractor body 12 to dig into the patient's skin, as well as to potentially maneuver the access retractor body 12 out of the fluoroscopy zone. Each moveable arm includes a middle segment positioned between proximal and distal arm segments such as those described above. For example, the left moveable arm 120 includes a proximal segment 124, a middle segment 126, and a distal segment 128. The right moveable arm 122 includes a proximal segment 130, a middle segment 132, and a distal segment 134. In the interest of expediency, the moveable arm feature will be described in detail with respect to one arm only. However it is to be understood that the moveable arms 120, 122 are virtually identical to one another and thus any feature disclosed may be attributed to either moveable arm.

The proximal segment 124 of the moveable arm 120 includes all of the features previously described in relation to the proximal segment 54 of the left arm 28 described above, and further includes a pivot member 136 extending distally from the proximal segment 124, the pivot member 136 configured to be received within a proximal recess 140 formed in the proximal end 138 of the middle segment 126, as described below. The distal segment 128 of the moveable arm 120 includes all the features previously described in relation to the distal segment 56 of the left arm 28 described above, and further includes a pivot member 137 extending proximally from the distal segment 128, the pivot member 137 configured to be received within a distal recess 146 formed in the distal end 144 of the middle segment 126, as described below.

The middle segment 126 is pivotally connected to both the proximal segment 124 and the distal segment 128. The middle segment 126 has a proximal end 138 including a proximal recess 140 configured to receive the pivot member 136 of the proximal segment 124. A pin 142 extends through the proximal end 138 and pivot member 136 and provides an axis about which the middle segment 126 pivots relative to the proximal segment 124. The middle segment further has a distal end 144 including a distal recess 146 configured to receive the pivot member 137 of the distal segment 128. A pin 148 extends through the distal end 144 and pivot member 137 and provides an axis about which the distal segment 128 pivots relative to the middle segment 126. The middle segment 126 further includes a friction recess 150 positioned in the middle of the middle segment 126. The friction recess 150 houses a friction element comprising a pair of friction pins 152 separated by a spring 154. The spring 154 exerts a force equally on the friction pins 152 that in turn exerts a frictional force on the pivot members 136, 137. Thus, the friction element allows movement of the middle segment 126 relative to the proximal and distal segments 124, 128 in the presence of sufficient force to overcome the friction. In the absence of such a force, the friction element operates to maintain the position of the middle segment 126 relative to the proximal segment and distal segments 124, 128. The double hinge creates a flexible arm construct such that the arms can pivot about and adjust to eliminate caudal-cranial blade skew issues (encountered when facing difficult patient anatomy).

Figure 3:
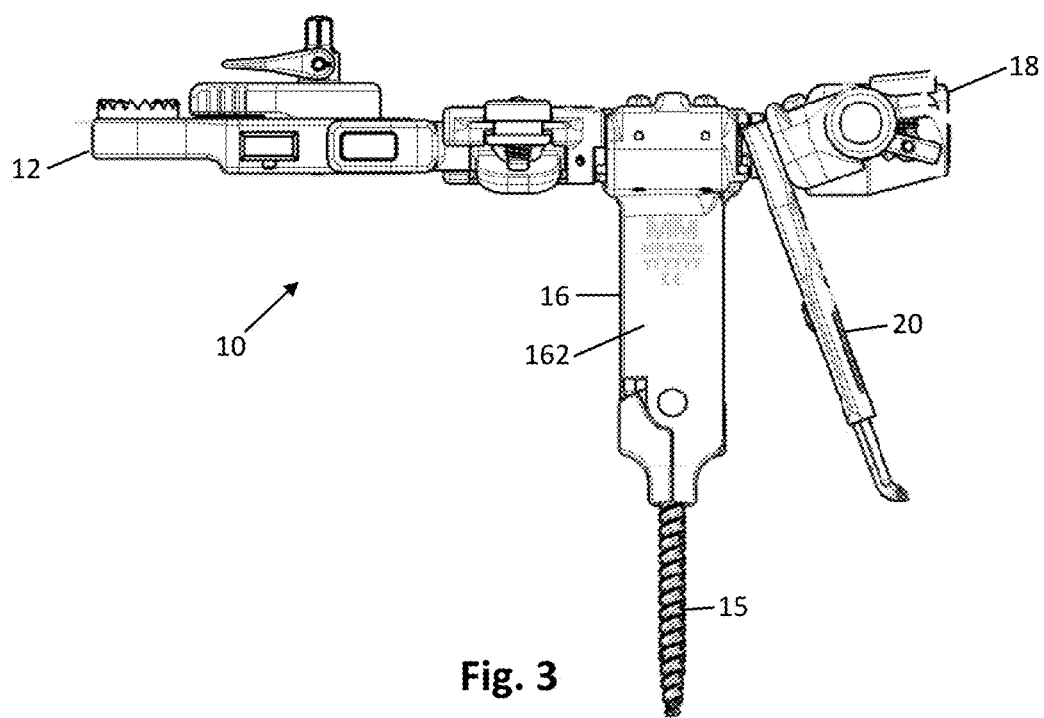
FIG. 3 is a side plan view of the retractor assembly of FIG. 1.
Figure 4:
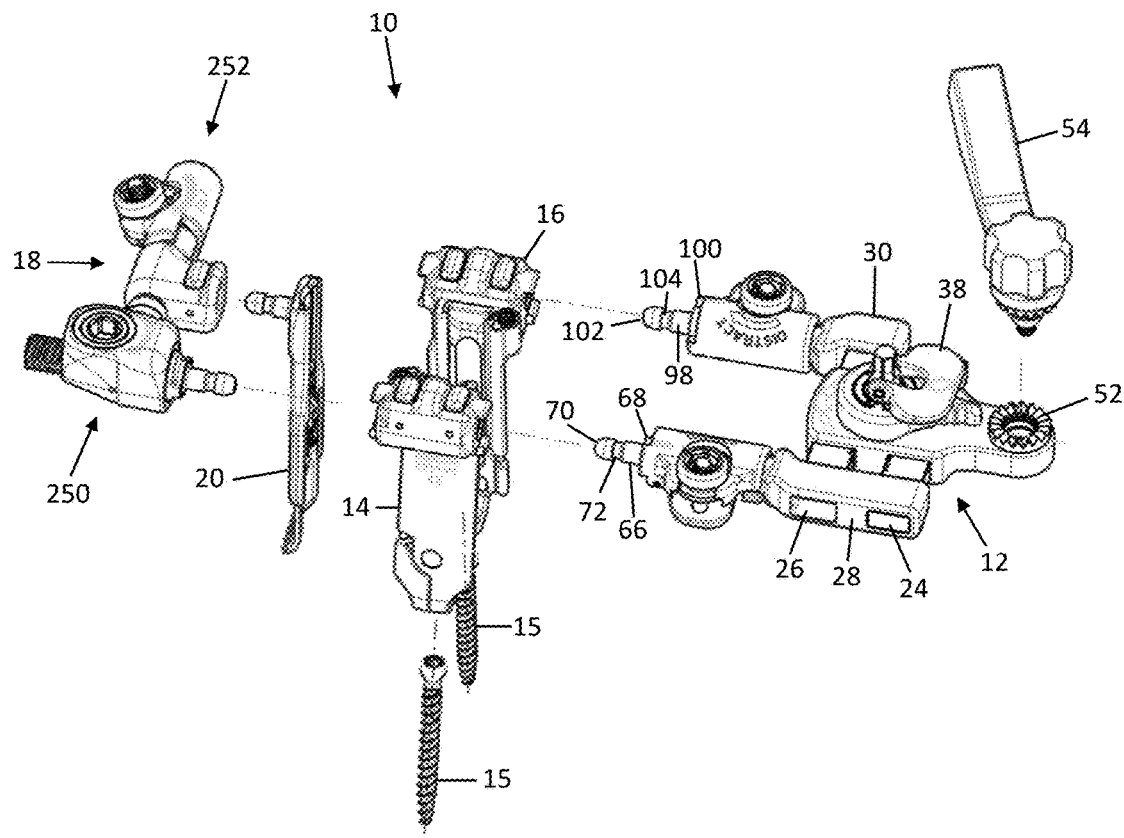
FIG. 4 is an exploded perspective view of the retractor assembly of FIG. 1.

FIGS. 11-17 illustrate the anchor blade 14 in greater detail. Anchor blade 16 is virtually identical to anchor blade 14 in form and function and therefore all features disclosed herein with regard to anchor blade 14 may be attributable to anchor blade 16 as well. Generally, anchor blade 14 has a blade portion 156 extending from a coupler 158. The blade portion 156 has an interior face 160 and an exterior face 162 (FIG. 3). The exterior face 162 is generally smooth and rests against the soft tissue during use. The anchor blade 14 is configured to pivot to effect distraction as discussed previously. The blade portion 156 has a distal end 164 and a proximal end 166.

The distal end 164 includes an integral pivot arm 168 such that the distal end 164 is divided into a static arm 170 and a pivot arm 168. The distal end of the static arm 170 includes a static foot 172 extending therefrom and the distal end of the pivot arm 168 includes a pivot foot 174 extending therefrom. When together in a closed position (FIG. 16), the pivot foot 174 and static foot 172 act in concert to form a capture element (e.g. divided ring) having a center aperture 176 dimensioned to receive a neck 178 of the bone anchor 15 (which also includes a head 180 and a threaded shank 182). A contact surface 184 on the static foot 172 and a contact surface 186 on the pivot foot 174 interface with the generally spherical outer surface of the head 180 of the bone anchor 15 to form a polyaxial joint between the bone anchor 15 and anchor blade 14. The contact surfaces 184, 186 may each have any shape capable of enabling such a polyaxial relationship, including but not limited to angled, rounded, and/or spherically concave. A gap may be provided between the pivot foot and static foot to reduces the amount the pivot arm is required to pivot in order to permit the anchor shank to escape the attachment ring. The footprint of the capture ring is also designed to further facilitating separation from the anchor head during disengagement. The Inside of the ring is curved and angled in such a way so that when the locking shaft is released a force applied to the pivot foot will facilitate the action of opening the pivot foot to permit disengagement from the anchor. The pivot arm 168 is pivotably attached to the distal portion 164 of the anchor blade 14 by a pin 190 that extends through a pivot aperture 192 on the proximal end of the pivot arm 168 and a corresponding pivot aperture 194 on the distal portion 164 of the anchor blade 14. The pivot arm 168 rotates in a plane parallel to the width of the anchor blade 14 such that the pivot foot 174 can be separated from the static foot 172 to permit passage of the screw shank, allowing the anchor blade to be disengaged from the bone anchor 15 after tulip coupling. A lateral recess 194 is formed in the pivot foot 174 and is configured to receive a stabilization flange 196 therein. The stabilization flange 196 extends away from the static foot 172 into the lateral recess 194 to ensure the pivot foot 174 remains in the desired plane of motion.

The anchor blade 14 further includes an enclosed channel 198 positioned on one side of the anchor blade 14 and extending the length of the blade. A locking shaft 200 extends through the enclosed channel 198 and engages the pivot arm 168 to maintain the pivot foot 174 (and capture element) in a closed position. This engagement is controlled by an actuator, for example a setscrew 202, that is engaged by a user to actuate the locking shaft 200. The setscrew 202 includes a threaded body 204, a distal shelf 206, and a tool recess 208. The threaded body 204 is generally cylindrical and configured to engage a threaded recess 210 on the proximal end 166 of the anchor blade 14. The distal shelf 206 interacts with a proximal tab 212 on the locking shaft 200 in such a way that when the setscrew 202 is rotated, accordingly the distal shelf 206 exerts a downward force on the proximal tab 212, causing the locking shaft 200 to advance distally through the enclosed channel 198 and engage the pivot arm 168. A capture ring 214 is provided to prevent the setscrew 202 from backing out of the threaded recess 210. The tool recess 208 is configured to receive a distal end 216 of a retractor 218 that is used to actuate the setscrew 202. Although described herein as a setscrew 202, the actuator may be any element that a user may use to cause movement of the locking shaft 200, including but not limited to a cam mechanism and the like. The anchor blade 14 further includes a track 220 that slidably receives various instruments (e.g. shank/blade inserter, tulip inserter) and light cables.

The coupler 158 is integrally formed with the proximal portion 166 of the anchor blade 14 and provides a spring-loaded quick connect and release mechanism for engagement with the central post 66 of the left arm 28 (and/or the central post 98 of the right arm 30) described above. It should be understood that the anchor blades 14 and 16 are interchangeable in that either anchor blade 14 or anchor blade 16 may be used with either the left arm 28 or right arm 30. Therefore, only the interaction between the anchor blade 14 and the left arm 28 is described in detail herein, however all features herein described also apply to the interaction between the anchor blade 16 and the right arm 30. The coupler 158 has a proximal half 222 and a distal half 224. For the purpose of this disclosure, the proximal half 222 is defined as the portion of the coupler 158 that engages with left retractor arm 28, and the distal half 224 is defined as the portion of the coupler 158 that engages with the secondary retractor 18 (or the right retractor arm, if attached thereto). The proximal half 222 and distal half 224 of the coupler 158 are identical and as such the various features common to both halves will be assigned the same reference numerals for clarity.

The coupler 158 includes a housing 226 and a pair of buttons 228. The housing 226 includes a proximal face 230 on the proximal end 222 (and an identical distal face on the distal end 224), an attachment aperture 232 extending through the proximal face 230, a pair of button apertures 234, and an interior lumen 235. The proximal face 230 includes a pair of flanges 236 extending proximally from the proximal face 230. When the anchor blade 14 is mated to the left arm 28, the proximal face 230 flushly interfaces with the distal face 64 of the left arm, and the flanges 236 engage with the recesses 68 formed in the distal face 64 of the left arm 28 to operated as a clutch, as described above. The attachment aperture 232 receives the central post 66 of the left arm 28 therethrough such that the central post 66 can extend into the interior lumen 235 of the housing 226. The button apertures 234 are configured to allow passage of the buttons 228 into the interior lumen 235. The buttons 228 each have a top surface 238, a through-hole 240, a lower ridge 242, and a bottom post 244. The top surface 238 is generally rounded to maintain a low profile and cause minimal disruption to surrounding anatomy during use, and is provided as a user engagement surface. The through-hole 240 receives the central post 66 therethrough. The lower ridge 242 is configured to nest within the circumferential recess 72 of the central post 66 to prevent egress of the central post 66 during use. The bottom post 244 centers a spring 246 which biases the lower ridge 242 into the circumferential recess 72. During coupling of the anchor blade 14 and the left arm 28, he tapered leading end 70 of the central post 66 enables the central post 66 to overcome the bias and advance until the lower ridge 242 is aligned with the circumferential recess 72, at which point the spring 246 causes the lower ridge 242 to snap into circumferential recess 72. To release the blade 14, the user presses downward on the top surface 238, which forces the lower ridge 242 out of the circumferential recess 72, enabling removal of the central post 60. The buttons 228 are secured to the coupler 158 via pins 245 that nest in recesses 247 on the buttons 228. The coupler 158 may also include alignment markings 248 that act in concert with alignment markings on the arms 28, 30 to provide visual feedback to a user that sufficient distraction is achieved.

The anchor blades 14, 16 transmit torque efficiently to the bone anchor 15 (e.g. for compression/distraction) without any loss of polyaxial (tulip) motion. The anchor blade 14, 16 are reusable. The pivot foot 168 of the anchor blade 14 allows for top down loading of large screws where the shank thread diameter is larger than the diameter of the shank head. The pivot foot 168 will allow a polyaxial tulip to be loaded in top down approach without entrapping the anchoring point of the anchor blades.

Figure 18:
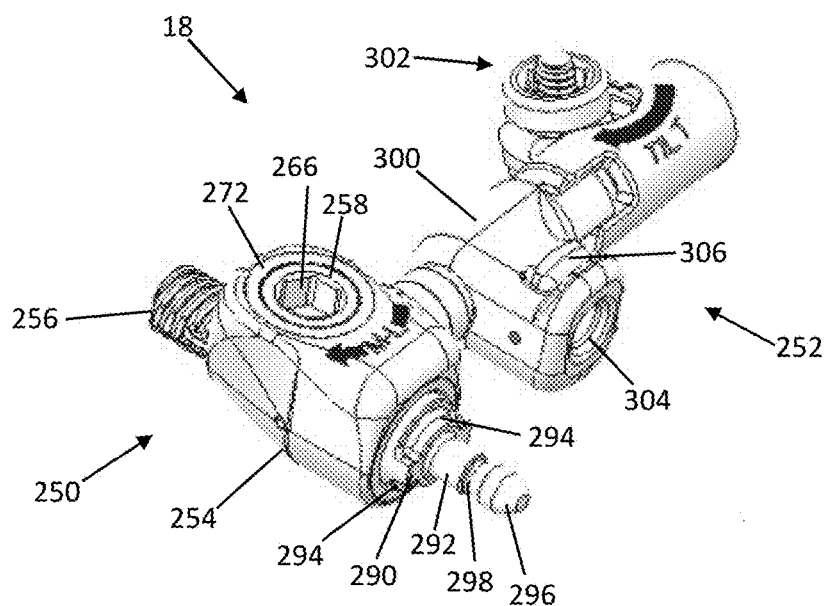
FIG. 18 is a perspective view of an example of a secondary retractor forming part of the retractor assembly of FIG. 1.
Figure 19:
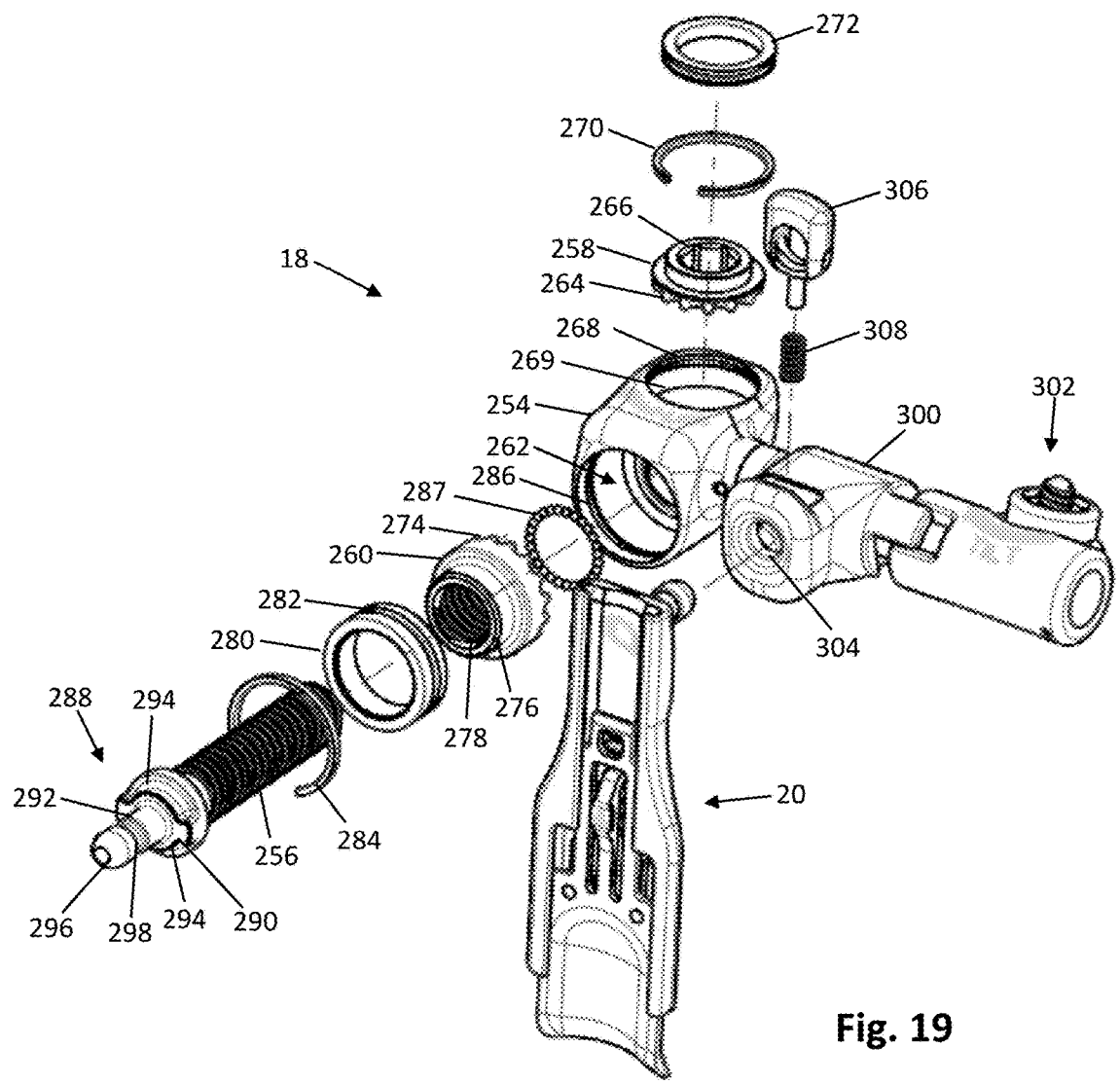
FIG. 19 is an exploded perspective view of the secondary retractor of FIG. 18.

FIGS. 18-19 illustrate an example of a secondary retractor 18 according to one embodiment. With additional reference to FIGS. 4 and 17, the secondary retractor 18 can attach to an assembled retractor 10 and has a self-locking mechanism. The secondary retractor 18 is attachable to the coupler 158 of the anchor blade 14 and comprises a retraction assembly 250 and a blade assembly 252. The secondary retractor 18 allows for further connection to a secondary (e.g. medial) blade 20 and drives further access to the spine medially with many degrees of freedom. For example, the secondary retractor 18 may provide for medial retraction, medial splay, caudal-cranial pivoting and caudal-cranial translation. The retraction assembly 250 provides medial retraction and comprises a housing 254, a threaded shaft 256, and a perpendicular gear comprising an actuating gear 258 and a translation gear 260, rendering fine resolution. The housing 254 has an interior lumen 262 through which the threaded shaft 256 extends and within which the perpendicular gear is contained. The actuating gear 258 includes a tooth portion 264 and an engagement recess 266. The engagement recess 266 extends through an aperture 268 formed in the housing 254 and provides an engagement element for an actuator tool. The housing 254 has a circumferential recess 269 configured to accept a snap ring 270. The actuating gear 258 is secured to the housing 254 via the snap ring 270 and a grooved retention washer 272. The translation gear 260 is oriented perpendicularly relative to the actuating gear 258. The translation gear 260 includes a tooth portion 274, a post 276, and a threaded interior lumen 278. The tooth portion 274 engages the tooth portion 264 of the actuating gear 258 and causes rotation of the translation gear 260 when the actuating gear 258 is rotated. The post 276 fits within a retaining ring 280, which has a circumferential recess 282 configured to receive a snap ring 284 therein. Snap ring 284 also fits within groove 286 formed within the interior lumen 254 to secure the translation gear 260 to the housing 254. A ball bearing race 287 is provided to prevent galling between the gears during use.

The threaded shaft 256 mates with the threaded lumen 278 of the translation gear 260. As the translation gear 260 rotates, the threaded shaft 256 is caused to translate in either a medial or lateral direction, depending on the direction of the rotation. The threaded shaft 256 further includes a proximal end 288 that is virtually identical in structure and function to the distal face 96 of the first arm 28 described above. To wit, the proximal end 288 includes a proximal face 290, a central post 292 protruding distally from the center of the proximal face 290 and a pair of opposing recesses 294 positioned on the perimeter of the proximal face 290 on either side of the central post 292. The central post 292 is configured to mate with the attachment aperture 232 of the anchor blade 14 (or anchor blade 16) to securely attach the anchor blade 14 to the left arm 28. The central post 292 is generally cylindrical and includes a tapered leading end 296 and a circumferential recess 298 positioned between the leading end 296 and the proximal face 290. These features interact with the quick release mechanism of the anchor blade 14 described above in a manner that is identical to the manner in which the corresponding structure of the left retractor arm 28 interacts with the quick release mechanism of the anchor blade 14, and thus a repeat discussion is unnecessary. It should be noted, however that in the example disclosed above in which the anchor blade 14 is attached to the left retractor arm 28 via the proximal end 222 of the coupler 158, the secondary retractor 18 may be contemporaneously attached to the distal end 224 of the coupler 158.

The blade assembly 252 extends generally perpendicularly from the retraction assembly 250 and includes a quick release housing 300 and a splay unit 302. The quick release housing 300 includes an attachment aperture 304 for receiving the attachment post 358 of the secondary blade 20 and a button 306 that is biased with a spring 308. The quick release housing 300 is identical to form and function to the same feature described above in relation to the coupler 158, and thus a detailed description of the like features need not be repeated. Similarly, the splay unit 302 is identical in form and function to the splay unit 74 of the left arm 28, and thus a detailed description of the like features need not be repeated. It should be noted however that the splay unit 302 allows for continuously variable blade splay and will actuate for example to allow for up to 40° of angular splay.

Figure 20:
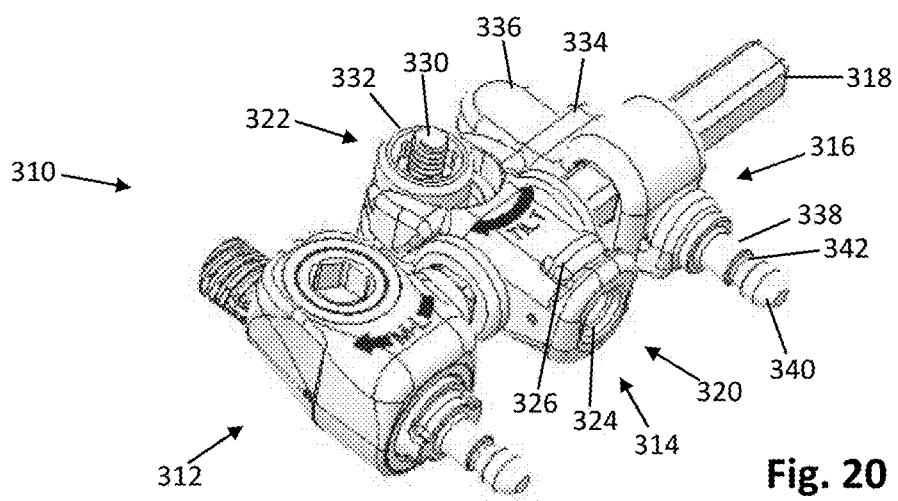
FIG. 20 is a perspective view of an alternative example of a secondary retractor forming part of the retractor assembly of FIG. 1.
Figure 21:
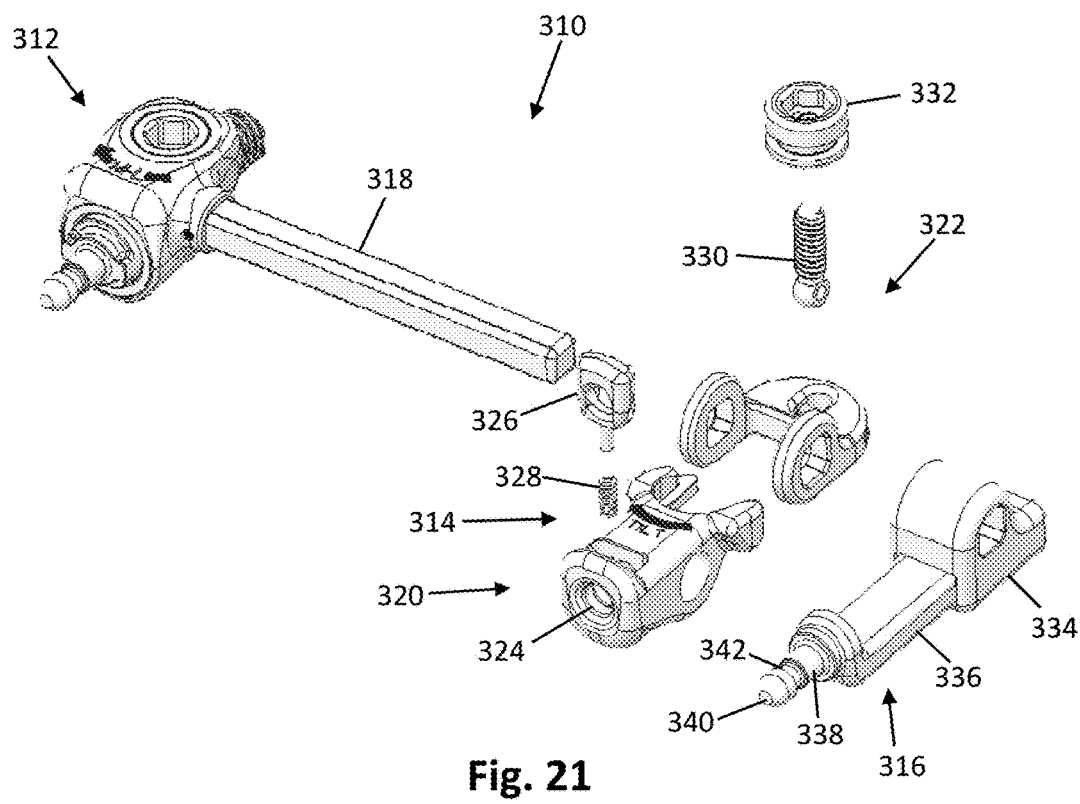
FIG. 21 is an exploded perspective view of the secondary retractor of FIG. 20.
Figure 22:
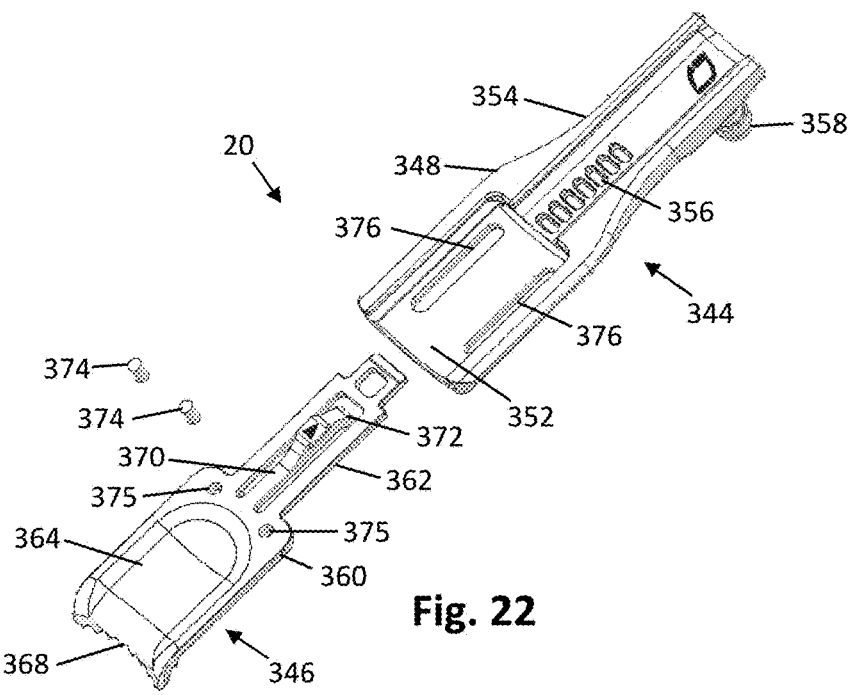
FIG. 22 is an exploded view of a secondary retractor blade forming part of the retractor assembly of FIG. 1.
Figure 33:
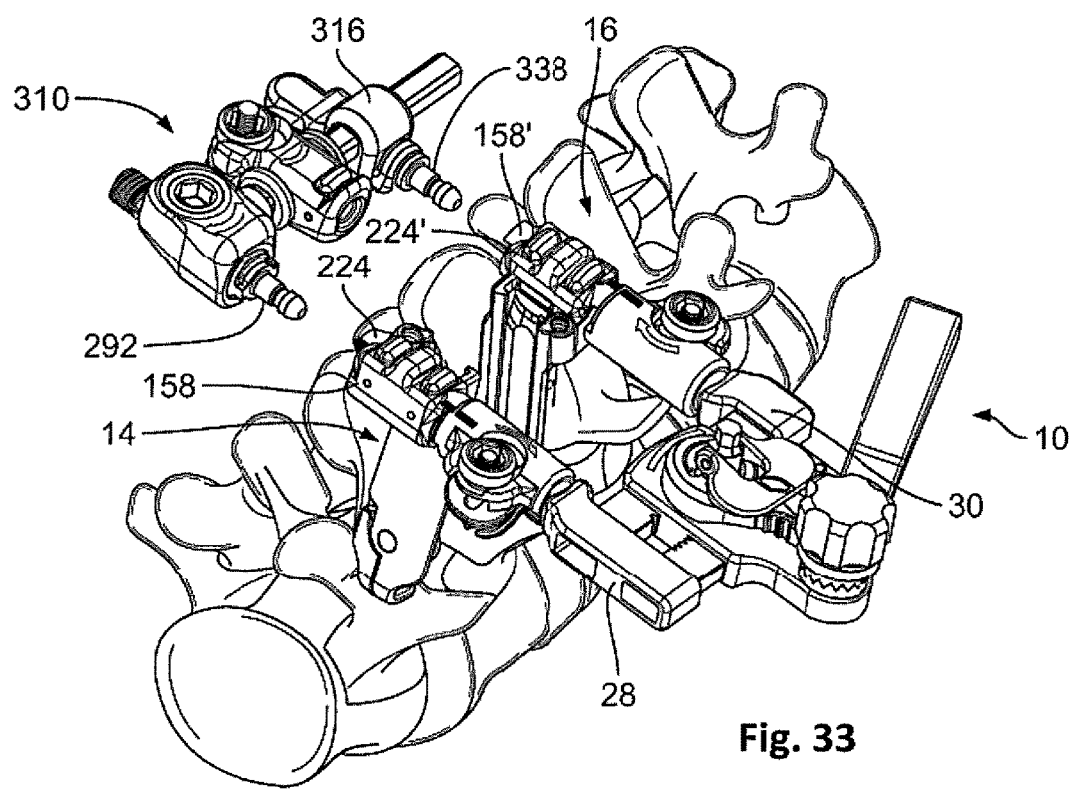
FIG. 33 is a perspective view of the access retractor body and anchor blade assembly juxtaposed with a secondary retractor of FIG. 20, comprising another step in the example method of using the retractor assembly of FIG. 1.
Figure 34:
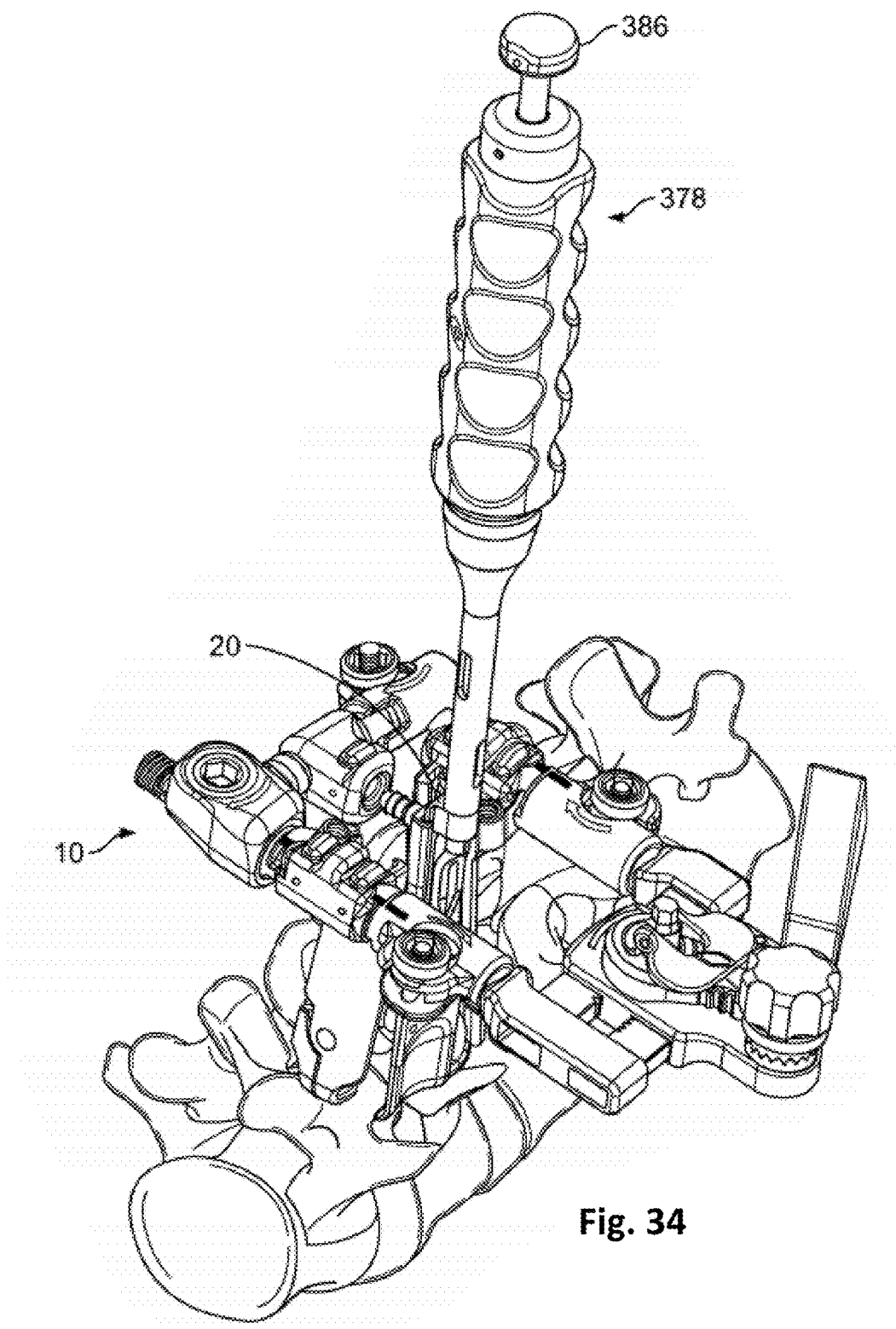
FIG. 34 is a perspective view of the access retractor body, anchor blade, and secondary retractor assembly juxtaposed with the secondary blade-inserter combination of FIG. 26, comprising another step in the example method of using the retractor assembly of FIG. 1.
Figure 35:
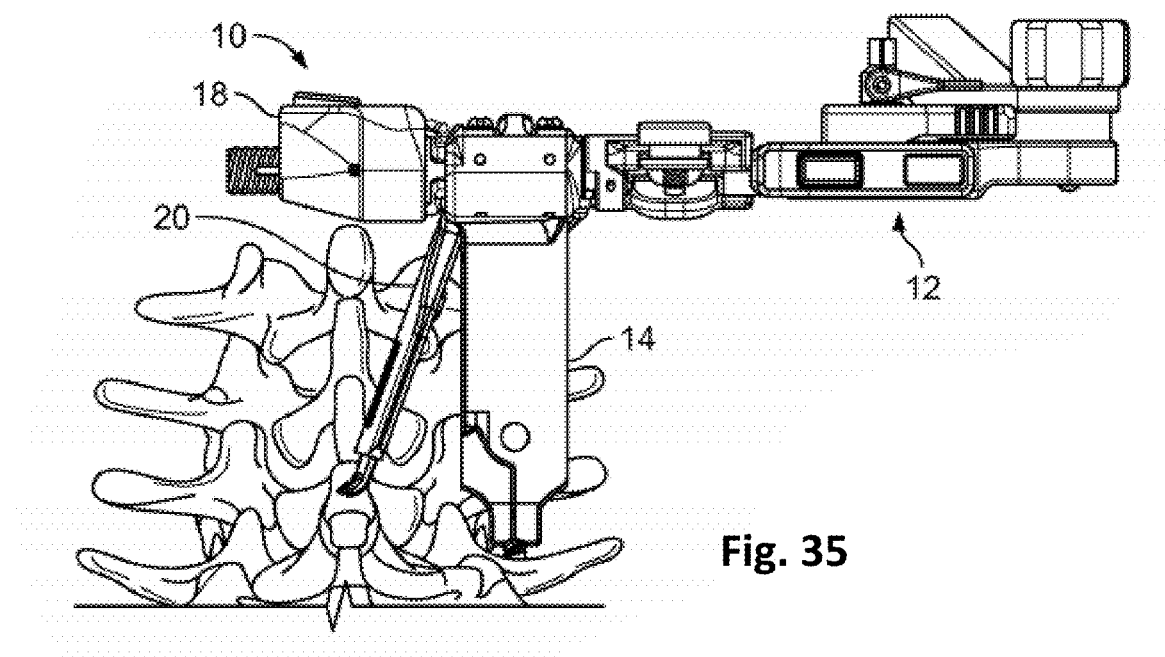
FIGS. 35-37 are side plan and perspective views of the retractor assembly of FIG. 1 in a final assembled position according to one example method.
Figure 36:
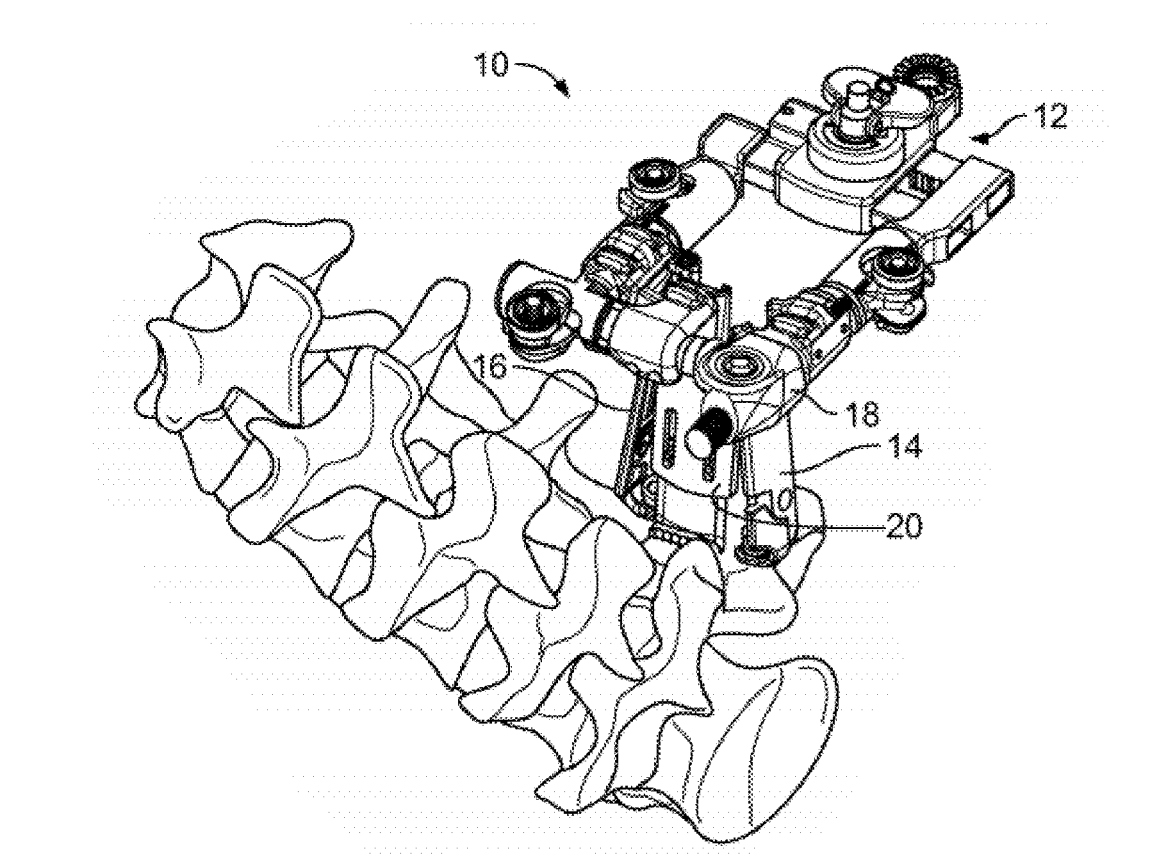
Figure 37:
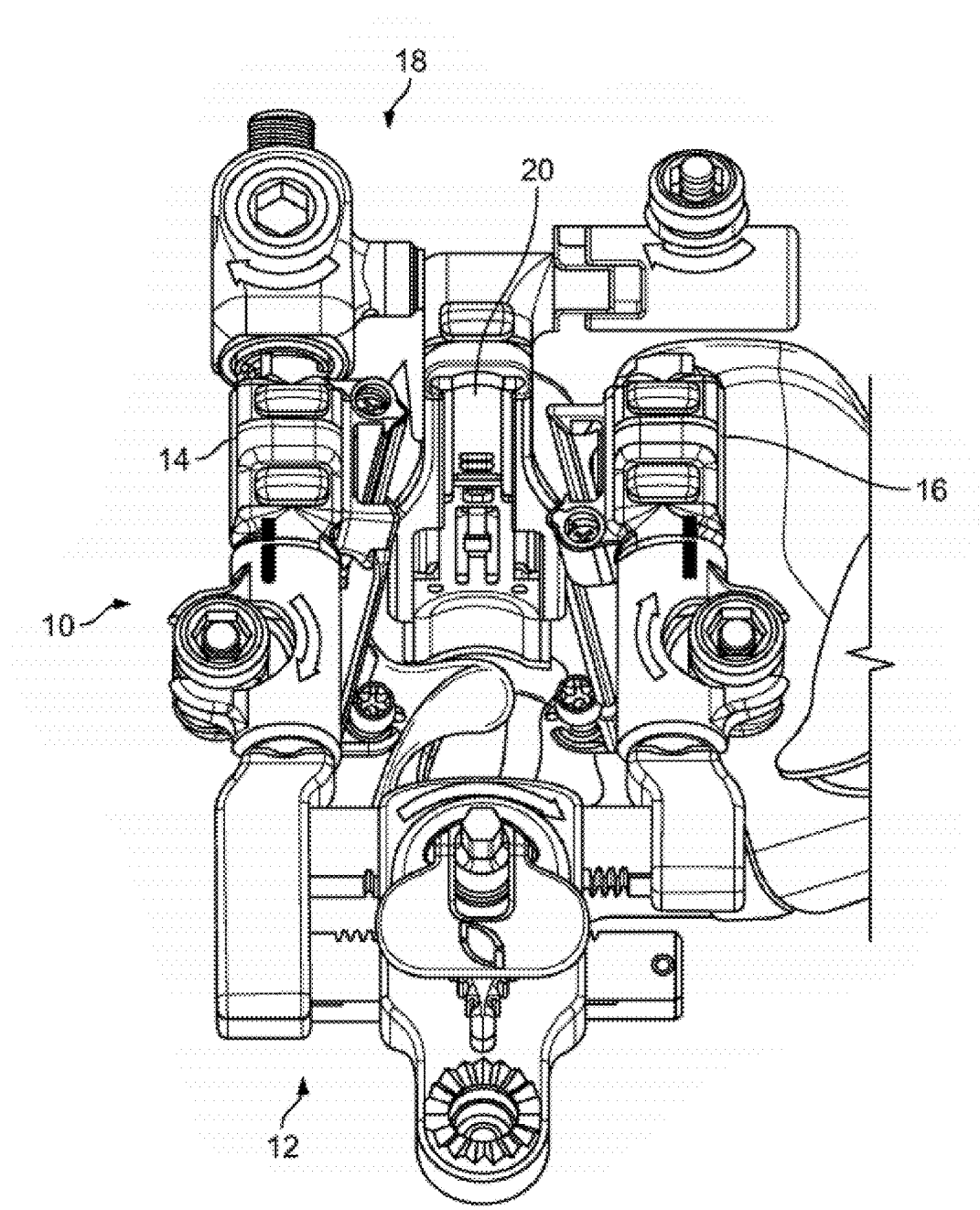

FIGS. 20-21 illustrate an example of a secondary retractor 310 according to another example embodiment. The secondary retractor 310 differs from the secondary retractor 18 described above in that secondary retractor 310 attaches to both the left retractor arm 28 (via anchor blade 14) and the right retractor arm 30 (via anchor blade 16). The secondary retractor 310 is attachable to the coupler 158 of the anchor blade 14 and a corresponding coupler 158' of the anchor blade 16 (FIG. 33). The secondary retractor 310 comprises a retraction assembly 312, a blade assembly 314, and a second attachment unit 316. The secondary retractor 310 allows for further connection to a secondary (e.g. medial) blade 20 and drives further access to the spine medially with many degrees of freedom. For example, the secondary retractor 310 may provide for medial retraction, medial splay, caudal-cranial pivoting and caudal-cranial translation. The retraction assembly 312 is identical to the retraction assembly 250 described above and thus any feature disclosed in relation to retraction assembly 250 is applicable to the retraction assembly 312, rendering a repeat discussion unnecessary. A crossbar 318 extends generally perpendicularly from the retraction assembly 312 terminates at the second attachment unit 316. The blade assembly 314 is positioned on the crossbar 318 between the retraction assembly 312 and the second attachment unit 316. The blade assembly 314 includes a quick release housing 320 and a splay unit 322. The quick release housing 320 includes an attachment aperture 324 for receiving the attachment post 358 of the secondary blade 20 and a button 326 that is biased with a spring 328. The quick release housing 320 is identical in form and function to the same feature described above in relation to the coupler 158, and thus a detailed description of the like features need not be repeated. Similarly, the splay unit 322 is identical in form and function to the splay unit 74 of the left arm 28, including a captured jackscrew 330 and a cap 332 and thus a detailed description of the like features need not be repeated. It should be noted however that the splay unit 322 causes pivoting of the quick release housing 320 (and thus the secondary blade 20) but does not cause rotation of the crossbar 318 or the second attachment unit 316. The splay unit 322 allows for continuously variable blade splay and will actuate for example to allow for up to 40° of angular splay.

The second attachment unit 316 includes a base 334, an extension 336, and an attachment post 338. The attachment post 338 is generally cylindrical and includes a tapered leading end 340 and a circumferential recess 342 positioned between the leading end 340 and the extension 336. These features interact with the quick release mechanism of the anchor blade 16 described above in a manner that is identical to the manner in which the corresponding structure of the left retractor arm 28 interacts with the quick release mechanism of the anchor blade 14, and thus a repeat discussion is unnecessary.

FIGS. 22-26 illustrate a secondary retractor blade (e.g. medial blade) 20 in greater detail. The secondary retractor blade 20 includes proximal track portion 344 and a distal blade portion 346. The proximal track portion 344 has an inner face 348 and an outer face 350. The inner face 348 includes a recess 352 for nesting with at least a portion of the distal blade portion 346. The track portion 344 further includes a track 354 for receiving a light cable (for example) and a plurality of ratchet apertures 356 positioned along the track portion 344 proximally of the recess 352. The outer face 350 includes an attachment post 358 extending generally perpendicularly away from the outer face 350. The attachment post 358 is identical in form and function to the central post 66 of the left retractor arm 28, and interacts with the quick release mechanism 320 of the secondary retractor 310 in the same manner that the central post 66 of the left retractor arm 28 interacts with the quick release mechanism of the coupler 158. The distal blade portion 346 includes a blade 360 and a guide flange 362. The blade 360 includes an inner face 364, an outer face 366, and a serrated foot 368 at the distal tip. The inner face 364 may include a slightly concave surface. The serrated foot 368 curves toward the outer surface 366 and helps minimize tissue creep effect. The guide flange 362 engages with the track 354 to couple the distal blade portion 346 to the proximal track portion 344. The guide flange further includes a cantilever ratcheting mechanism 370 having a proximal end 372 that interacts with the apertures 356 to maintain a desired length of the blade construct. Guide pins 374 extend through pin apertures 375 in the distal blade portion 346 and into guide tracks 376 to ensure the distal blade portion 346 maintains proper alignment during use.

FIGS. 23-26 illustrate the coupling of the secondary blade 20 to a blade inserter 378. The blade inserter 378 includes a proximal handle 380 and a distal tip 382 separated by an elongated shaft 384. The proximal handle 380 includes a release button 386 extending proximally therefrom. The distal tip 382 includes a side edges 384 that mate with the track 354 on the proximal track portion 344 to couple the secondary blade 20 to the blade inserter 378. The distal tip 382 further includes a cantilever ratcheting mechanism 386 having a distal end 388 that interacts with the apertures 356 to maintain a secure hold on the secondary blade 20.

To use the secondary blade 20, first the blade 20 is coupled to the inserter 378 as described above. It should be noted that the distal blade portion 346 should be initially placed in a fully extended position (i.e. positioned such that the distal end 372 of the cantilever ratchet mechanism 370 engages the distal-most ratchet aperture 356 on the proximal track portion 344. The secondary blade 20 is then manually advanced into the surgical target site by the user. The distal tip of the blade 20 may be placed first with haptic feedback in the desired location and then subsequently compressed and connected to the secondary retractor 18. Optionally, the user may use the secondary blade 20 like a Cobb instrument to elevate the tissue at the distal tip. Blade compression (or lengthening if necessary) is achieved as follows: once the blade engages with an anatomical structure (e.g. soft tissue, bone), the distal end will stop moving. If the user continues to apply a downward force on the insertion instrument, the cantilever ratcheting mechanism 386 will cause the distal end 388 to vacate one ratchet aperture 356 for the next proximal ratchet aperture 356 and so on, until the desired blade compression is achieved. The user than maneuvers the secondary blade 20 so that it connects to the secondary retractor 18 via the features described above. If desired, the user may affect blade splay while the inserter is still attached, or after it has been disengaged. Further blade compression may occur during blade splay. Once the secondary blade has been inserted, the release button 386 may be used which causes the cantilever ratcheting mechanism 386 to re-engage the ratchet apertures 356 while providing downward force to the distal blade 346, enabling the inserter 378 to be removed from the surgical wound while contemporaneously allowing the secondary blade 20 to maintain an extended state. By way of example, the distal blade portion 346 of the secondary blade 20 may be made of a titanium material selection that provides for intraoperative fluoroscopy radiolucency.

Figures 27, 28:
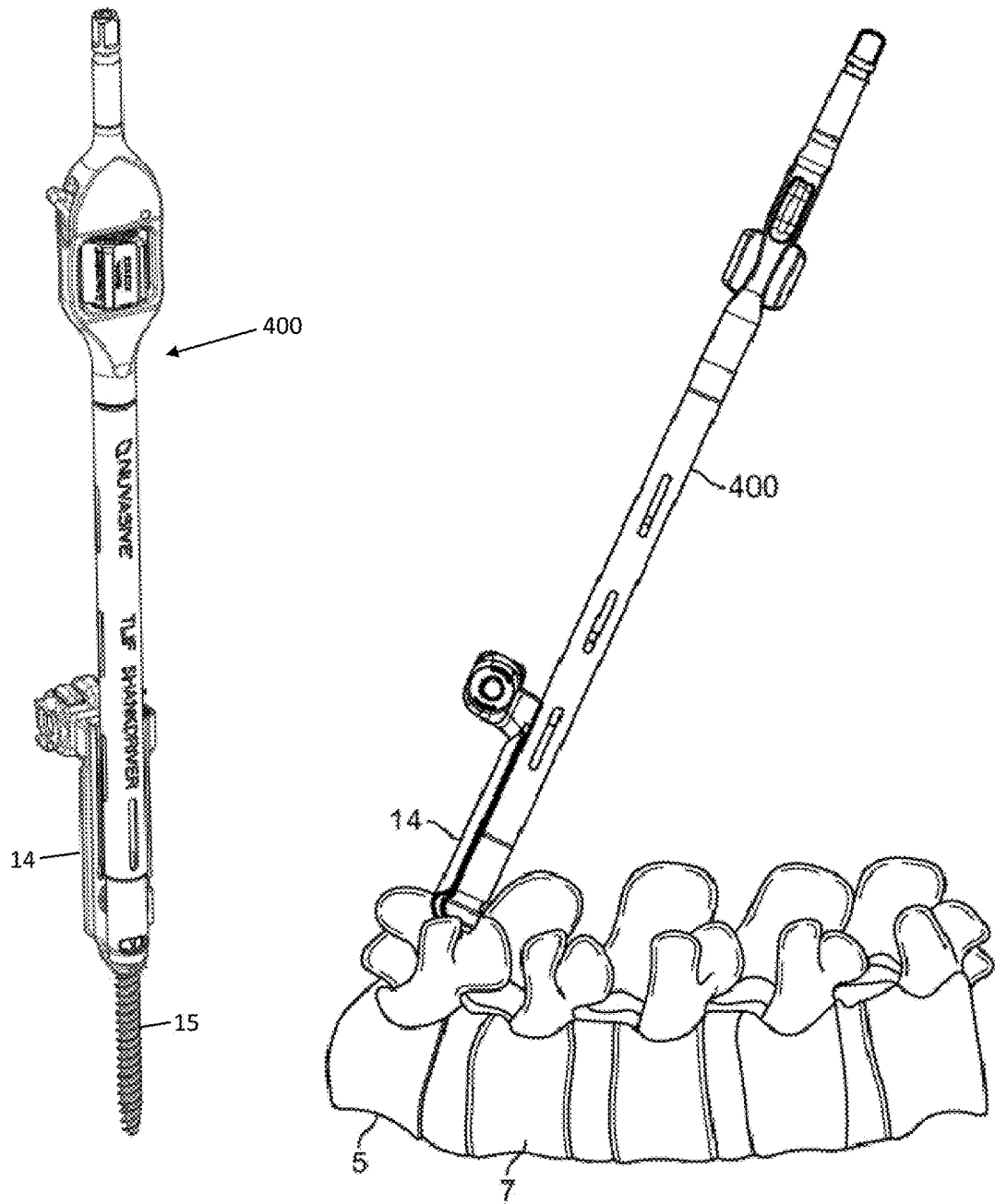
FIG. 27 is a perspective view of an anchor blade of FIG. 11 coupled to a bone anchor, which is coupled to an inserter, comprising one step in an example method of using the retractor assembly of FIG. 1.
FIG. 28 is a plan view of the anchor blade, bone anchor, and inserter combination of FIG. 27 in use to implant the bone anchor in a vertebra, comprising another step in the example method of using the retractor assembly of FIG. 1.
Figure 29:
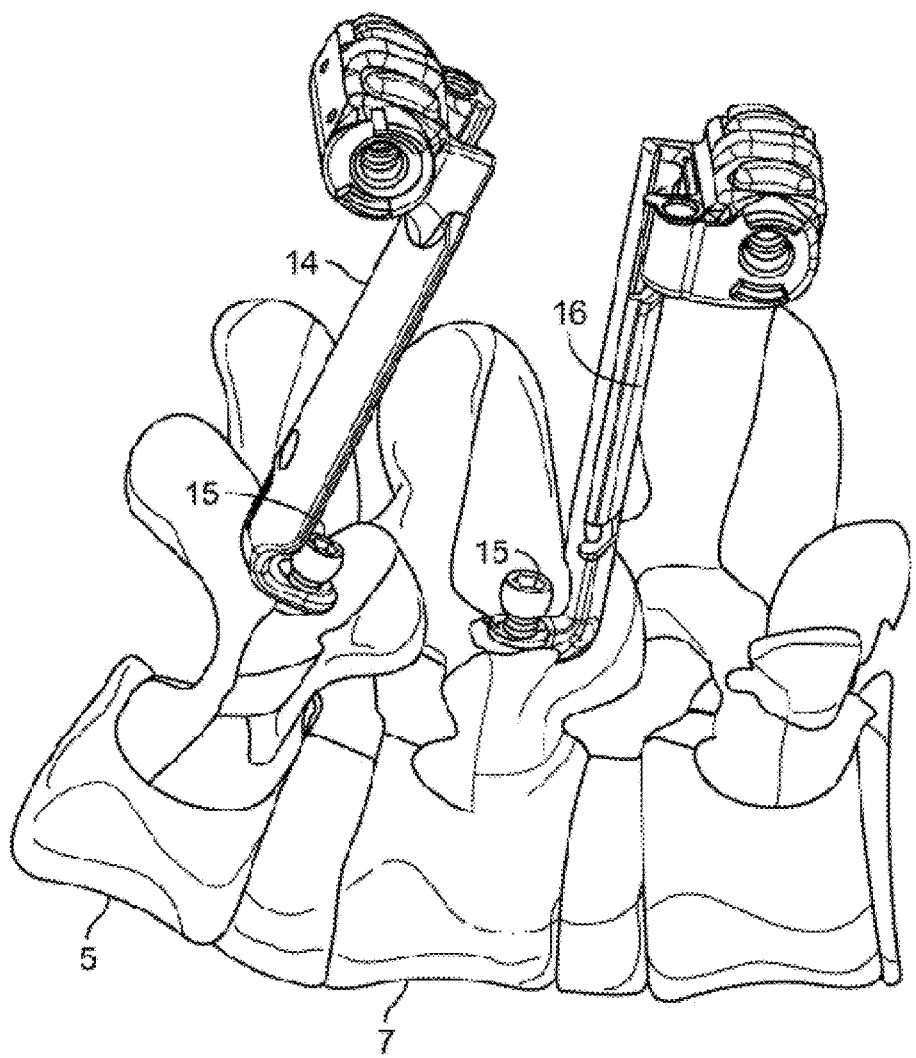
FIG. 29 is a perspective view of a pair of anchor blades of FIG. 11 positioned against adjacent vertebrae, comprising another step in the example method of using the retractor assembly of FIG. 1.

FIGS. 27-38 illustrate an example method of using the retractor 10 of the present disclosure in a TLIF procedure. A beneficial feature of the retractor assembly 10 described herein is that the bone anchor 15 may be coupled to the anchor blades 14, 16 prior to introduction into the surgical target site. This is done by first unlocking the pivot foot 168, inserting the neck 178 of the bone anchor 15 into the center aperture 176, and then relocking the pivot foot 168 as described above (FIGS. 12-13). The bone anchor 15 is now coupled to the anchor blade 14, and now may also be coupled to a driver instrument 400 (FIG. 27) prior to advancement through the operative corridor. Once the patient has been properly positioned, the target area has been identified and exposure has been established, the bone anchors 15 may be placed in the first target sites. After tapping the target pedicles, the coupled bone anchor 15, anchor blade 14, and inserter 400 may be advanced over the K-wire to the target site. The anchor 15 is driven into the bone until either the distal end of the driver 400 or the anchor blade 14 bottoms out on bone (FIG. 28). The K-wire may be removed after the threaded shank 182 enters the posterior part of the vertebral body 5. These steps may be repeated to place a second anchor blade 16 coupled with a bone anchor 15 in a pedicle of an adjacent vertebral body 7 (FIG. 29).

Figure 30:
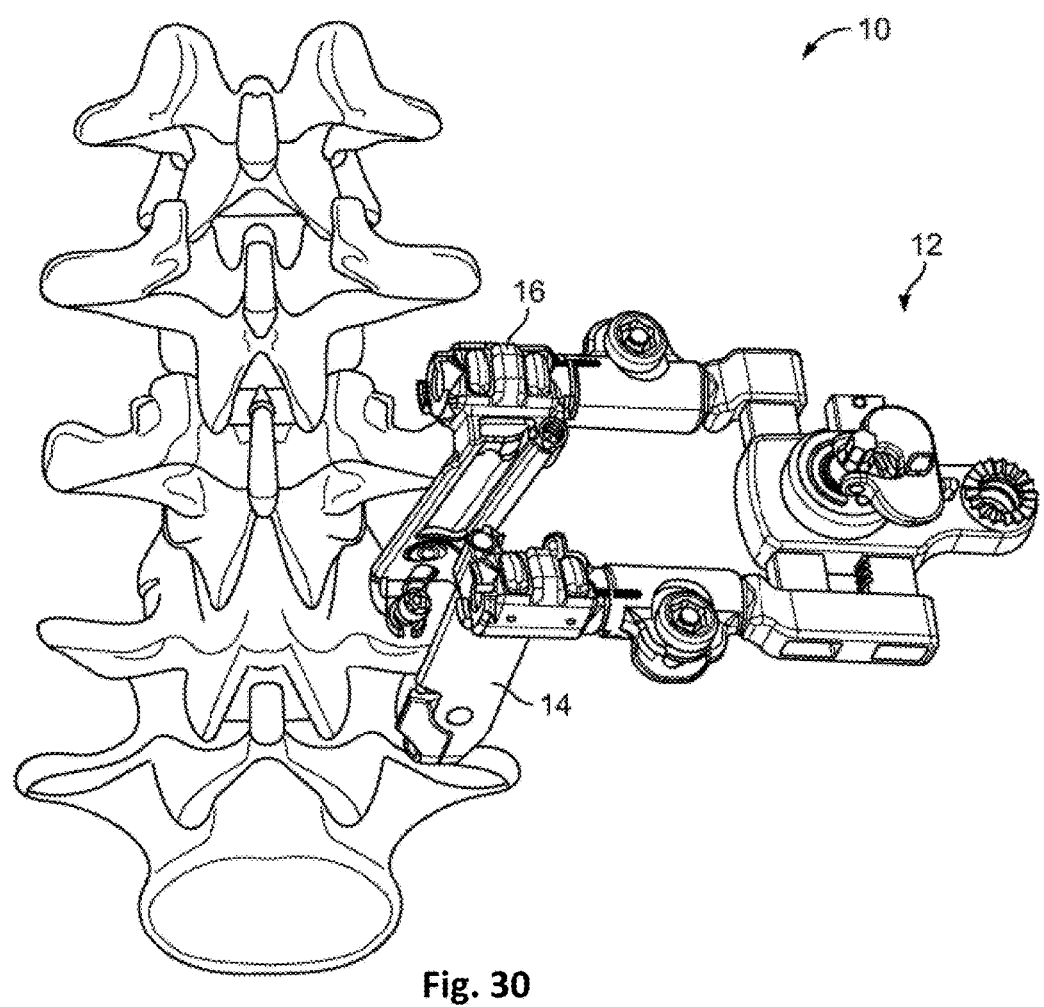
FIGS. 30-31 are a perspective and top plan views, respectively, of the anchor blades of FIG. 29 with the access retractor body of FIG. 5 attached, comprising another step in the example method of using the retractor assembly of FIG. 1.

At this point the access retractor body 12 can be attached to the anchor blades 14, 16 on either side (e.g. medial or lateral), however it can be advantageous to attach the access retractor body 12 to the lateral side of the anchor blades (i.e. away from the patient's spine) so to increase visibility of the target area under fluoroscopy (FIG. 30). As described above, the access retractor body 12 is connected to the anchor blades 14, 16 by inserting the central posts 66, 98 (FIG. 4) into the quick-connect couplers 158 of the anchor blades 14, 16. An audible click will sound when the access retractor body 12 is properly engaged to the blades. At this point the retractor assembly 10 may be attached to a articulating arm (for example) using the articulating arm attachment 52. Positioning the retractor assembly 10 so that the anchor blades 14, 16 are parallel to the disc space ensures the proper medial exposure trajectory is achieved.

Figure 31:
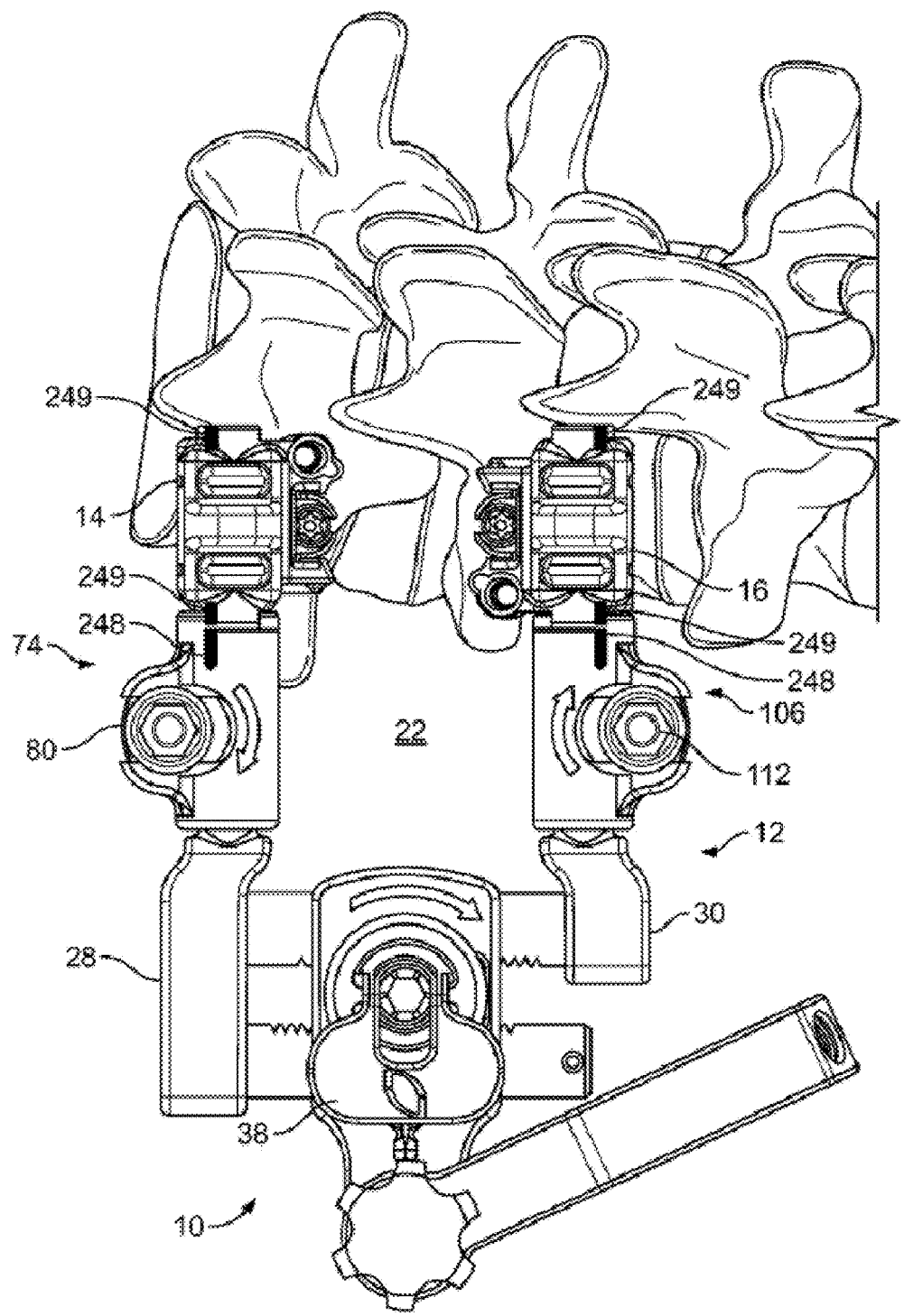
Figure 32:
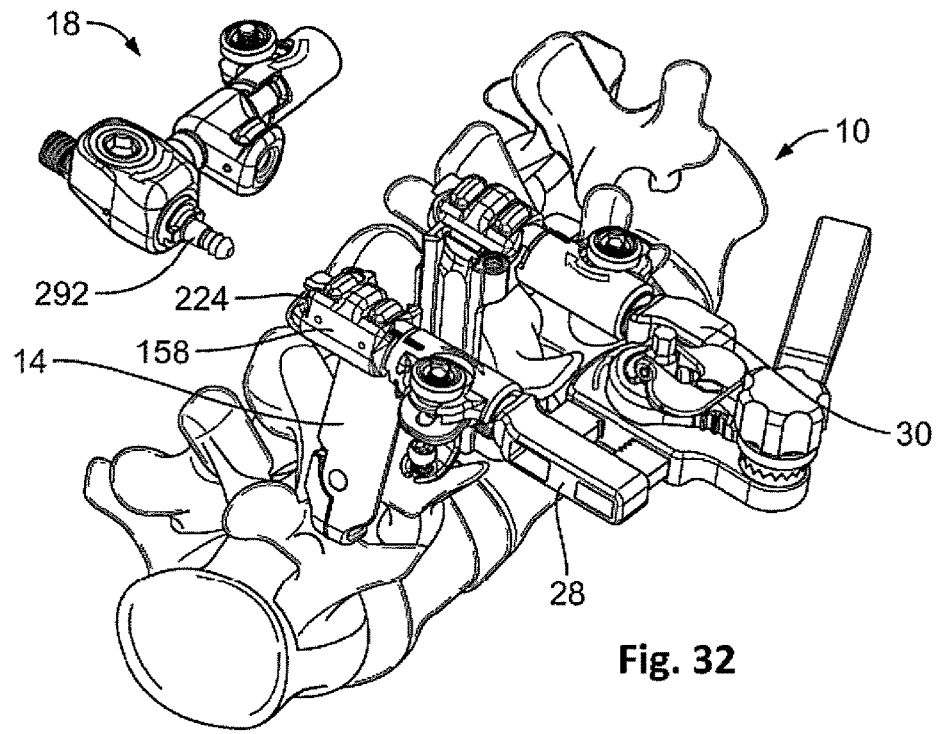
FIG. 32 is a perspective view of the access retractor body and anchor blade assembly juxtaposed with a secondary retractor of FIG. 18, comprising another step in the example method of using the retractor assembly of FIG. 1.

If distraction is desired, the anchor blade 14 may be splayed by using a T-handle (for example) to actuate the cap 80 of the splay unit 74 on the left retractor arm 28 as described above. Similarly, the anchor blade 16 may be independently splayed using a T-handle (for example) to actuate the cap 112 of the splay unit 106 of the right retractor arm 30. Rotation of the T-handles in a clockwise direction causes the blades 14, 16 to splay outward. Since the blades are coupled to the pedicle bones via the bone anchors 15, this will also cause distraction of the disc space. The coupler 158 may include alignment markings 248 that act in concert with alignment markings 249 on the arms 28, 30 to provide visual feedback to a user that sufficient distraction is achieved (FIG. 31). Once proper alignment has been achieved, the user may rotate the thumb tab 38 (or for example a T-handle, if desired) in a clockwise direction to open the retractor and provide soft tissue retraction and initial visualization of the working corridor 22.

Once adequate soft tissue retraction as been achieved, a single-engagement secondary retractor 18 (FIG. 32) or a dual-engagement secondary retractor 310 (FIG. 33) may be added to enable medial retraction. The single-engagement secondary retractor 18 is attached by inserting the central post 292 into the distal half 224 of the coupler 158 of the anchor blade 14. An audible click will sound when the secondary retractor 18 has been properly engaged to the anchor blade 14. The dual-engagement secondary retractor 18 is attached by inserting the central post 292 into the distal half 224 of the coupler 158 of the anchor blade 14, and by inserting the attachment post 338 of the second attachment unit 316 into the distal half 224' of the coupler 158' of the anchor blade 16. Audible clicks will sound when the secondary retractor 310 has been properly engaged to each of the anchor blades 14, 16. A secondary blade 20 is then selected and attached to an inserter 378, and then attached to the secondary retractor 18 as described above with reference to FIGS. 23-26. Once the adequate medial blade retraction and splay has been achieved the release button 386 is pressed on the inserter 378 to release the secondary blade 20 from the inserter 378.

Figure 38:
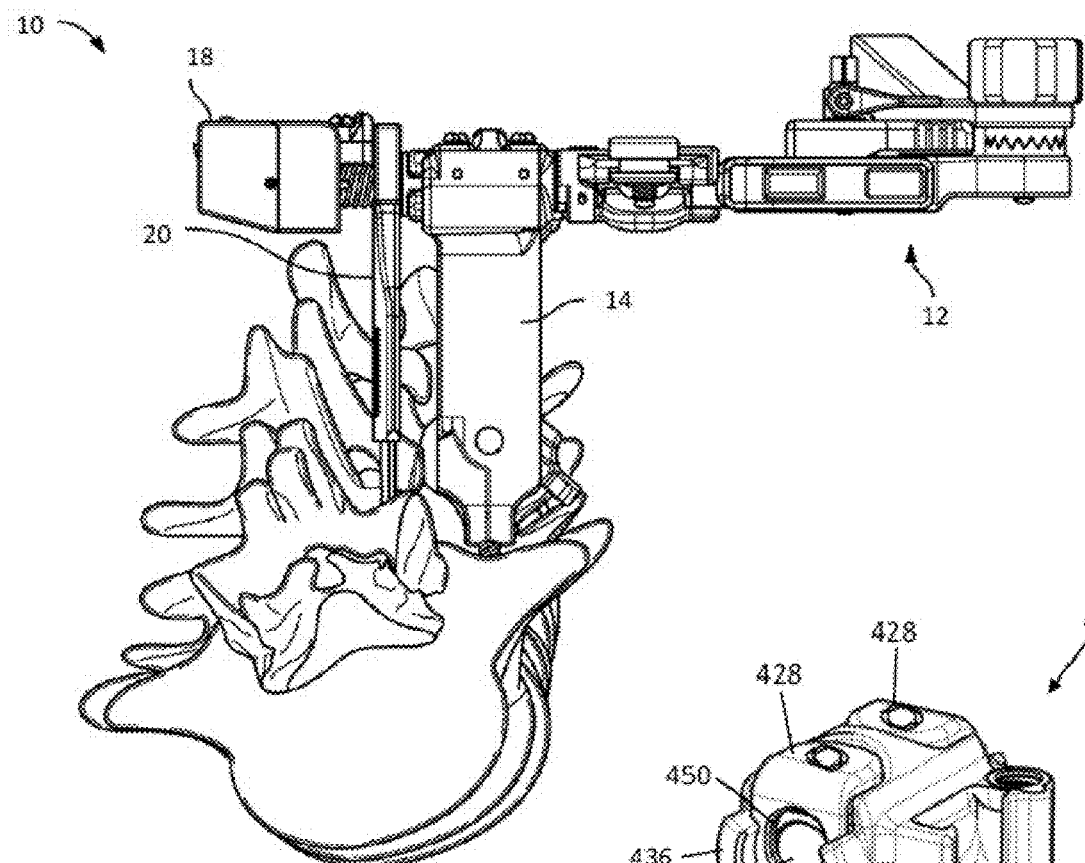
FIG. 38 is a side plan view of the retractor assembly of FIG. 1 in a final assembled position with the secondary blade retracted according to one example method.

FIGS. 35-38 illustrate the final positioning of the retractor assembly 10 relative to the surgical target site. In particular, FIG. 38 illustrates the retractor assembly in use with the secondary blade 20 in a retracted position. From this point the additional steps of the TLIF procedure is carried out at this level including facetectomy, decompression, further distraction (optionally), disc and endplate preparation, and interbody implant insertion. In preparation for rod insertion, a tulip head (not shown) is attached to the bone anchor head while the anchor blades 15, 16 are engaged with the bone anchor 15 at each vertebral level. The rods may also be placed and locked down while the anchor blades 15, 16 are attached. Once the rod construct is sufficiently in place, the pivot foot 168 is unlocked by rotating the setscrew 202 counterclockwise, which causes the locking shaft 200 to retreat proximally through the enclosed channel 198 and thus disengage the pivot arm 168 (FIGS. 11-15). The pivot arm 168 is allowed to move freely, enabling the anchor blade 14 to be dissociated from the bone anchor 15 and removed from the working channel 22. The second anchor blade 16 may be removed from the working channel 22 in the same manner as the anchor blade 14, and the operative wound is closed, completing the procedure.

For multi-level TLIF procedures, the retractor assembly 10 may be used in a "marching technique" to reduce the number of times the pedicles have to be targeted. For example, for a two-level TLIF (involving three adjacent vertebrae), coupled anchor-blade-inserters are placed in each target pedicle (i.e. three blades in total at two adjacent levels). The procedure is performed as described above with relation to one of the levels while the third anchor blade is unattached to anything (except the implanted bone anchor). After the TLIF is completed at the first level, the retractor assembly 10 is removed except for the anchor blades. The first anchor blade is left attached to the bone anchor. The middle blade is rotated 180° and then reconnected to the access retractor body (the other retractor arm), along with the third anchor blade. The TLIF is performed at the second level. Once the tulips are down the rod can be placed connecting all 3 levels and the procedure can then be finished.

Figure 39:
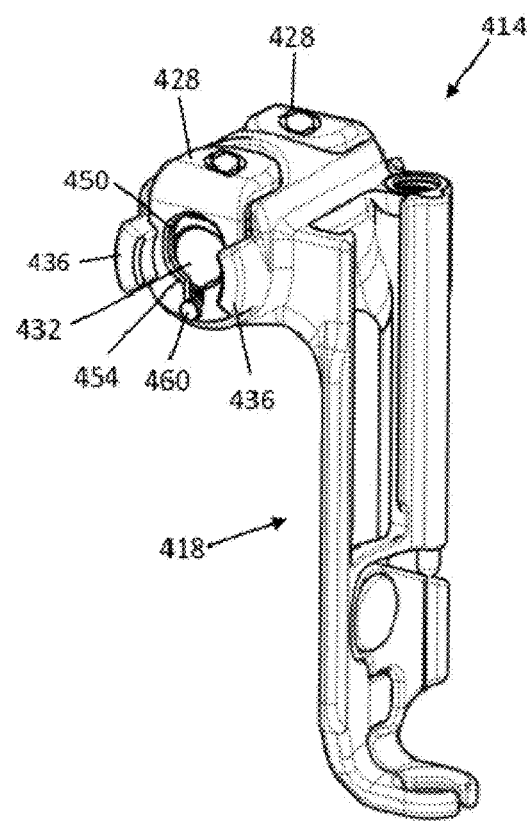
FIG. 39 is a perspective view of another example of an anchor blade forming part of the retractor assembly of FIG. 1 according to one embodiment.
Figure 40:
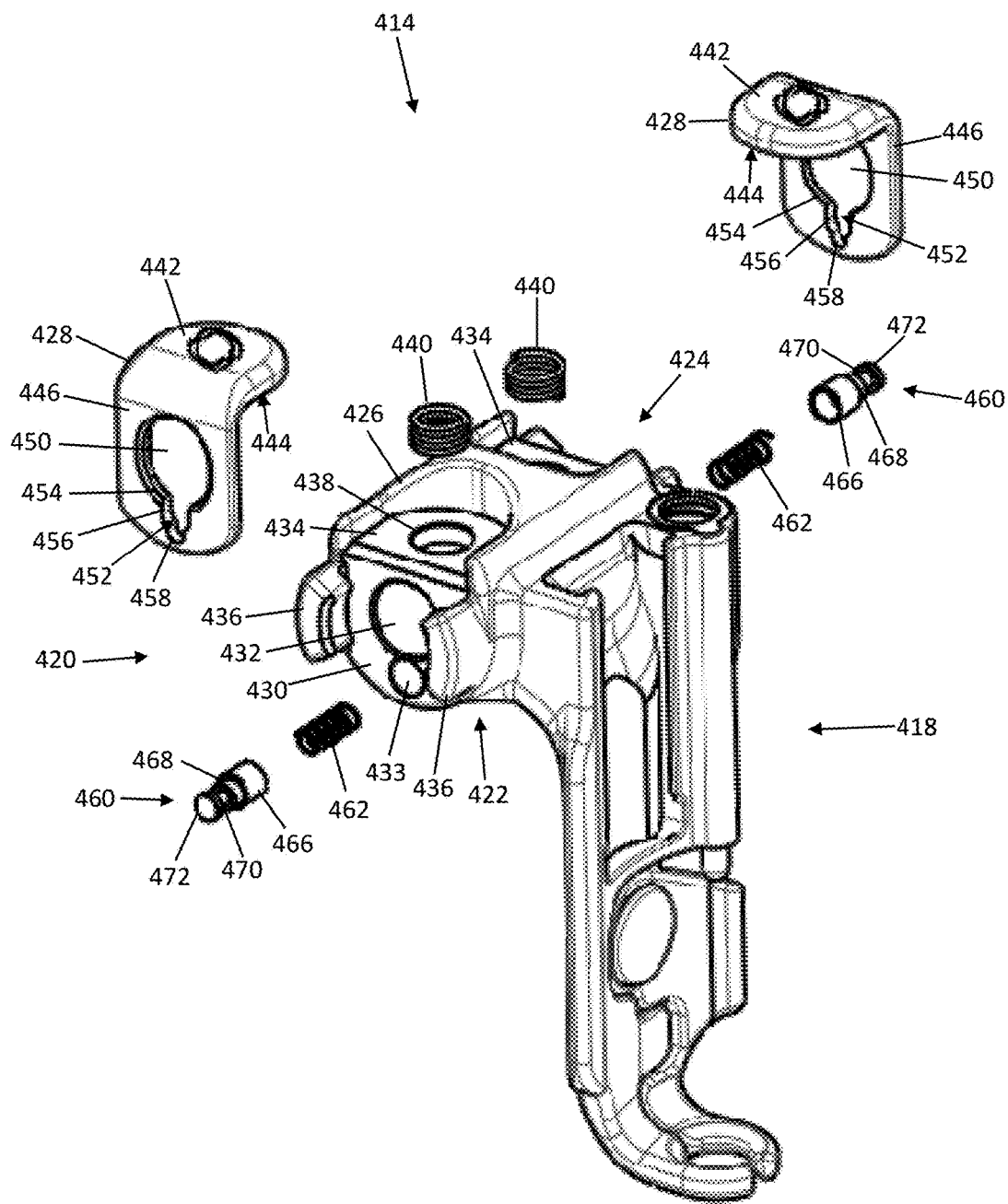
FIG. 40 is an exploded perspective view of the anchor blade of FIG. 39.
Figure 41:
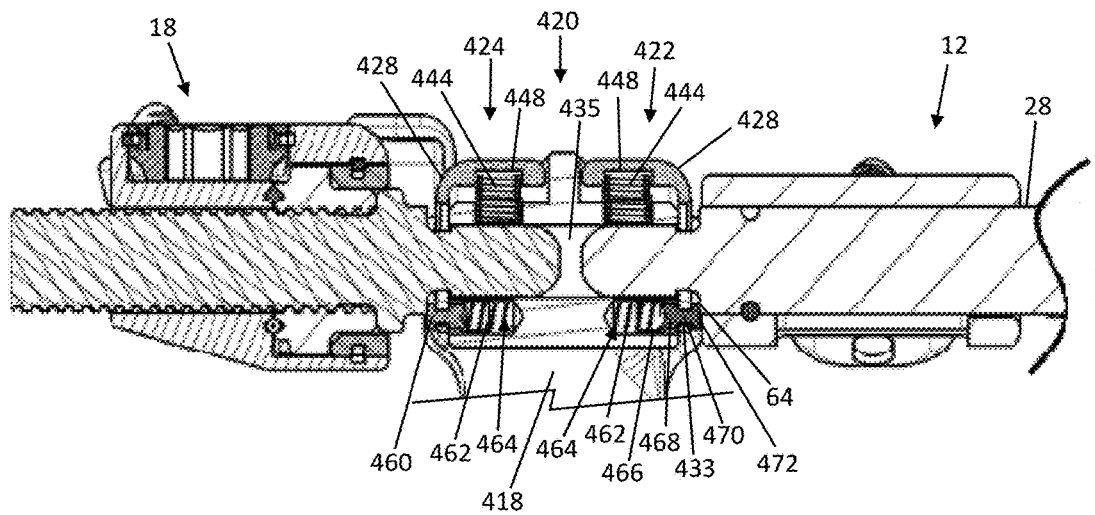
FIG. 41 is a sectional view of a portion of the retractor assembly of FIG. 1 with the anchor blade of FIG. 39 attached.

FIGS. 39-41 illustrate an example of an alternative anchor blade 414 configured for use with the tissue retractor assembly 10 described herein. Generally, anchor blade 414 has a blade portion 418 extending from a coupler 420. The blade portion 418 is identical in form and function to the blade portion 156 of the anchor blade 14 described above, and therefore all features disclosed with respect to blade portion 156 are attributable to blade portion 418 as well, rendering a repeat disclosure unnecessary.

The coupler 420 is integrally formed with the proximal portion of the anchor blade 414 and provides an alternative spring-loaded quick connect and release mechanism for engagement with the central post 66 of the left arm 28 (and/or the central post 98 of the right arm 30) described above. It should be understood that the anchor blades 414 and 416 are interchangeable in that either anchor blade 414 or anchor blade 416 may be used with either the left arm 28 or right arm 30. Therefore, only the interaction between the anchor blade 414 and the left arm 428 is described in detail herein, however all features herein described also apply to the interaction between the anchor blade 416 and the right arm 430. The coupler 420 has a proximal half 422 and a distal half 424. For the purpose of this disclosure, the proximal half 422 is defined as the portion of the coupler 420 that engages with left retractor arm 28, and the distal half 424 is defined as the portion of the coupler 420 that engages with the secondary retractor 18 (or the right retractor arm 30, if attached thereto). The proximal half 422 and distal half 424 of the coupler 420 are identical and as such the various features common to both halves will be assigned the same reference numerals for clarity.

The coupler 420 includes a housing 426 and a pair of release buttons 428. The housing 426 includes a proximal face 430 on the proximal end 422 (and an identical distal face on the distal end 424), an attachment aperture 432 extending through the proximal face 430, a trigger aperture 433 extending through the proximal face 430 below the attachment aperture 432, a pair of button recesses 434, and an interior lumen 435. The proximal face 430 includes a pair of flanges 436 extending proximally from the proximal face 430. When the anchor blade 414 is mated to the left arm 28, the proximal face 430 flushly interfaces with the distal face 64 of the left arm, and the flanges 436 engage with the recesses 68 formed in the distal face 64 of the left arm 28 to enable pivoting of the anchor blade 414 relative to the left arm (e.g. by moving the retractor body) until a sidewall of flange 436 engages a sidewall of the recess 68, after which the blade will rotate with the arm in response to user activation of the splay unit 74. The attachment aperture 432 receives the central post 66 of the left arm 28 therethrough such that the central post 66 can extend into the interior lumen 435 of the housing 426. The button recesses 434 are configured to provide a low profile nesting location for the release buttons 428 when the anchor blade 414 is in a "ready" state (e.g. prior to coupling with a left arm 28). The button recesses 434 each have a spring recess 438 positioned therein for housing one end of the button springs 440. The release buttons 428 each have a top surface 442, a bottom surface 444, and a locking flange 446 extending from the bottom surface 442. The top surface 442 is generally rounded to maintain a low profile and cause minimal disruption to surrounding anatomy during use, and is provided as a user engagement surface. The bottom surface 444 includes a spring recess 448 for housing the other end of the button spring 440. The locking flange 446 extends from the bottom surface 444 and includes a through-hole 450 and a trigger slot 452 extending below the through-hole 450. The through-hole 450 receives the central post 66 therethrough. The rim 454 of the through-hole 450 is sized and configured to nest within the circumferential recess 72 of the central post 66 to prevent egress of the central post 66 after the central post 66 has been fully inserted into the lumen 435 (thereby locking the anchor blade 414 to the left arm 28). The trigger slot 452 is divided into a first part 456 and a second part 458. The first part 456 has a width dimension that is complementary to the diameter of the middle portion 468 of the trigger button 460. The second part 458 has a width dimension that is complementary to the diameter of the end portion 470 of the trigger button 460. The coupler further includes a spring-loaded trigger button 460 that is at least partially housed, along with a trigger spring 462, within a trigger lumen 464 positioned underneath the interior lumen 435. The trigger button has a base 466, a middle portion 468 having a diameter that is smaller than the diameter of the base 466, an end portion 470 having a diameter that is smaller than the diameter of the middle portion 468, and an end cap 472 having a diameter that is greater than the diameter of the end portion 470.

In a detached or "ready" state (e.g. prior to coupling with the left arm 28), the trigger spring 464 exerts an outward force on the base 466 of the trigger button 460, which biases the middle portion 468 of the trigger button 460 through the trigger aperture 433 and at least partially into the first part 456 (i.e. wider part) of the trigger slot 452. This pulls the release button 428 downward so that the release button 428 is nested within the button recess 434 and the button springs 440 are compressed. In this state, the attachment aperture 432 of the housing 422 is aligned with the through-hole 450 of the release button 428, thereby allowing the insertion of the central post 66 into the interior lumen 435 to enable coupling of the anchor blade 414 and the left arm 28. During coupling of the anchor blade 414 and left arm 28, as the central post 66 is advanced through the through-hole 450 and attachment aperture 432 and into the interior lumen 435. As this advancement is occurring, the distal face 64 of the left arm encounters the trigger button 460 and exerts an inward force on the end cap 472. This inward force is greater than the outward force exerted by the trigger spring 462, and the trigger button 460 is urged into the trigger lumen 464. As the trigger button 460 is pushed further into the trigger lumen 464, the middle portion 468 is pushed entirely out of the first part 456 of the trigger slot 452, leaving only the end portion 470 in the trigger slot. The button spring 440 is thus allowed to release energy by exerting an upward force on the bottom surface 444 of the release button 428. This force snaps the release button 428 up, causing the end portion 470 of the trigger button 460 to snap into the second part 458 of the trigger slot 452 while simultaneously causing the rim 454 of the through-hole 450 to snap into the circumferential recess 72 of the central post 66 to prevent egress of the central post 66 after the central post 66 has been fully inserted into the lumen 435 (thereby locking the anchor blade 414 to the left arm 28). The forcible movement of the release button 428 makes the metal-on-metal contact between the rim 454 and the circumferential recess 72 audible, providing feedback to the user in the form of an audible "click" to indicate that the anchor blade 414 is secured to the retractor arm. In this "locked" state, the attachment aperture 432 and through-hole 450 are no longer in alignment (e.g. FIG. 39). To release the anchor blade 414, the user pushes the release button 428. This brings the attachment aperture 432 and through-hole 450 back into alignment while simultaneously evicting the rim 454 from the circumferential recess 72, enabling the central post 66 to be removed from the coupler 420.

Figure 42:
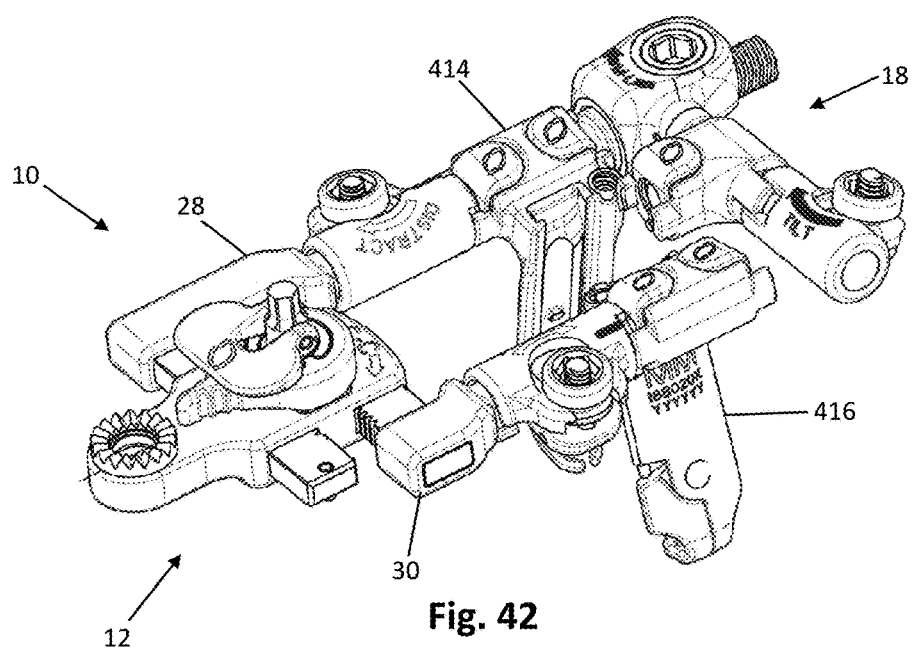
FIG. 42 is a perspective view of the retractor assembly of FIG. 1 with the anchor blade of FIG. 39 attached.

FIG. 42 illustrates the tissue retractor assembly 10 in use with anchor blades 414, 416 attached thereto. As with the anchor blades, 14, 16 described above, the anchor blades 414, 416 are virtually identical in form and function and therefore all features disclosed herein with regard to anchor blade 414 may be attributable to anchor blade 416 as well.

Figure 43:
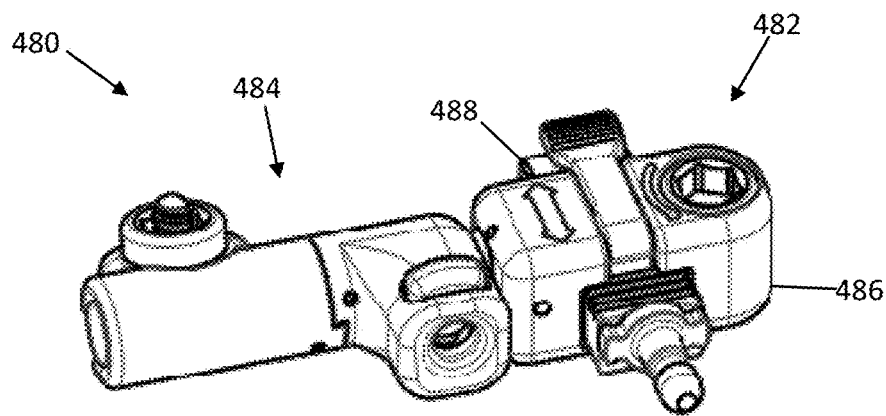
FIG. 43 is a perspective view an alternative example of a secondary retractor forming part of the retractor assembly of FIG. 1.
Figure 44:
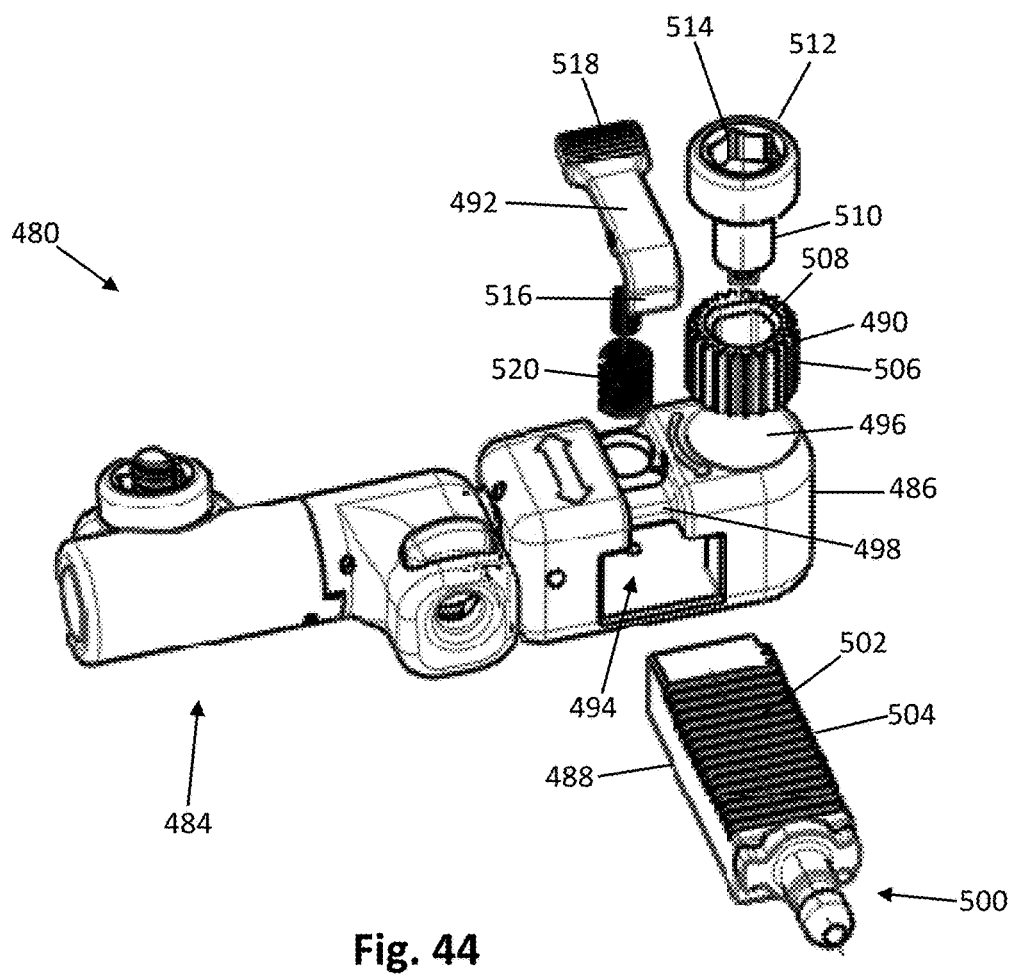
FIG. 44 is an exploded perspective view of the secondary retractor of FIG. 43.
Figure 45:
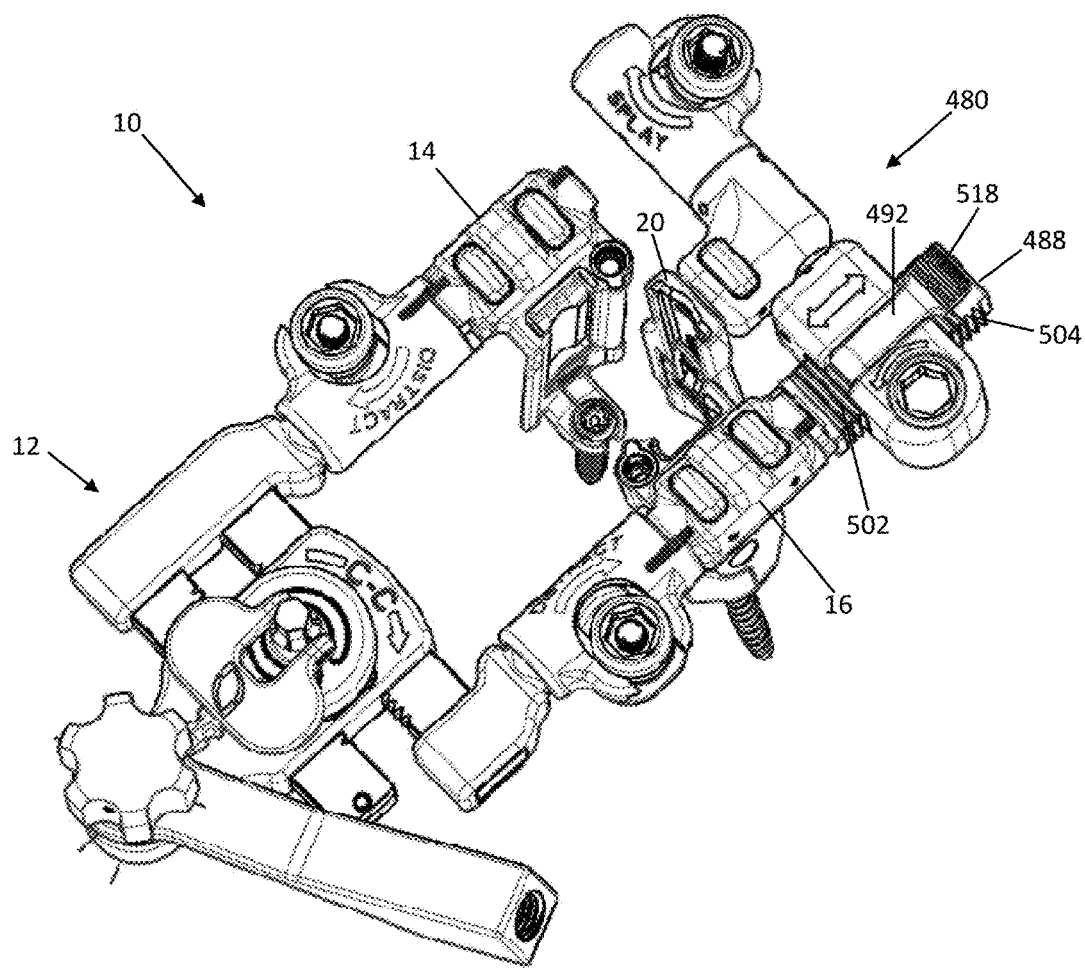
FIG. 45 is a perspective view of the retractor assembly of FIG. 1 with the secondary retractor of FIG. 43 attached.

FIGS. 43-45 illustrate another example of an alternative secondary retractor 480 that can attach to an assembled retractor 10 and has a self-locking mechanism. The secondary retractor 480 is attachable to the coupler 158 of the anchor blade 14 (or coupler 158' of anchor blade 16, or coupler 420 of anchor blade 414, etc.) and comprises a retraction assembly 482 and a blade assembly 484. The secondary retractor 480 allows for further connection to a secondary (e.g. medial) blade 20 and drives further access to the spine medially with many degrees of freedom. For example, the secondary retractor 480 may provide for medial retraction, medial splay, caudal-cranial pivoting and caudal-cranial translation. The retraction assembly 482 provides medial retraction and comprises a housing 486, a rack 488, a gear 490, and a pawl 492. The housing 486 has an interior lumen 494 through which the rack 488 extends, a gear recess 496 that receives the gear 490, and a pawl recess 498 that provides a low profile nest for the pawl 492. The rack 488 includes a proximal attachment end 500, a set of top teeth 502, and a set of side teeth 504. The attachment end 500 is virtually identical in structure and function to the distal face 96 of the first arm 28 described above, and thus a repeat discussion is unnecessary. The top teeth 502 are spaced relatively close together and are configured to engage with the pawl 492. The side teeth 504 are spaced farther apart than the top teeth 502 and are configured to engage the gear 490. The larger side teeth 504 allow for greater mechanical advantage during retraction when engaged with the gear 490, while the smaller teeth 502 allow for more discreet locking positions. The gear 490 includes a tooth portion 506 and an engagement recess 508. The engagement recess 508 receives a post 510 of an actuator element 512, which also includes an engagement recess 514 for engaging an actuator tool (not shown). Rotating the actuator element 512 causes the gear 490 to rotate, which in turn causes the rack 488 to translate within the lumen 494. The pawl 492 includes a distal engagement tip 516 and a spring-loaded proximal release lever 518. The distal engagement tip 516 engages with the top teeth 502 on the rack 488 to finely control the locking positions. A spring 520 biases the pawl 490 to contact the rack 488 in a ratchet-like manner. Pushing on the release lever 518 causes the distal engagement tip 516 to lift off the rack 488, enabling free movement of the rack 488. The blade assembly 484 is identical to the blade assembly 252 described above with reference to secondary retractor 18, and thus any feature disclosed in relation to blade assembly 252 is applicable to the blade assembly 484, rendering a repeat discussion unnecessary.

Figure 11:
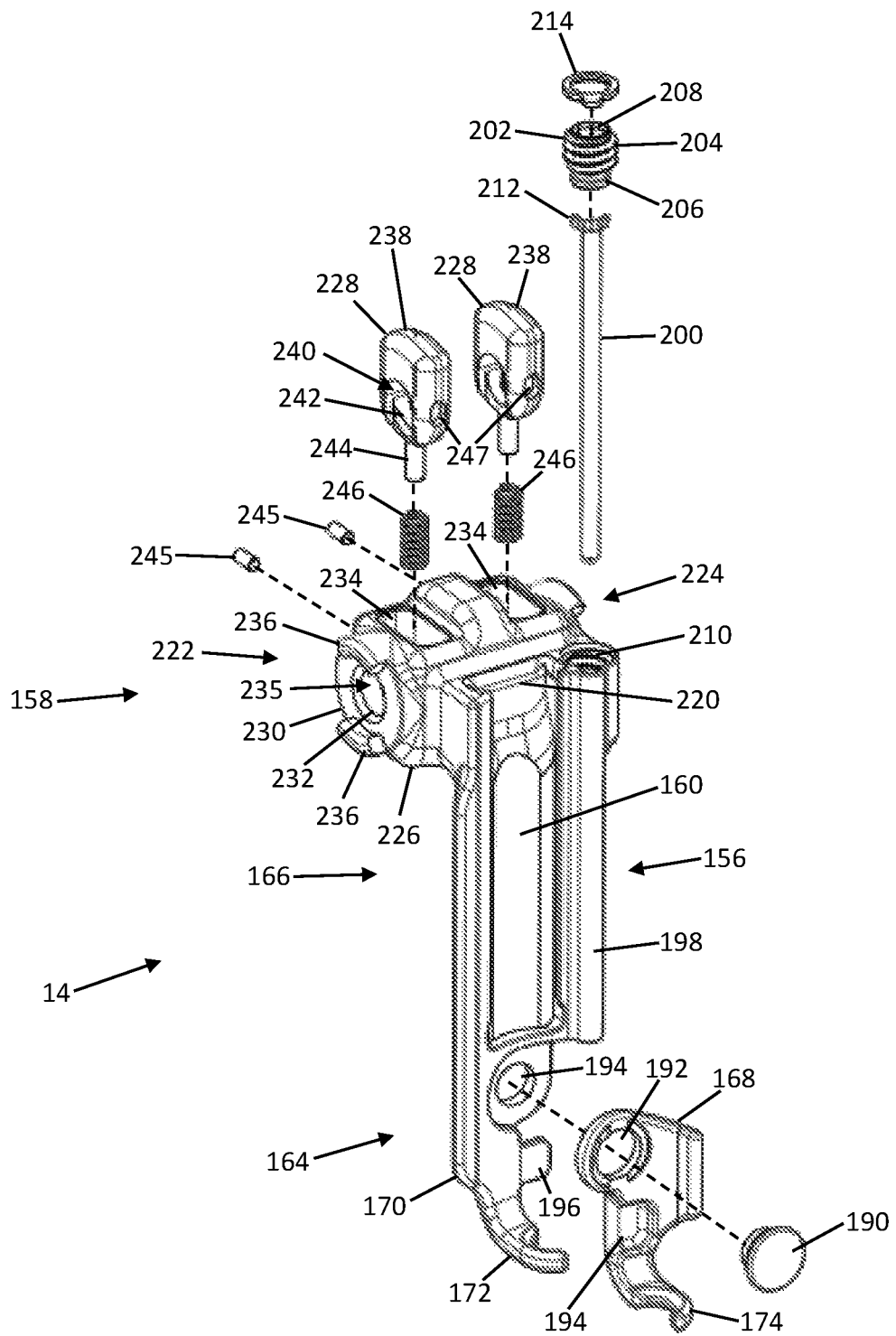
FIG. 11 is an exploded perspective view of an example of an anchor blade forming part of the retractor assembly of FIG. 1.
Figure 14:
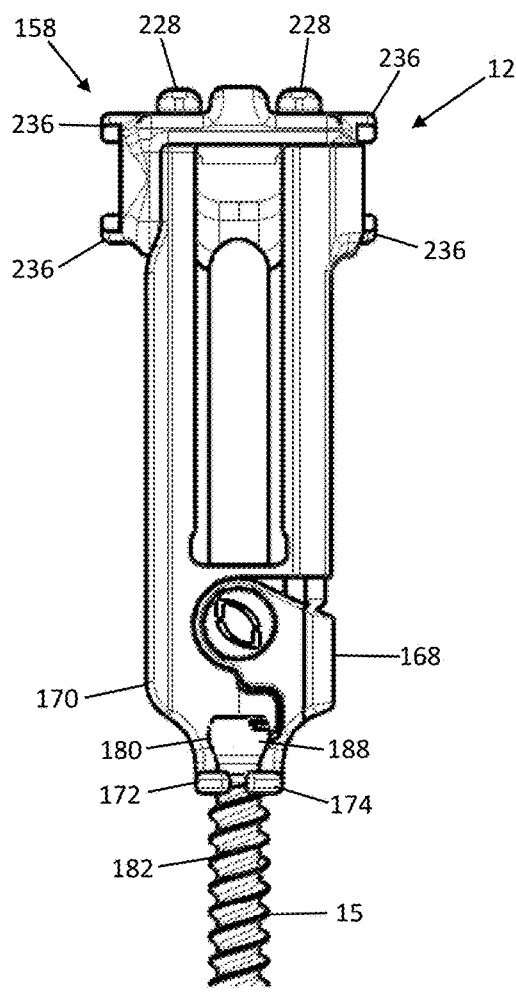
FIG. 14 is a plan view of the anchor blade of FIG. 11 with the pivot arm in a "closed" position.
Figure 15:
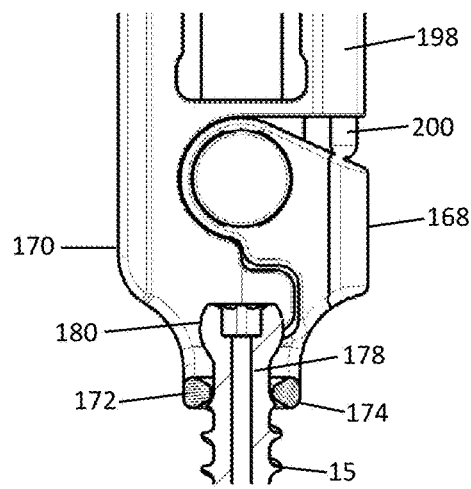
FIG. 15 is a sectional view of the distal portion of the anchor blade of FIG. 11 with the pivot arm in a "closed" position.
Figure 16:
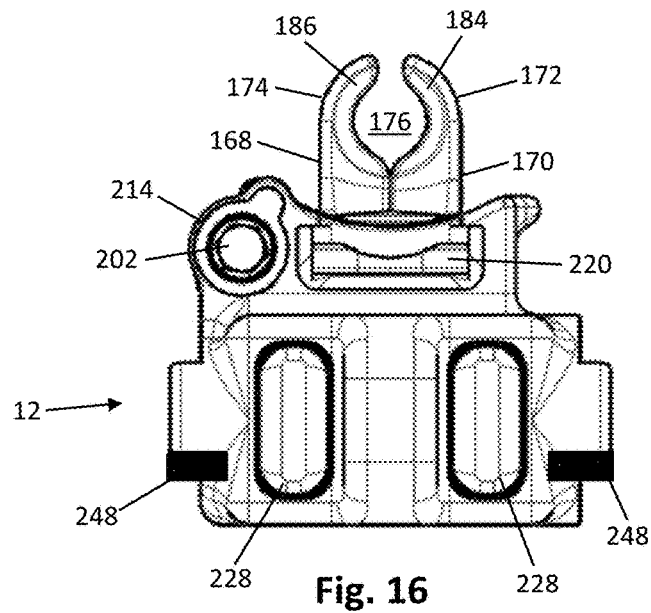
FIG. 16 is a top plan view of the anchor blade of FIG. 11.
Figure 17:
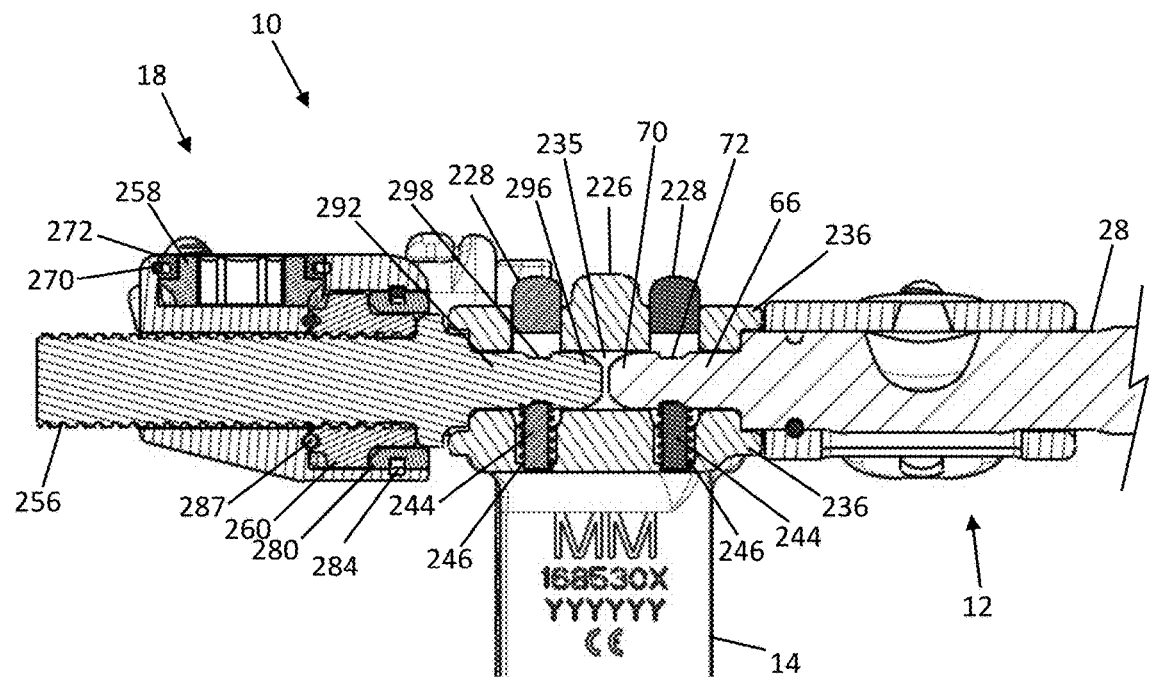
FIG. 17 is a sectional view of a portion of the retractor assembly of FIG. 1.
Figure 46:
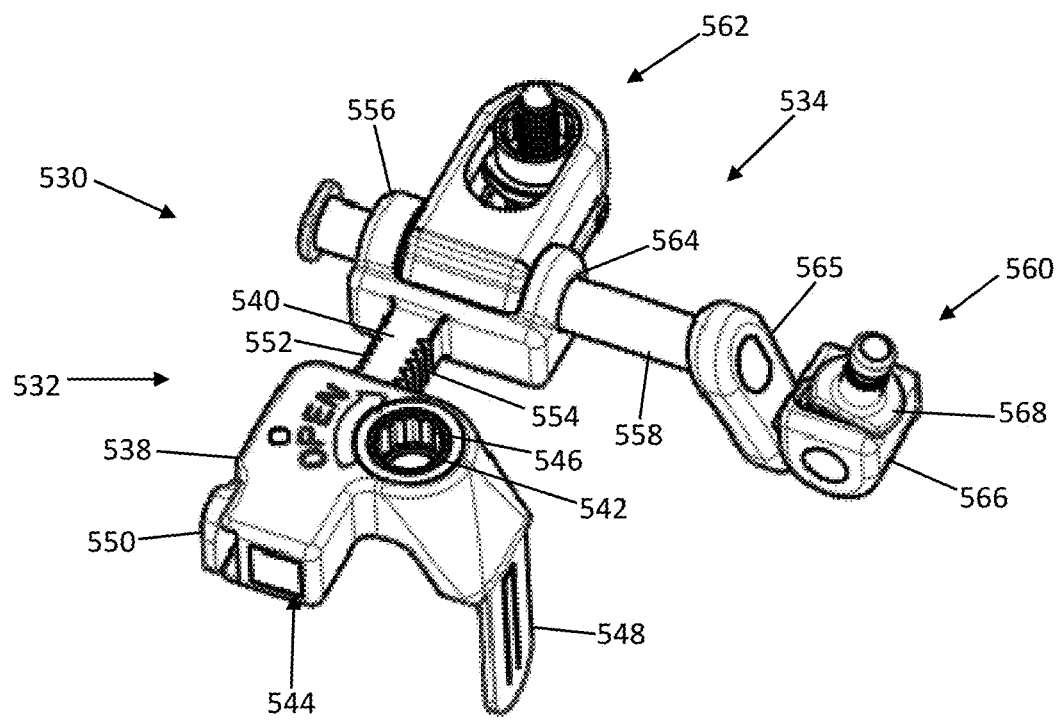
FIG. 46 is a perspective view an alternative example of a secondary retractor forming part of the retractor assembly of FIG. 1.
Figure 47:
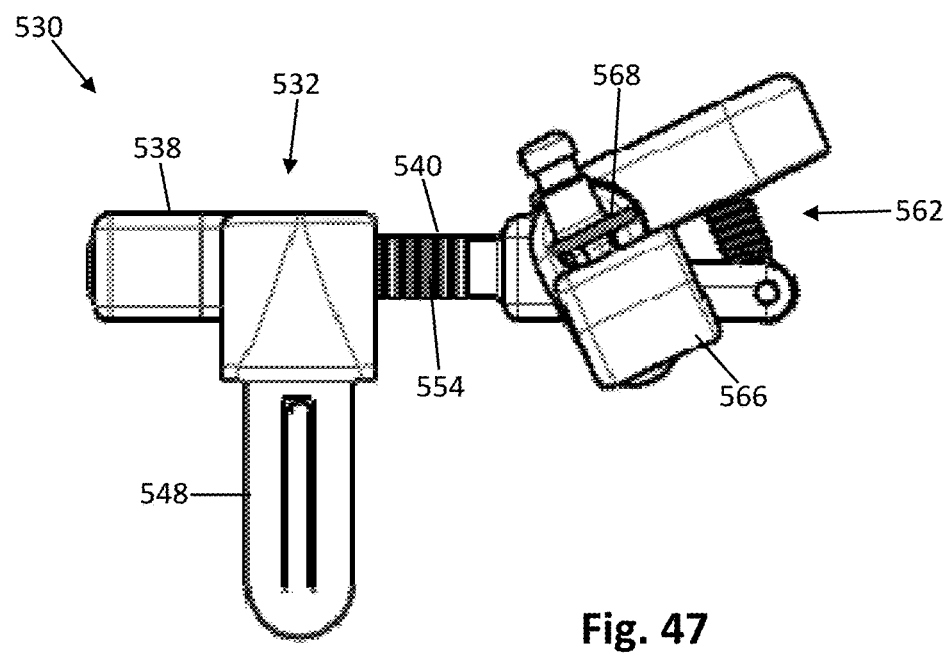
FIG. 47 is an exploded perspective view of the secondary retractor of FIG. 46.
Figure 48:
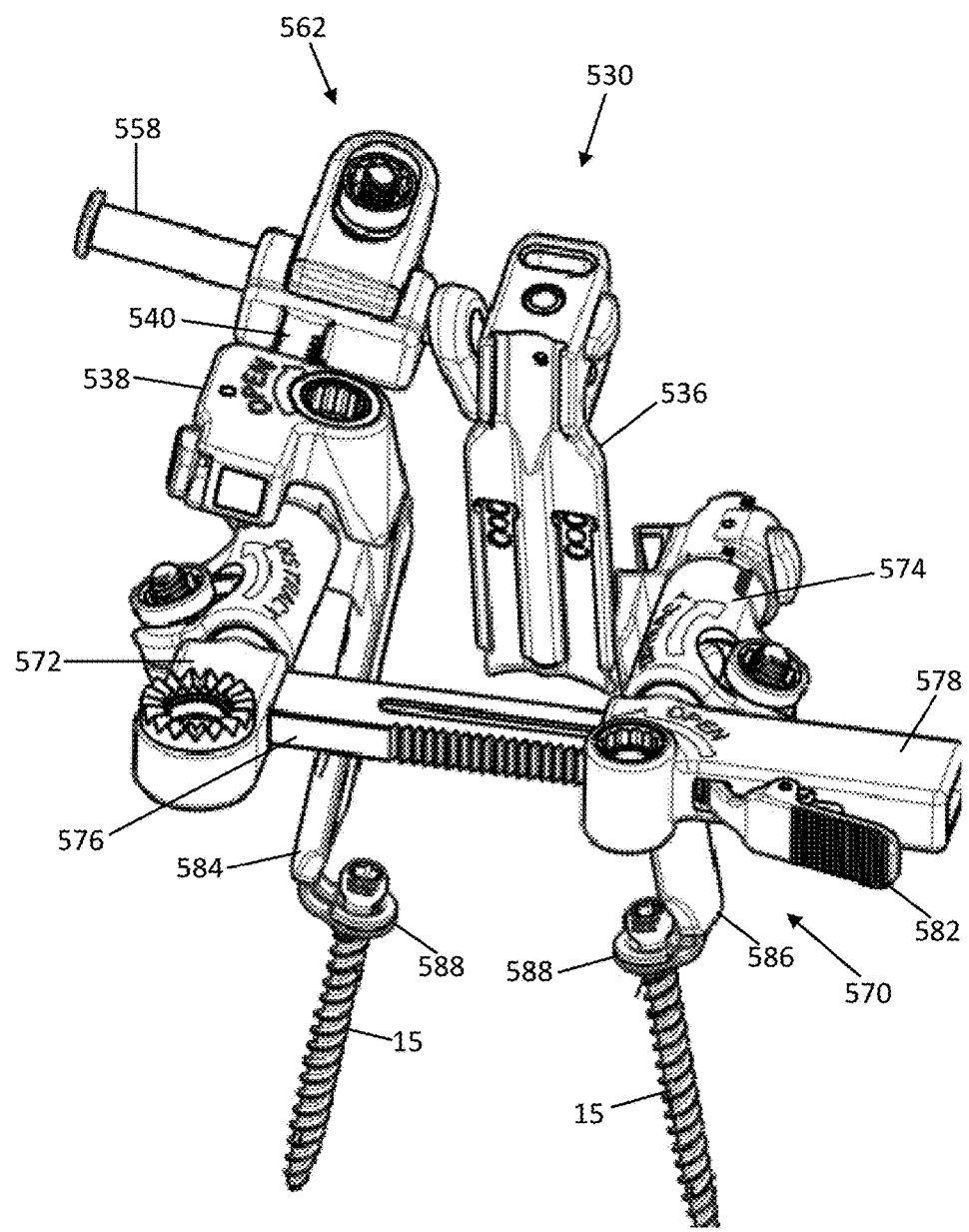
FIG. 48 is a perspective view of the secondary retractor of FIG. 46 attached to a basic example of a rack retractor.

FIGS. 46-48 illustrate another example of an alternative secondary retractor 530 that can attach to an assembled retractor assembly 10 according to one embodiment. The secondary retractor 530 is attachable to the caudal anchor blade 14 and comprises a retraction assembly 532 and a blade assembly 534. The secondary retractor 530 allows for further connection to a secondary (e.g. medial) blade 536 and drives further access to the spine medially with many degrees of freedom. For example, the secondary retractor 530 may provide for medial retraction, medial splay, caudal-cranial pivoting and caudal-cranial translation. The retraction assembly 532 provides medial retraction and comprises a housing 538, a rack 540, and a gear 542. The housing 538 has an interior channel 544 through which the rack 540 extends and within which the gear 542 engages the rack 538. The gear 542 includes a tooth portion (not shown) that engages the rack 540 and an engagement recess 546 that provides an engagement element for an actuator tool. The housing 538 further has an attachment flange 548 extending generally downward from the housing 538, and a pawl 550 configured to engage the teeth 552 of the rack 540, enabling fine resolution. The attachment flange is sized and configured to slideably engage the track 220 of the anchor blade 14 (FIG. 11). The rack 540 is double sided and has a first set of teeth 552 positioned on an opposite side of the rack from a second set of teeth 554. The first set of teeth 552 are spaced relatively close together and are configured to engage with the pawl 550. The second set of teeth 554 are spaced farther apart than the first set of teeth 552 and are configured to engage the gear 542. The larger second set of teeth 554 allow for greater mechanical advantage during retraction when engaged with the gear 542, while the smaller first set of teeth 552 allow for more discreet locking positions.

The blade assembly 534 includes a base 556, pivoting crossbar 558, a blade coupler 560 and a splay unit 562. The base is positioned at the distal end of the rack 540 and includes a channel 564 for receiving the pivoting crossbar 558. The pivoting crossbar 558 can translate up to an inch in distance and can rotate on axis up to 40° in a continuously variable fashion. The pivoting crossbar 558 may freely translate within the channel 564 and has an internal O-ring (not shown) which applies friction during translation guidance. The splay unit 562 controls rotation and is identical in form and function to the splay unit 74 of the left arm 28, and thus a detailed description of the like features need not be repeated. The pivoting crossbar 558 is attached to a crankshaft 565 that has an offset knuckle 566 and pivoting stud 568 allowing for attachment of a secondary blade 536. The crankshaft 565 allows the secondary blade 536 to be splayed offset of the axis of rotation of the pivoting crossbar 558. The eccentric movement persuades a secondary blade 536 to move up and out of the surgeon's line of sight while splaying. The secondary blade 536 attaches to the secondary retractor 530 with an internal self-locking quick connect mechanism, for example such as those described above.

FIG. 48 illustrates the secondary retractor 530 in use with a standard rack retractor 570, shown by way of example only. The secondary retractor 530 may be used with the retractor assembly 10 described above without departing from the scope of the disclosure. By way of example only, the standard rack retractor 570 includes a first arm 572 and second arm 574 connected via a crossbar rack 576. The first and second arms 572, 574 are virtually identical to the left and right arms 28, 30 described above. The crossbar rack 576 is received within a housing 578, which itself has a gear 580 and pawl 582. Anchor blades 584, 586 differ from the several embodiments described above in that they attach to the bone anchors 15 via hoop shims 588.

While the inventive features described herein have been described in terms of a preferred embodiment for achieving the objectives, it will be appreciated by those skilled in the art that variations may be accomplished in view of these teachings without deviating from the spirit or scope of the invention.

What is claimed is:

1. A retractor blade forming part of a surgical retractor for accessing a spinal target site during comprising;
    a connector and a blade portion, the connector being configured to couple the retractor blade with a surgical retractor, the blade portion including a distal end comprising a static arm with a static foot extending transversely from the pivot arm and a pivot arm with a pivot foot extending transversely from the pivot arm, the pivot arm pivotally coupled to the static arm and movable between a closed position in which the pivot foot and static foot cooperate to form a capture ring configured capture an implantable bone anchor therein and an open position configured permit passage of the implantable bone anchor into and out of the capture ring.

2. The retractor blade of claim 1, wherein the retractor blade further comprises a lock to lock the pivot arm in the closed position.

3. The retractor blade of claim 2, wherein the lock comprises a shaft that translates through a passage extending along one side of the retractor blade to engage the pivot arm.

4. The retractor blade of claim 3, wherein the pivot arm is biased to the open position and the shaft engages a ramped surface of the pivot arm to pivot the pivot arm towards the static arm as the shaft translates downward.

5. The retractor blade of claim 4, wherein the translation of the shaft is controlled by a set screw situated at the top of the retractor blade.

6. The retractor blade of claim 1, wherein a gap exists between ends of the static foot and pivot foot when in the closed position.

7. The retractor blade of claim 6, wherein an inner surface of the capture ring is curved and angled.

8. The retractor blade of claim 1, wherein the connector includes a coupling mechanism configured to automatically lock the retractor blade to the retractor when engaged.

9. The retractor blade of claim 8, wherein the coupling mechanism includes a release button configured to unlock the retractor blade from the retractor to facilitate decoupling.

10. The retractor blade of claim 9, wherein the connector includes a second coupling mechanism structurally identical to the coupling mechanism.

* * * * *